US007115267B2

(12) United States Patent
Wolpe et al.

(10) Patent No.: US 7,115,267 B2
(45) Date of Patent: Oct. 3, 2006

(54) STIMULATOR OF STEM CELL DIVISION

(75) Inventors: Stephen D. Wolpe, Rockville, MD (US); Irena Tsyrlova, Gaithersburg, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 0 days.

(21) Appl. No.: 10/776,172

(22) Filed: Feb. 12, 2004

(65) Prior Publication Data

US 2004/0167060 A1 Aug. 26, 2004

Related U.S. Application Data

(63) Continuation of application No. 08/832,443, filed on Apr. 3, 1997, now Pat. No. 6,784,155, which is a continuation-in-part of application No. 08/627,173, filed on Apr. 3, 1996, now Pat. No. 5,861,483.

(51) Int. Cl.
| | |
|---|---|
| A61K 35/00 | (2006.01) |
| A61K 38/16 | (2006.01) |
| A61K 38/00 | (2006.01) |
| A61K 38/04 | (2006.01) |

(52) U.S. Cl. .................. 424/185.1; 514/6; 514/14; 530/327; 530/326

(58) Field of Classification Search ............. 424/185.1; 514/6, 14; 530/327, 326
See application file for complete search history.

(56) References Cited

U.S. PATENT DOCUMENTS

| | | | |
|---|---|---|---|
| 4,350,683 A | 9/1982 | Galfre et al. | |
| 4,683,194 A | 7/1987 | Saiki et al. | |
| 5,028,588 A | 7/1991 | Hoffman et al. | |
| 5,239,061 A | 8/1993 | Fronticelli et al. | |
| 5,334,706 A | 8/1994 | Przybelski | |
| 5,449,759 A | 9/1995 | Hoffman et al. | |
| 5,631,219 A | 5/1997 | Rosenthal et al. | |
| 5,786,334 A | 7/1998 | Petrov et al. | |
| 5,861,483 A | 1/1999 | Wolpe et al. | |
| 5,939,391 A | 8/1999 | Tsyrlova et al. | |
| 6,022,848 A | 2/2000 | Kozlov et al. | |
| 6,090,782 A | 7/2000 | Tsyrlova et al. | |
| 6,280,739 B1 * | 8/2001 | Jacobs et al. ............. 424/198.1 |
| 6,784,155 B1 * | 8/2004 | Wolpe et al. .................. 514/6 |

FOREIGN PATENT DOCUMENTS

| | | |
|---|---|---|
| SU | 1561261 A1 | 4/1988 |
| SU | 1614655 A1 | 5/1988 |
| WO | WO 90/13645 | 11/1990 |
| WO | WO 91/04274 | 4/1991 |
| WO | WO 92/11283 | 7/1992 |
| WO | WO 92 20369 | 11/1992 |
| WO | WO 93/09143 | 5/1993 |
| WO | WO 93/ 25071 | 12/1993 |
| WO | WO 94/05785 | 3/1994 |
| WO | WO 94/122915 | 10/1994 |
| WO | WO 95/24213 | 9/1995 |
| WO | WO 96/10634 | 4/1996 |

OTHER PUBLICATIONS

Becker et al. "The Effect of Differing Demands for Blood Cell Production on DNA Synthesis by Hemopoietic Colony-Forming Cells of Mice" Blood 26(3): 296-308 (1965).
Broxmeyer et al. "Involvement of the MU Opioid Receptor in Myeloid Progenitor Cell Proliferation: Evidence from MU Opioid Receptor Gene Knockout Mice" Blood 88:338a, Abstract 1339 (1996).
Broxmeyer et al. "Myelopoietic Enhancing Effects of Murine Macrophage Inflammatory Proteins 1 and 2 on Colony Formation In Vitro by Murine and Human Bone Marrow Granulocyte/Macrophage Progenitor Cells" J Exp Med 170:1583-1594 (1989).
Byron "Effect of Steroids on the Cycling of Haemopoietic Stem Cells" Nature 228:1204 (1970).
Davatelis et al. "Cloning and Characterization of a cDNA for Murine Macrophage Inflammatory Protein (MIP), a Novel Monokine with Inflammatory and Chemokinetic Properties" J Exp Med 157:1939-1944 (1988).
Davatelis et al. "Macrophage Inflammatory Protein-1: A Prostaglandin-Independent Endogenous Pyrogen" Science 243:1066-1068 (1989).
Dexter et al. "Loss of Immunoreactivity in Long-Term Bone Marrow Culture" Nature 275:135-136 (1978).
Dunlop et al. "Demonstration of Stem Cell Inhibition and Myeloprotective Effects of SCI/rhMIP1α In Vivo" Blood 79(9):2221-2225 (1992).
Eaves et al. "Clinical Significance of Long-Term Cultures of Myeloid Blood Cells" CRC Critical Reviews in Oncology/Hematology 7(2):125-138 (1987).
Eaves et al. "The Therapeutic Potential of Long-Term Cultures of Myeloid CML Marrow Cultures" The Biology of Hematopoiesis (Daniak, ed.), Alan R. Liss, NY.
Eaves et al. "Maintenance and Proliferation Control of Primative Hemopoietic Progenitors in Long-Term Cultures of Human Marrow Cells" Blood Cells 14:355-368 (1988).
Eaves et al. "Mechanisms That Regulate the Cell Cycle Status of Very Primative Hematopoietic Cells in Long-Term Human Marrow Cultures. II. Analysis of Positive and Negative Regulators Produced by Stromal Cells Within the Adherent Layer" Blood 78(1):110-117 (1991).
Enoki et al. "Preparation of Native α and β Subunits from Canine Hemoglobin" Biochim Biophys Acta 744:71-75 (1983).

(Continued)

*Primary Examiner*—Christina Chan
*Assistant Examiner*—Michail Belyavskyi
(74) *Attorney, Agent, or Firm*—Nixon & Vanderhye P.C.

(57) ABSTRACT

Disclosed and claimed are methods for the isolation and use of stem cell modulating factors for regulating stem cell cycle and for accelerating the post-chemotherapy peripheral blood cell recovery. Also disclosed and claimed are the inhibitors and stimulators of stem cell proliferation.

8 Claims, 28 Drawing Sheets

OTHER PUBLICATIONS

Goldberg et al. "Regulatory Effects of Opioid Peptides on Bone Marrow Hematopoiesis in Stress" (abstract only) Biull Eksp Biol Med 108(8):216-219 (1989).

Goldberg et al. "The Modulating Influence of Enkephalins on the Bone Marrow Haemopoiesis in Stress" Folia Biologica (Praha) 36(6):319-331 (1990).

Golovanova et al. "Influence of the Factor of Stem Cell Inhibition on the Formation of Hemopoietic Colonies" Ontogenez 13(3):243-250 (1982).

Graham et al. "Identification and Characterization of an Inhibitor of Haemopoietic Stem Cell Proliferation" Nature 344:442-444 (1990).

Harrison et al. "Most Primitive Hematopoietic Stem Cells Are Stimulated to Cycle Rapidly After Treatment With 5-Fluorouracil" Blood 78(5):1237-1240 (1991).

Hunkapiller et al. "Isolation of Microgram Quantities of Proteins from Polyacrylamide Gels for Amino Acid Sequence Analysis" Meth Enzymol 91:227-236 (1983).

Hwang et al. "Identification of Residues Involved in the Binding of Hemoglobin $\alpha$ Chains to Haptoglobin" J Biol Chem 254(7):2265-2270 (1979).

Ignat'Eva et al. "Study of the Mechanism of Action of the Stem Cell Inhibition Factor on the Formation of Exogenous Hemopoietic Colonies in the Spleen on Mice" (abstract only) Biull Eksp Biol Med 98(9):326-329 (1984).

James et al. "The Isolation of the $\gamma$ Subunit of Fetal Hemoglobin (HbF) and Its Use in a Radioimmunoassay for HbF" J Immunol Meth 32:251-260 (1980).

Karelin et al. "Proteolytic Degradation of Hemoglobin in Erythrocytes Leads to Biologically Active Peptides" Peptides 16(4):693-697 (1995).

Kozlov et al. "The Effect of Haemopoietic Stem Cell Proliferation on the Humoral Immune Response in Mice" Cell Tissue Kinet 20:485-491 (1987).

Kriegler et al. "Identification of the "Factor" in Erythrocyte Lysates Which Enhances Colony Growth in Agar Cultures" Exp Hematol 9(1):11-21 (1981).

Krizanac-Bengez et al. "Effect of Enkephalins on Bone Marrow Cells" Biomed Pharmacother 46:367-373 (1992).

Krizanac-Bengez et al. "Naloxone Behaves as Opioid Agonist/Antagonist in Clonal Cultures of Mouse Bone Marrow Cells" Biomed Pharmacother 49:27-31 (1995).

Krizanac-Bengez et al. "Suppressive Effect of Met-Enkephalin on Bone Marrow Cell Proliferation In Vitro Shows Circadian Pattern and Depends on the Presence of Adherent Accessory Cells" Biomed Pharmacother 50:85-91 (1996).

Lathe "Synthetic Oligonucleotide Probes Deduced from Amino Acid Sequence Data Theoretical and Practical Considerations" J Mol Biol 183:1-12 (1985).

Lord et al. "An Inhibitor of Stem Cell Proliferation in Normal Bone Marrow" Br J Haematol 34:441-445 (1976).

Lord et al. "Inhibitor of Haemopoietic CFU-S Proliferation: Assays, Production Sources and Regulatory Mechanisms" In: The Inhibitors of Hematopoiesis (Najman et al., eds.) 162:227-239 (1987).

Lord et al. "Macrophage-Inflammatory Protein Protects Multipotent Hematopoietic Cells from the Cytotoxic Effects of Hydroxyurea In Vivo" Blood 79(10):2605-2609 (1992).

Lord et al. "Sources of Haemopoietic Stem Cell Proliferation: Stimulators and Inhibitors" Blood Cells 6:581-593 (1980).

McCormick et al. "Antigenic Structure of Human Hemoglobin: Delineation of the Antigenic Site (Site 2) Within Region 41-65 of the Alpha Chain by Immunochemistry of Synthetic Peptides" J Prot Chem 4(3):171-184 (1985).

McDonald et al. "Structural, Functional, and Subunit Assembly Properties of Hemoglobin Attleboro[$\alpha$138 (H21) Ser$\rightarrow$Pro], A Variant Possessing a Site Mutation at a Critical C-Terminal Residue" Biochem 29(7):173-178 (1990).

Michel et al. "Removal of Arg$^{141}$ from the $\alpha$ Chain of Human Hemoglobin by Carboxypeptidases N and M" Circ Res 78(4):635-642 (1996).

Moqattash et al. "Hemopoietic Recovery from AZT Toxicity with Recombinant Hemoglobin in a Murine Model of AIDS" Acta Haematol 92:182-186 (1994).

Mueller et al. "Purified Adult Hemoglobin Stimulates the Proliferation and Differentiation of Erythroid Progenitors" Blood 86(10):496a, Abstract 1974 (1995).

Mundy et al. "Loss of Immunoreactivity in Long-Term Bone Marrow Culture" Nature 275:135-136 (1978).

Ohtsuka et al. "An Alternative Approach to Deoxyoligonucleotides as Hybridization Probes by Insertion of Deoxyinosine at Ambiguous Codon Positions" J Biol Chem 260(5):2605-2608 (1985).

Phillips et al. "Allogeneic Bone Marrow Transplantation Using Unrelated Donors: A Pilot Study of the Canadian Bone Marrow Transplant Group" Bone Marrow Transplant 8:477-487 (1991).

Shaeffer"Heterogeneity in the Structure of the Ubiquitin Conjugates of Human $\alpha$ Globin" J Biol Chem 269(47):29530-29536 (1994).

Swanson et al. "Production of Functional Human Hemoglobin In Transgenic Swine" Bio/Technology 10:557-559 (1992).

Tejero et al. "The Cellular Specificity of Haemopoietic Stem Cell Proliferation Regulators" Br J Cancer 50:335-341 (1984).

Terpstra et al. "The Preparation of Human Hemoglobin $\alpha$-Subunit and a Study of Its Monomer-Dimer Association" Can J Biochem 54(11):1002-1010 (1976).

Tian et al. "Altered Hematopoiesis, Behavior, and Sexual Function in $\mu$ Opioid Receptor-Deficient Mice" J Exp Med 185(8): 1517-1522 (1997).

Till et al. "A Direct Measurement of the Radiation Sensitivity of Normal Mouse Bone Marrow Cell" Radiation Res 14:213-222 (1961).

Toksoz et al. "The Regulation of Hemopoiesis in Long-Term Bone Marrow Cultures II. Stimulation and Inhibition of Stem Cell Proliferation" Blood 55(6):931-936 (1980).

Tsyrlova et al "Improvement of Leukemic LTBMC Establishment by Using a Specific Inhibitor of Hematopoietic Stem Cell Proliferation" Leukemia: Advances in Biology and Therapy—Progress and Controversies S326 (1988).

Visser et al. "Isolation of Spleen-Colony Forming Cells (CFU-s) Using Wheat Germ Agglutinin and Rhodamine 123 Labeling" Blood Cells 14:369-384 (1988).

Whitlock et al. "In Vitro Analysis of Murine B-Cell Development" Ann Rev Immunol 3:213-235 (1985).

Wolpe et al. "Macrophages Secrete a Novel Heparin-Binding Protein with Inflammatory and Neutrophil Chemokinetic Properties" J Exp Med 167:570-581 (1988).

Supplementary European Search Report dated Nov. 6, 2002.

* cited by examiner

Analysis: Channel A

| Peak No. | Time | Type | Height(μY) | Area(μY-sec) | Area% |
|---|---|---|---|---|---|
| 1 | 4.383 | N1 | 3945 | 95125 | 0.119 |
| 2 | 5.080 | N2 | 28639 | 330889 | 0.413 |
| 3 | 5.216 | N3 | 49084 | 531867 | 0.665 |
| 4 | 7.980 | N1 | 399424 | 1110511 | 1.389 |
| 5 | 8.100 | Err' | 1203320 | 2882013 | 3.605 |
| 6 | 8.241 | N3 | 443249 | 1506159 | 1.884 |
| 7 | 8.386 | N4 | 481563 | 2185702 | 2.734 |
| 8 | 8.533 | N5 | 412886 | 1826165 | 2.284 |
| 9 | 8.701 | N6 | 321500 | 842122 | 1.053 |
| 10 | 8.745 | N7 | 404661 | 1610380 | 2.014 |
| 11 | 8.995 | N8 | 435765 | 2489721 | 3.114 |
| 12 | 9.316 | N9 | 517790 | 4801831 | 6.007 |

FIG. 16A

```
  1   2   3   4   5   6   7   8   9  10  11  12  13  14  15  16  17  18  19  20
 Val Leu Ser Pro Ala Asp Lys Thr Asn Val Lys Ala Ala Trp Gly Lys Val Gly Ala His
 GTG CTG TCT CCT GCC GAC AAG ACC AAC GTC AAG GCC GCC TGG GGT AAG GTC GGC GCG CAC 21  22  23  24  25  26  27  28  29  30  31  32  33  34  35  36  37  38  39  40
 Ala Gly Glu Tyr Gly Ala Glu Ala Leu Glu Arg Met Phe Leu Ser Phe Pro Thr Thr Lys
 GCT GGC GAG TAT GGT GCT GAG GCC CTG GAG AGg ATG TTC CTG TCC TTC CCC ACC ACC AAG 41  42  43  44  45  46  47  48  49  50  51  52  53  54  55  56  57  58  59  60
 Thr Tyr Phe Pro His Phe Asp Leu Ser His Gly Ser Ala Gln Val Lys Gly His Gly Lys
 ACC TAC TTC CCG CAC TTC GAC CTG AGC CAC GGC TCT GCC CAG GTT AAG GGC CAC GGC AAG 61  62  63  64  65  66  67  68  69  70  71  72  73  74  75  76  77  78  79  80
 Lys Val Ala Asp Ala Leu Thr Asn Ala Val Ala His Val Asp Asp Met Pro Asn Ala Leu
 AAG GTG GCC GAC GCC CTG ACC AAC GCC GTG GCG CAC GTG GAC GAC ATG CCC AAC GCG CTG 81  82  83  84  85  86  87  88  89  90  91  92  93  94  95  96  97  98  99 100
 Ser Ala Leu Ser Asp Leu His Ala His Lys Leu Arg Val Asp Pro Val Asn Phe Lys Leu
 TCC GCC CTG AGC GAC CTG CAC GCC CAC AAG CTT CGG GTG GAC CCG GTC AAC TTC AAG CTC 101 102 103 104 105 106 107 108 109 110 111 112 113 114 115 116 117 118 119 120
 Leu Ser His Cys Leu Leu Val Thr Leu Ala Ala His Leu Pro Ala Glu Phe Thr Pro Ala
 CTA AGC CAC TGC CTG CTG GTG CTG CTC GCC GCC CAC CTC CCC GCC GAG TTC ACC CCT GCG 121 122 123 124 125 126 127 128 129 130 131 132 133 134 135 136 137 138 139 140 141
 Val His Ala Ser Leu Asp Lys Phe Leu Ala Ser Val Ser Thr Val Leu Thr Ser Lys Tyr Arg
 GTG CAC GCT TCC CTG GAC AAG TTC CTG GCT TCT GTG AGC ACC GTG CTG ACC TCC AAA TAC CGT
```

FIG. 16B

```
  1           2           3           4           5           6           7           8           9          10          11          12          13          14          15          16          17          18          19          20
Val         His         Leu         Thr         Pro         Glu         Glu         Lys         Ser         Ala         Val         Thr         Ala         Leu         Trp         Gly         Lys         Val         Asn         Val
GTG         CAC         CTG         ACT         CCT         GAG         GAG         AAG         TCT         GCC         GTT         ACT         GCC         CTG         TGG         GGT         AAG         GTG         AAC         GTG 21          22          23          24          25          26          27          28          29          30          31          32          33          34          35          36          37          38          39          40
Asp         Glu         Val         Gly         Gly         Glu         Ala         Leu         Gly         Arg         Leu         Leu         Val         Val         Tyr         Pro         Trp         Thr         Gln         Arg
GAT         GAA         GTT         GGT         GGT         GAG         GCT         CTG         GGC         AGg         CTG         CTG         GTC         GTC         TAC         CTT         TGG         ACC         CAG         AGG 41          42          43          44          45          46          47          48          49          50          51          52          53          54          55          56          57          58          59          60
Phe         Phe         Glu         Ser         Phe         Gly         Asp         Leu         Ser         Thr         Pro         Asp         Ala         Val         Met         Gly         Asn         Pro         Lys         Val
TTC         TTT         GAG         TCC         TTT         GGG         GAT         CTG         TCC         ACT         CCT         GAT         GCT         GTT         ATG         GGC         AAC         CCT         AAG         GTG 61          62          63          64          65          66          67          68          69          70          71          72          73          74          75          76          77          78          79          80
Lys         Ala         His         Gly         Lys         Lys         Val         Leu         Gly         Ala         Phe         Ser         Asp         Gly         Leu         Ala         His         Leu         Asp         Asn
AAG         GCT         CAT         GGC         AAG         AAA         GTG         CTC         GGT         GCC         TTT         AGT         GAT         GGC         CTG         GCT         CAC         CTG         GAC         AAC 81          82          83          84          85          86          87          88          89          90          91          92          93          94          95          96          97          98          99         100
Leu         Lys         Gly         Thr         Phe         Ala         Thr         Leu         Ser         Glu         Leu         His         Cys         Asp         Lys         Leu         His         Val         Asp         Pro
CTC         AAG         GGC         ACC         TTT         GCC         ACA         CTG         AGT         GAG         CTG         CAC         TGT         GAC         AAG         CTG         CAC         GTG         GAT         CCT 101         102         103         104         105         106         107         108         109         110         111         112         113         114         115         116         117         118         119         120
Glu         Asn         Phe         Arg         Leu         Leu         Gly         Asn         Val         Leu         Val         Cys         Val         Leu         Ala         His         His         Phe         Gly         Lys
GAG         AAC         TTC         AGG         CTC         CTG         GGC         AAC         GTG         CTG         GTC         TGT         GTG         CTG         GCC         CAT         CAC         TTT         GGC         AAA 121         122         123         124         125         126         127         128         129         130         131         132         133         134         135         136         137         138         139         140
Glu         Phe         Thr         Pro         Pro         Val         Gln         Ala         Ala         Tyr         Gln         Lys         Val         Val         Ala         Gly         Val         Ala         Asn         Ala
GAA         TTC         ACC         CCA         CCA         GTG         CAG         GCT         GCC         TAT         CAG         AAA         GTG         GTG         GCT         GGT         GTG         GCT         AAT         GCC 141         142         143         144         145         146
Leu         Ala         His         Lys         Tyr         His
CTG         GCC         CAC         AAG         TAT         CAC
```

FIG. 16C

```
                 10         20         30         40         50
hHemA.pep    1  V-LSPADKIN VKAAWGKVGA HA-GEYGAEA LE-RMFLSFP TTKTYFPHF-   50
hHemB.pep    1  VHLTPEEKSA VTALWGKV-- -NVDEVGGEA LG-RLLVVYP WTQRFFESFG   50
mHemA.pep    1  V-LSGEDKSN IKAAWGKIGG HG-AEYGAEA LE-RMFASFP TTKTYFPHF-   50
mHemB.pep    1  VHLTDAEKAA VSCLWGKVNS D---EVGGEA L-GRLLVVYP WTQRYFDSFG   50
pHemA.pep    1  V-LSAADKAN VKAAWGKVGG QA-GAHGAEA LE-RMFLGFP TTKTYFPHF-   50
pHemB.pep    1  VHLSAEEKEA VLGLWGKVNV D---EVGGEA L-GRLLVVYP WTQRFFESFG   50

60         70         80         90        100
hHemA.pep   51  DLSH----- G SAQVKGHGKK VADALTN--- AVAHVDDMPN ALS--ALSDL  100
hHemB.pep   51  DLSTPDAVMG NPKVKAHGKK VLGA---FSD GLAHLDNLKG TFA--TLSEL  100
mHemA.pep   51  DVSH-----G SAQVKGHGKK VADALAS--- AAGHLDDLPG ALS--ALSDL  100
mHemB.pep   51  DLSSASAIMG NAKVKAHGKK V---ITAFND GLNHLDSLKG TFASL--SEL  100
pHemA.pep   51  V-LSAH---G SDQVKAHGQK VADALTK--- AVGHLDDLPG ALS--ALSDL  100
pHemB.pep   51  DLSNADAVMG NPKVKAHGKK V---LQSFSD GLKHLDNLKG TFAKL--SEL  100

110        120        130        140        150
hHemA.pep  101  HAHKLRVDPV NFKLLSHCLL VTLAAHLPAE FTPAVHASLD -KFLASVSTV  150
hHemB.pep  101  HCDKLHVDPE NFRLLGNVLV CVLAHHFGKE FTPPVQAAYQ -KVVAGVANA  150
mHemA.pep  101  HAHKLRVDPV NFKLLSHCLL VTLASHHPAD FTPAVHASLD -KFLASVSTV  150
mHemB.pep  101  HCDKLHVDPE NFRLLGNMIV IVLGHHLGKD FTPAAQAAF- QKVVAGVATA  150
pHemA.pep  101  HAHKLRVDPV NFKLLSHCLL VTLAAHHPDD FNPSVHASLD -KFLANVSTV  150
pHemB.pep  101  HCDQLHVDPE NFRLLGNVIV VVLARRLGHD FNPDVQAAF- QKVVAGVANA  150

160        170        180        190        200
hHemA.pep  151  LTSKYR....                                               200
hHemB.pep  151  LAHKYH....                                               200
mHemA.pep  151  LTSKYR....                                               200
mHemB.pep  151  LAHKYH....                                               200
pHemA.pep  151  LTSKYR....                                               200
pHemB.pep  151  LAHKYH....                                               200
```

Analysis Channel A

| Peak No. | Time | Type | Height(μY) | Area (μY-sec) | Area % |
|---|---|---|---|---|---|
| 1 | 48.200 | N | 1677 | 20438 | 1.515 |
| 2 | 52.076 | N1 | 7625 | 116393 | 8.631 |
| 3 | 52.510 | N2 | 32010 | 881490 | 65.369 |
| 4 | 53.660 | N3 | 10066 | 330153 | 24.483 |
| Total Area | | | | 1348474 | 99.998 |

Analysis Channel A

| Peak No. | Time | Type | Height(μY) | Area (μY-sec) | Area % |
|---|---|---|---|---|---|
| 1 | 47.110 | N1 | 1727 | 24840 | 0.204 |
| 2 | 47.723 | N2 | 75067 | 1738939 | 14.321 |
| 3 | 49.153 | N3 | 188795 | 6206410 | 51.114 |
| 4 | 52.250 | N1 | 81476 | 3046748 | 25.092 |
| 5 | 52.115 | N2 | 13195 | 202166 | 1.664 |
| 6 | 53.613 | N3 | 19211 | 914954 | 7.535 |
| | 65.753 | N | 818 | 8066 | 0.066 |
| Total Area | | | | 12142123 | 99.996 |

Comparison of Inprol and Hemoglobin Chains in FDPCmix Assay

STIMULATOR OF STEM CELL DIVISION

This application is a division of application Ser. No. 08/832,443, filed Apr. 3, 1997, now U.S. Pat. No. 6,784,155; which is a continuation-in-part of application Ser. No. 08/627,173, filed Apr. 3, 1996, now U.S. Pat. No. 5,861,483.

BACKGROUND OF THE INVENTION

Most end-stage cells in renewing systems are short-lived and must be replaced continuously throughout life. For example, blood cells originate from a self-renewing population of multipotent hematopoietic stem cells (HSC). Hematopoietic stem cells are a subpopulation of hematopoietic cells. Hematopoietic cells can be obtained, for example, from bone marrow, umbilical cord blood or peripheral blood (either unmobilized or mobilized with an agent such as G-CSF), hematopoietic cells include the stem cell population, progenitor cells, differentiated cells, accessory cells, stromal cells and other cells that contribute to the environment necessary for production of mature blood cells. Hematopoietic progenitor cells are a subset of stem cells which are more restricted in their developmental potency. Progenitor cells are able to differentiate into only one or two lineages (e.g., BFU-E and CFU-E which give rise only to erythrocytes or CFU-GM which give rise to granulocytes and macrophages) while stem cells (such as CFU-MIX or CFU-GEMM) can generate multiple lineages and/or other stem cells. Because the hematopoietic stem cells are necessary for the development of all of the mature cells of the hematopoietic and immune systems, their survival is essential in order to reestablish a fully functional host defense system in subjects treated with chemotherapy or other agents.

Hematopoietic cell production is regulated by a series of factors that stimulate growth and differentiation of hematopoietic cells, some of which, for example erythropoietin, GM-CSF and G-CSF, are currently used in clinical practice. One part of the control network which has not been extensively characterized, however, is the physiological mechanism that controls the cycling status of stem cells (Eaves et al. Blood 78:110–117, 1991; Lord, in *Stem Cells* (C. S. Potten, Ed.) pp 401–22, 1997 (Academic Press, NY)).

Early studies by Lord and coworkers showed the existence of soluble protein factors in normal and regenerating bone marrow extracts which could either inhibit or stimulate stem cell proliferation (reviewed in: Lord and Wright, Blood Cells 6:581–593, 1980; Wright and Lorimore, Cell Tissue Kinet. 20:191–203, 1987; Marshall and Lord, Int Rev. Cyt. 167:185–261, 1996). These activities were designated stem cell inhibitor (SCI) and stem cell stimulator (SCS), respectively.

To date, no candidate SCS molecules have been purified from bone marrow extracts prepared as described by Lord et al. (reviews referenced above). Purification of either SCS or SCI from primary sources was not accomplished due to the difficulties inherent in an in vivo assay requiring large numbers of irradiated mice. In an attempt to overcome these problems Pragnell and co-workers developed an in vitro assay for primitive hematopoietic cells (CFU-A) and screened cell lines as a source of the inhibitory activity (see Graham et al. Nature 344:442–444, 1990). As earlier studies had identified macrophages as possible sources for SCI (Lord et al. Blood Cells 6:581–593, 1980), a mouse macrophage cell line, J774.2, was selected (Graham et al. Nature 344:442–444, 1990). The conditioned medium from this cell line was used by Graham et al. for purification; an inhibitory peptide was isolated which proved to be identical to the previously described cytokine macrophage inflammatory protein 1-alpha (MIP-1α). Receptors for MIP-1α have been cloned; like other chemokine receptors, these MIP-1α receptors are seven-transmembrane domain (or "G-linked") receptors which are coupled to guanine nucleotide (GTP) binding proteins of the $G_{inhibitory}$ subclass ("$G_i$") (reviewed in Murphy, Cytokine & Growth Factor Rev. 7:47–64, 1996). The "inhibitory" designation for the $G_i$ subclass refers to its inhibitory activity on adenylate cyclase.

MIP-1α was isolated from a cell line, not from primary material. While Graham et al. observed that antibody to MIP-1α abrogated the activity of a crude bone marrow extract, other workers have shown that other inhibitory activities are important. For example, Graham et al. (J. Exp. Med. 178:925–32, 1993) have suggested that TGFβ. not MIP-1α, is a primary inhibitor of hematopoietic stem cells. Further, Eaves et al. (PNAS 90:12015–19, 1993) have suggested that both MIP-1α and TGFβ are present at sub optimal levels in normal bone marrow and that inhibition requires a synergy between the two factors.

Recently, mice have been generated in which the MIP-1α gene has been deleted by homologous recombination (Cook et al., Science 269:1583–5, 1995). Such mice have no obvious derangement of their hematopoietic system, calling into question the role of MIP-1α as a physiological regulator of stem cell cycling under normal homeostatic conditions. Similarly, although transforming growth factor beta (TGFβ) also has stem cell inhibitory activities, the long period of time it takes for stem cells to respond to this cytokine suggests that it is not the endogenous factor present in bone marrow extracts; further, neutralizing antibodies to TGFβ do not abolish SCI activity in bone marrow supernatants (Hampson et al., Exp. Hemat. 19:245–249, 1991).

Other workers have described additional stem cell inhibitory factors. Frindel and coworkers have isolated a tetrapeptide from fetal calf marrow and from liver extracts which has stem cell inhibitory activities (Lenfant et al., PNAS 86:779–782, 1989). Paukovits et al. (Cancer Res. 50:328–332, 1990) have characterized a pentapeptide which, in its monomeric form, is an inhibitor and, in its dimeric form, is a stimulator of stem cell cycling. Other factors have also been claimed to be inhibitory in various in vitro systems (see Wright and Pragnell in *Bailliere's Clinical Haematology* v. 5, pp. 723–39, 1992 (Bailliere Tinadall, Paris); Marshall and Lord, Int Rev. Cyt. 167:185–261, 1996).

Tsyrlova et al., SU 1561261 A1, disclosed a purification process for a stem cell proliferation inhibitor.

Commonly owned applications WO 94/22915 and WO96/10634 disclose an inhibitor of stem cell proliferation, and are hereby incorporated by reference in their entirety.

To date, none of these factors have been approved for clinical use. However, the need exists for effective stem cell inhibitors. The major toxicity associated with chemotherapy or radiation treatment is the destruction of normal proliferating cells which can result in bone marrow suppression or gastrointestinal toxicity. An effective stem cell inhibitor will protect these cells and allow for the optimization of these therapeutic regimens. Just as there is a proven need for a variety of stimulatory cytokines (i.e., cytokines such as IL-1, IL-2, IL-3, IL-4, IL-5, IL-6, IL-7, IL-9, IL-1, IL-13, IL-14, IL-15, G-CSF, GM-CSF, erythropoietin, thrombopoietin, stem cell factor, flk2/flt3 ligand, etc., which stimulate the cycling of hematopoietic cells) depending upon the clinical situation, so too it is likely that a variety of inhibitory factors will be needed to address divergent clinical needs.

Further, there is a need to rapidly reverse the activity of such an inhibitor. The original studies of Lord et al. (reviews referenced above) demonstrated that the inhibitory activity could be reversed by addition of the stimulatory activity. While a variety of stem cell stimulatory cytokines has been identified (see above), none has been demonstrated to represent the activity described by Lord and coworkers as being present in bone marrow extracts and of being able to reverse the activity of the inhibitor.

Hematopoietic progenitors and stem cells primarily reside in the bone marrow in normal adults. Under certain conditions, for example chemotherapy or treatment with cytokines such as G-CSF, large numbers of progenitors and stem cells egress into the peripheral blood, a process referred to as "mobilization" (reviewed in Simmons et al., Stem Cells 12 (suppl 1): 187–202, 1994; Scheding et al. Stem Cells 12 (suppl 1):203–11, 1994; Mangan, Sem. Oncology 22:202–9, 1995; Moolten, Sem. Oncology 22:271–90, 1995). Recent published data suggest that the vast majority of mobilized progenitors are not actively in cell cycle (Roberts and Metcalf, Blood 86:1600-, 1995; Donahue et al., Blood 87:1644-, 1996; Siegert and Serke, Bone Marrow Trans. 17:467- 1996; Uchida et al., Blood 89:465–72, 1997).

Hemoglobin is a highly conserved tetrameric protein with molecular weight of approximately 64,000 Daltons. It consists of two alpha and two beta chains. Each chain binds a single molecule of heme (ferroprotoporphyrin IX), an iron-containing prosthetic group. Vertebrate alpha and beta chains were probably derived from a single ancestral gene which duplicated and then diverged; the two chains retain a large degree of sequence identity both between themselves and between various vertebrates (see FIG. 16A). In humans, the alpha chain cluster on chromosome 16 contains two alpha genes (alpha$_1$ and alpha$_2$) which code for identical polypeptides, as well as genes coding for other alpha-like chains: zeta, theta and several non-transcribed pseudogenes (see FIG. 16B for cDNA and amino acid sequences of human alpha chain). The beta chain cluster on chromosome 11 consists of one beta chain gene and several beta-like genes: delta, epsilon, G gamma and A gamma, as well as at least two unexpressed pseudogenes (see FIG. 16C for cDNA and amino acid sequences of human beta chain).

The expression of these genes varies during development. In human hematopoiesis, which has been extensively characterized, embryonic erythroblasts successively synthesize tetramers of two zeta chains and two epsilon chains (Gower I), two alpha chains and two epsilon chains (Gower II) or two zeta chains and two gamma chains (Hb Portland). As embryogenesis proceeds, the predominant form consists of fetal hemoglobin (Hb F) which is composed of two alpha chains and two gamma chains. Adult hemoglobin (two alpha and two beta chains) begins to be synthesized during the fetal period; at birth approximately 50% of hemoglobin is of the adult form and the transition is complete by about 6 months of age. The vast majority of hemoglobin (approximately 97%) in the adult is of the two alpha and two beta chain variety (Hb A) with small amounts of Hb F or of delta chain (Hb A$_2$) being detectable.

Several methods have been used to express recombinant hemoglobin chains in *E. coli* and in yeast (e.g., Jessen et al., Methods Enz. 231:347–364, 1994; Looker et al. Methods Enz. 231:364–374, 1994; Ogden et al., Methods Enz. 231: 374–390, 1994; Martin de Llano et al., Methods Enz. 231:364–374, 1994). It has thus far not been possible to express isolated human alpha chain in high yields by recombinant methods (e.g., Hoffman et al., PNAS 87:8521–25, 1990; Heman et al., Biochem. 31:8619–28, 1992). Apparently, the isolated alpha chain does not assume a stable conformation and is rapidly degraded in *E. coli*. Co-expression of beta chain with alpha chain results in increased expression of both (Hoffman et al. and Hernan et al., op. cit.). While the alpha chain has been expressed as a fusion protein with a portion of the beta chain and a factor Xa recognition site (Nagai and Thorgersen, Methods Enz. 231: 347–364, 1994) it is expressed as an insoluble inclusion body under these conditions.

Both the beta chain and the alpha chain contain binding sites for haptoglobin. Haptoglobin is a serum protein with extremely high affinity for hemoglobin (e.g., Putnam in *The Plasma Proteins—Structure, Function and Genetic Control* (F. W. Putnam, Ed.) Vol. 2, pp 1–49 (Academic Press, NY); Hwang and Greer, JBC 255:3038–3041, 1980). Haptoglobin transport to the liver is the major catabolic pathway for circulating hemoglobin. There is a single binding site for haptoglobin on the alpha chain (amino acids 121–127) and two on the beta chain (amino acid regions 11–25 and 131–146) (Kazim and Atassi, Biochem J. 197:507–510, 1981; McCormick and Atassi, J. Prot. Chem. 9:735–742, 1990).

Biologically active peptides with opiate activity have been obtained by proteolytic degradation of hemoglobin (reviewed in Karelin et al., Peptides 16:693–697, 1995). Hemoglobin alpha chain has an acid-labile cleavage site between amino acids 94–95 (Shaeffer, J. Biol. Chem. 269: 29530–29536, 1994).

Kregler et al. (Exp. Hemat. 9:11–21, 1981) have disclosed that hemoglobin has an enhancing activity on mouse bone marrow CFU-C progenitor colonies. Such assays demonstrate effects on CFU-GM and CFU-M progenitor populations as opposed to stem cells such as CFU-MIX. The authors observed activity in both isolated alpha and beta chains of hemoglobin. This activity was abolished by treatment with N-ethylmaleimide, which suggested to Kregler et al. that sulfhydryl groups were necessary. This observation, coupled with the fact that the stimulatory activity was resistant to trypsin digestion, suggested to Kregler et al. that the C-terminal hydrophobic domain or "core" region was responsible for the activity. Moqattash et al. (Acta. Haematol. 92:182–186, 1994) have disclosed that recombinant hemoglobin has a stimulatory effect on CFU-E, BFU-E and CFU-GM progenitor cell number which is similar to that observed with hemin. Mueller et al. (Blood 86:1974, 1995) have disclosed that purified adult hemoglobin stimulates erythroid progenitors in a manner similar to that of hemin.

Petrov et al. (Bioscience Reports 15:1–14, 1995) disclosed the use of a "nonidentified myelopeptide mixture" in the treatment of congenital anemia in the W$^v$/W$^v$ mouse. The mixture increased the number of spleen colonies, especially those of the erythroid type.

Heme and hemin have been extensively examined with regard to their influences on hematopoiesis (see S. Sassa, Seminars Hemat. 25:312–20, 1988 and N. Abraham et al., Int. J. Cell Cloning 9:185–210, 1991 for reviews). Heme is required for the maturation of erythroblasts; in vitro, hemin (chloroferroprotoporphyrin IX—i.e., heme with an additional chloride ion) increases the proliferation of CFU-GEMM, BFU-E and CFU-E. Similarly, hemin increases cellularity in long-term bone marrow cultures.

"Opiates" are substances with analgesic properties similar to morphine, the major active substance in opium. Opiates can be small organic molecules, such as morphine and other alkaloids or synthetic compounds, or endogenous peptides such as enkephalins, endorphins, dynorphins and their synthetic derivatives. Endogenous opiate peptides are produced in vivo from larger precursors—pre-proenkephalin A for Met- and Leu-enkephalins, pre-proopiomelanocortin for α, β, and γ endorphins, and pre-prodynorphin for dynorphins A and B, α-neoendorphin and β-neoendorphin. In addition, peptides with opiate activity can be obtained from non-classical sources such as proteolysis or hydrolysis of proteins such as α or β casein, wheat gluten, lactalbumin, cytochromes or hemoglobin, or from other species such as frog skin (dermorphins) or bovine adrenal medulla. Such peptides have been termed "exorphins" in contrast to the classical endorphins; they are also referred to as a typical opiate peptides (Zioudrou et al., JBC 254:2446–9, 1979; Quirion and Weiss, Peptides 4:445, 1983; Loukas et al. Biochem. 22:4567, 1983; Brantl, Eur. J. Pharm. 106:213–14, 1984; Brantl et al., Eur. J. Pharm. 111:293–4, 1985; Brantl et al., Eur. J. Pharm. 125:309–10, 1986; Brantl and Neubert, TIPS 7:6–7,1986; Glamsta et al., BBRC 184:1060–6, 1992; Teschemacher, Handbook Exp. Pharm. 104:499–28, 1993; Petrov et al., Bioscience Reports 15:1–14, 1995; Karelin et al., Peptides 16:693–7, 1995). Other endogenous peptides, such as the Tyr-MIF-1 family, have also been shown to have opiate activity (Reed et al., Neurosci. and Biobehav. Rev. 18:519–25, 1994).

Opiates exert their actions by binding to three main pharmacological classes of endogenous opiate receptors—mu, delta, and kappa. Receptors representing each pharmacological class have been cloned and shown to be G-linked receptors coupled to $G_i$ (reviewed in: Reisine and Bell, TINS 16: 506–510, 1993; Uhl et al., TINS 17:89–93, 1994; Knapp et al., FASEB J. 9:516–525, 1995; Satoh and Minami, Pharm. Ther. 68:343–64, 1995; Kieffer, Cell. Mol. Neurobiol. 15:615–635, 1995; Reisine, Neuropharm. 34:463–472, 1995; Zaki et al., Ann. Rev. Pharm. Toxicol., 36:379–401, 1996).

Specific agonists and antagonists are available for each receptor type—e.g., for mu receptors (which are selectively activated by DAIMGO and DALDA and selectively antagonized by CTOP and naloxonazine), for kappa receptors (which are selectively activated by GR 89696 fumarate or U-69593 and selectively antagonized by nor—binaltorphimine hydrochloride) and for delta receptors (which are selectively activated by DADLE and DPDPE and selectively antagonized by natrindole). In addition, there are broad-spectrum antagonists (such as naloxone) and agonists (such as etorphine) which act on all three receptor subtypes.

Both classical and atypical opiate peptides can be chemically altered or derivatized to change their specific opiate receptor binding properties (reviewed in Hruby and Gehrig, Med. Res. Rev. 9:343–401, 1989; Schiller, Prog. Med. Chem. 28: 301–40, 1991; Teschemacher, Handbook Exp. Pharm. 104:499–28, 1993; Handbook of Experimental Pharmacology, A. Hertz (Ed.) volumes 104/II and 104/II, 1993, Springer Verlag, Berlin; Karelin et al., Peptides 16:693–7, 1995). Examples include derivatives of dermorphin (e.g., DALDA) and enkephalins (e.g., DADLE, DAIMGO or DAMME). Peptides which do not normally bind to opiate receptors, such as somatostatin, can also be derivatized to exhibit specific opiate receptor binding (e.g., CTOP (Hawkins et al., J. Pharm. Exp. Ther. 248:73, 1989)). Analogs can also be derived from alkaloids such as morphine with altered receptor binding properties (e.g., heroin, codeine, hydromorphone, oxymorphone, levorphanol, levallorphan, codeine, hydrocodone, oxycodone, nalorphine, naloxone, naltrexone, buprenorphine, butanorphanol and nalbuphine); in addition, small molecules structurally unrelated to morphine can also act on opiate receptors (e.g., meperidine and its congeners alphaprodine, diphenoxylate and fentanyl) (see Handbook of Experimental Pharmacology, op. cit.; Goodman and Gilman's *The Pharmacological Basis of Therapeutics.* 7th Ed., A. G. Gilman, L. S. Goodman, T. W. Rall and F. Murad (Eds.) 1985 Macmillan Publishing Co. NY).

The endogenous opiate peptides (enkephalins, endorphins and dynorphins) have a conserved N-terminal tetrapeptide Tyr-Gly-Gly-Phe, followed by Leu or Met and any remaining C-terminal sequence. Removal of the hydroxyl group on the N-terminal Tyr (resulting in an N-terminal Phe) results in a dramatic loss of activity for Met-enkephalin. These structural data led to the "message-address" hypothesis whereby the N-terminal "message" confers biological activity while the C-terminal "address" confers specificity and enhanced potency (Chavkin and Goldstein, PNAS 78:6543–7, 1981). Exorphins generally have a Tyr-Pro replacing the N-terminal Tyr-Gly of classical opiate peptides; the proline residue is thought to confer higher stability against aminopeptidase degradation (Shipp et al., PNAS 86: 287-, 1989; Glamsta et al., BBRC 184:1060–6, 1992).

Recently an orphan receptor ("ORL1") was cloned by virtue of sequence relatedness to the mu, delta and kappa opiate receptors (Mollereau et al., FEBS 341:33–38, 1994; Fukuda et al., FEBS 343:42–46, 1994; Bunzow et al., FEBS 347:284–8, 1994; Chen et al., FEBS 347:279–83, 1994; Wang et al., FEBS 348:75–79, 1994; Keith et al., Reg. Peptides 54 143–4, 1994; Wick et al., Mol. Brain Res. 27: 37–44, 1994, Halford et al., J. Neuroimmun. 59:91–101, 1995). The ligand for this receptor, variously called nociceptin or orphanin FQ (referred to hereafter as "nociceptin") has been cloned and shown to be a heptadecapeptide which is derived from a larger precursor (Meunier et al., Nature 377:532–535, 1995; Reinscheid et al., Science 270:792–794, 1995). It was demonstrated to have pronociceptive, hyperalgesic functions in vivo, as opposed to classical opiates which have analgesic properties. Nociceptin has a Phe-Gly-Gly-Phe . . . N-terminal motif in contrast to the Tyr-Gly-Gly-Phe . . . N-terminal motif of classical opiate peptides discussed above. In keeping with the requirement for an N-terminal Tyr for opiate activity in classical opiate peptides, nociceptin exhibits little or no affinity for the mu, kappa or delta opiate receptors. Similarly, the broad-spectrum opiate antagonist naloxone has no appreciable affinity for ORL1.

Enkephalins have been observed to have effects on murine hematopoiesis in vivo under conditions of immobilization stress (Goldberg et al., Folia Biol. (Praha) 36:319–331, 1990). Leu-enkephalin inhibited and met-enkephalin stimulated bone marrow hematopoiesis. These effects were indirect, Goldberg et al. believed due to effects on glucocorticoid levels and T lymphocyte migration. Krizanac-Bengez et al. (Biomed. & Pharmacother. 46:367–43, 1992; Biomed. & Pharmacother. 49:27–31, 1995; Biomed. & Pharmacother. 50:85–91, 1996) looked at the effects of these compounds in vitro. Pre-treatment of murine bone marrow with Met- or Leu-enkephalin or naloxone affected the number of GM progenitor cells observed in a colony assay. This effect was highly variable and resulted in suppression, stimulation or no effect; further, there was no clear dose-response. This variability was ascribed by Krizanac-Bengez et al. to circadian rhythms and to accessory cells.

Recently, it has been demonstrated that mice in which the mu opiate receptor has been deleted by homologous recombination have elevated numbers of CFU-GM, BFU-E and CFU-GEMM per femur. Marrow and splenic progenitors were more rapidly cycling in these mu receptor knockout mice compared to normal mice. It was not determined if these effects were due to a direct or indirect effect on bone marrow stem cells resulting from the absence of the mu receptor in these animals (Broxmeyer et al., Blood 88:338a, 1997).

I. Chemotherapy and Radiotherapy of Cancer

Productive research on stimulatory growth factors has resulted in the clinical use of a number of these factors (erythropoietin, G-CSF, GM-CSF, etc.). These factors have reduced the mortality and morbidity associated with chemotherapeutic and radiation treatments. Further clinical benefits to patients who are undergoing chemotherapy or radiation could be realized by an alternative strategy of blocking entrance of stem cells into cell cycle thereby protecting them from toxic side effects. The reversal of this protection will allow for rapid recovery of bone marrow function subsequent to chemo- or radiotherapy.

II. Bone Marrow and Stem Cell Transplantation, Ex Vivo Stem Cell Expansion and Tumor Purging Bone marrow transplantation (BMT) is a useful treatment for a variety of hematological, autoimmune and malignant diseases. Current therapies include hematopoietic cells obtained from umbilical cord blood, fetal liver or from peripheral blood (either unmobilized or mobilized with agents such as G-CSF or cyclophosphamide) as well as from bone marrow; the stem cells may be unpurified, partially purified (e.g., affinity purification of the $CD34^+$ population) or highly purified (e.g., through fluorescent activated cell sorting using markers such as CD34, CD38 or rhodamine). Ex vivo manipulation of hematopoietic cells is currently being used to expand primitive stem cells to a population suitable for transplantation. Optimization of this procedure requires: (1) sufficient numbers of stem cells able to maintain long term reconstitution of hematopoiesis; (2) the depletion of graft versus host-inducing T-lymphocytes and (3) the absence of residual malignant cells. This procedure can be optimized by including a stem cell inhibitor(s) and/or a stem cell stimulator(s).

The effectiveness of purging of hematopoietic cells with cytotoxic drugs in order to eliminate residual malignant cells is limited due to the toxicity of these compounds for normal hematopoietic cells and especially stem cells. There is a need for effective protection of normal cells during purging; protection can be afforded by taking stem cells out of cycle with an effective inhibitor.

III. Peripheral Stem Cell Harvesting

Peripheral blood stem cells (PBSC) offer a number of potential advantages over bone marrow for autologous transplantation. Patients without suitable marrow harvest sites due to tumor involvement or previous radiotherapy can still undergo PBSC collections. The use of blood stem cells eliminates the need for general anesthesia and a surgical procedure in patients who would not tolerate this well. The apheresis technology necessary to collect blood cells is efficient and widely available at most major medical centers. The major limitations of the method are both the low normal steady state frequency of stem cells in peripheral blood and their high cycle status after mobilization procedures with drugs or growth factors (e.g., cyclophosphamide, G-CSF, stem cell factor). An effective stem cell inhibitor will be useful to return such cells to a quiescent state, thereby preventing their loss through differentiation.

IV. Treatment of Hyperproliferative Disorders

A number of diseases are characterized by a hyperproliferative state in which dysregulated stem cells give rise to an overproduction of end stage cells. Such disease states include, but are not restricted to, psoriasis, in which there is an overproduction of epidermal cells, premalignant conditions in the gastrointestinal tract characterized by the appearance of intestinal polyps, and acquired immune deficiency syndrome (AIDS) where early stem cells are not infected by HIV but cycle rapidly resulting in stem cell exhaustion. A stem cell inhibitor will be useful in the treatment of such conditions.

V. Treatment of Hypoproliferative Disorders

A number of diseases are characterized by a hypoproliferative state in which dysregulated stem cells give rise to an underproduction of end stage cells. Such disease states include myelodysplatic syndromes or aplastic anemia, in which there is an underproduction of blood cells, and conditions associated with aging where there is a deficiency in cellular regeneration and replacement A stem cell stimulator will be useful in the treatment of such conditions.

VI. Gene Transfer

The ability to transfer genetic information into hematopoietic cells is currently being utilized in clinical settings. Hematopoietic cells are a useful target for gene therapy because of ease of access, extensive experience in manipulating and treating this tissue ex vivo and because of the ability of blood cells to permeate tissues. Furthermore, the correction of certain human genetic defects can be possible by the insertion of a functional gene into the primitive stem cells of the human hematopoietic system.

There are several limitations for the introduction of genes into human hematopoietic cells using either retrovirus vectors or physical techniques of gene transfer: (1) The low frequency of stem cells in hematopoietic tissues has necessitated the development of high efficiency gene transfer techniques; and (2) more rapidly cycling stem cells proved to be more susceptible to vector infection, but the increase of the infection frequency by stimulation of stem cell proliferation with growth factors produces negative effects on long term gene expression, because cells containing the transgenes are forced to differentiate irreversibly and lose their self-renewal. These problems can be ameliorated by the use of a stem cell inhibitor to prevent differentiation and loss of self-renewal and a stem cell stimulator to regulate the entry of stem cells into cycle and thereby facilitate retroviral-mediated gene transfer.

SUMMARY OF THE INVENTION

The present invention relates to compounds including peptides and polypeptides which are inhibitors and/or stimulators of stem cell proliferation (INPROL and opiate compounds) and their use.

The present invention includes an inhibitor of stem cell proliferation characterized by the following properties:

(a) Specific activity ($IC_{50}$) less than or equal to 20 ng/ml in a murine colony-forming spleen (CFU-S) assay (see Example 4), (b) Molecular weight greater than 10,000 and less than 100,000 daltons (by ultrafiltration), (c) Activity sensitive to degradation by trypsin, (d) More hydrophobic than MIP-1α or TGFβ and separable from both by reverse phase chromatography (see Example 12), (e) Biological activity retained after heating for one hour at 37° C., 55° C. or 75° C. in aqueous solution and (f) Biological activity retained after precipitation with 1% hydrochloric acid in acetone.

The present invention is further characterized and distinguished from other candidate stem cell inhibitors (e.g., MIP-1α, TGFβ and various oligopeptides) by its capacity to achieve inhibition in an in vitro assay after a short preincubation period (see Example 5).

The present invention also comprises pharmaceutical compositions containing INPROL for treatment of a variety of disorders.

The present invention provides a method of treating a subject anticipating exposure to an agent capable of killing or damaging stem cells by administering to that subject an effective amount of a stem cell inhibitory composition. The stem cells protected by this method can be hematopoietic stem cells ordinarily present and dividing in the bone marrow, cord blood, fetal liver or mobilized into the peripheral blood circulation. While the majority of mobilized stem cells are quiescent according to fluorescence activated cell sorter (FACS) analysis, the multipotential stem cells are demonstrated to be cycling and inhibitable by INPROL at stem cell inhibitory amounts. Alternatively, stem cells can be epithelial, located for example, in the intestines or scalp or other areas of the body or germ cells located in reproductive organs. The method of this invention can be desirably employed on humans, although animal treatment is also encompassed by this method. As used herein, the terms "subject" or "patient" refer to an animal, such as a mammal, including a human.

The present invention also provides a method of treating a subject with hypoproliferating stem cells by administering to that subject an effective amount of a stem cell stimulatory composition. The stem cells stimulated by this method can be hematopoietic stem cells ordinarily present in the bone marrow, cord blood, fetal liver or mobilized into the peripheral blood circulation; such stem cells may have previously been placed into quiescence by use of INPROL at stem cell inhibitory amounts. INPROL at stem cell stimulatory amounts will allow for stimulation of stem cell cycling when desired—for example, after harvesting of stem cells for use during ex vivo expansion, or in vivo subsequent to stem cell transplantation and engraftment. Alternatively, stem cells can be epithelial, located for example, in the intestines, or scalp or other areas of the body or germ cells located in reproductive organs.

In another aspect, the invention provides a method for protecting and restoring the hematopoietic, immune or other stem cell systems of a patient undergoing chemotherapy, which includes administering to the patient an effective stem cell inhibitory amount of INPROL and/or to stimulate recovery after chemotherapy or radiation by administering an effective stem cell stimulatory amount of INPROL.

In still a further aspect, the present invention involves a method for adjunctively treating any cancer, including those characterized by solid tumors (e.g., breast, colon, lung, testicular, ovarian, liver, kidney, pancreas, brain, sarcoma), by administering to a patient having cancer an effective stem cell inhibitory amount of INPROL to protect stem cells of the bone marrow, gastrointestinal tract or other organs from the toxic effects of chemotherapy or radiation therapy and/or to stimulate recovery after chemotherapy or radiation therapy by administering stem cell stimulatory amounts of INPROL.

Yet another aspect of the present invention involves the treatment of leukemia (e.g., chronic myelogenous leukemia, acute myelogenous leukemia, chronic lymphocytic leukemia, acute lymphocytic leukemia, myeloma, Hodgkin's disease), comprising treating hematopoietic cells having proliferating leukemia cells therein with an effective amount of INPROL to inhibit proliferation of normal stem cells, and treating the bone marrow with a cytotoxic agent to destroy leukemia cells. This method can be enhanced by the follow-up treatment of the bone marrow with other agents that stimulate its proliferation; e.g. colony stimulating factors and/or INPROL at stem cell stimulatory amounts. In one embodiment this method is performed in vivo. Alternatively, this method is also useful for ex vivo purging and expansion of hematopoietic cells for transplantation.

In still a further aspect, the method involves treating a subject having any disorder caused by proliferating stem cells. Such disorders, such as psoriasis, myelodysplasia, some autoimmune diseases, immuno-depression in aging, myelodysplastic syndrome, aplastic anemia or stem cell exhaustion in AIDS are treated by administering to the subject an effective amount of INPROL to inhibit or to stimulate proliferation of the stem cell in question.

The present invention provides a method for reversibly protecting stem cells from damage from a cytotoxic agent capable of killing or damaging stem cells. The method involves administering to a subject anticipating exposure to such an agent an effective stem cell inhibitory amount of INPROL.

The present invention also provides a method for reversibly stimulating the proliferation of stem cells during the recovery phase after chemotherapy or radiation. The method involves administering to a subject anticipating exposure to such an agent, an effective stem cell stimulatory amount of INPROL.

The present invention also provides:

An inhibitor of stem cell proliferation isolated from porcine or other bone marrow by the following procedure (see Example 12):

(a) Extraction of bone marrow and removal of particulate matter through filtration, (b) Heat treatment at 56° C. for 40 minutes followed by cooling in ice bath, (c) Removal of precipitate by centrifugation at 10,000 g for 30 minutes at 4° C., (d) Acid precipitation by addition of supernatant to 10 volumes of stirred ice-cold acetone containing 1% by volume concentrated hydrochloric acid and incubation at 4° C. for 16 hours, (e) Isolation of precipitate by centrifugation at 20,000 g for 30 minutes at 4° C. and washing with cold acetone followed by drying, (f) Isolation by reverse phase chromatography and monitoring activity by inhibition of colony formation by bone marrow cells pretreated with 5-fluorouracil and incubated in the presence of murine IL-3, as well as by absorption at 280 nm and by SDS-PAGE.

The present invention also provides:

A method for purifying an inhibitor of stem cell proliferation substantially free from other proteinaceous materials comprising the preceding steps, as also described in more detail below.

The present invention also provides:

A method of treatment for humans or animals wherein an inhibitor of stem cell proliferation functions to ameliorate immunosuppression caused by stem cell hyperproliferation.

The present invention also provides:

A method of treatment for humans or animals wherein INPROL at stem cell stimulatory amounts ameliorates bone marrow suppression caused by stem cell hypoproliferation.

The present invention also provides:

A method of treatment for humans or animals wherein said inhibitor of stem cell proliferation is administered after the stem cells are induced to proliferate by exposure to a cytotoxic drug or irradiation procedure. Stem cells are normally quiescent but are stimulated to enter cell cycle after chemotherapy. This renders them more sensitive to a second administration of chemotherapy; the current method protects them from this treatment.

The present invention also provides:

A method of treatment for humans or animals wherein a stimulator of stem cell proliferation (e.g., INPROL at stem cell stimulatory amounts) is administered, before or after INPROL at stem cell inhibitory amounts, to promote bone marrow regeneration. Stem cell inhibitory amounts of INPROL slow the rate at which stem cells transit the cell cycle and protect against chemotherapy or radiation; stem cell stimulatory amounts of INPROL reverse this inhibition and promote bone marrow recovery. Conversely, stem cell stimulatory amounts of INPROL can be used to promote bone marrow recovery while stem cell inhibitory amounts are used subsequently to return stem cells to quiescence once bone marrow recovery is achieved.

The present invention also provides:

A method of treatment for humans or animals wherein said inhibitor of stem cell proliferation is administered as an adjuvant before or together with vaccination for the purpose of increasing immune response.

The present invention also provides:

A method of treating immune deficiency in a mammal comprising administering to said mammal an immunostimulatory amount of INPROL.

The present invention also provides:

A method of treating pain in a mammal comprising administering to said mammal an analgesia-inducing amount of INPROL.

The present invention also provides:

A method of treatment for humans or animals receiving cytotoxic drugs or radiation treatment which comprises administering an effective amount of the inhibitor of stem cell proliferation to protect stem cells against damage.

The present invention also provides:

A method of treatment for humans or animals receiving cytotoxic drugs or radiation treatment which comprises administering an effective stem cell stimulatory amount of INPROL to enhance recovery after treatment.

The invention also includes a pharmaceutical composition comprising hemoglobin and a pharmaceutically acceptable carrier.

The invention also includes a pharmaceutical composition comprising (a) a polypeptide selected from the group consisting of the alpha chain of hemoglobin, the beta chain of hemoglobin, the gamma chain of hemoglobin, the delta chain of hemoglobin, the epsilon chain of hemoglobin and the zeta chain of hemoglobin, the polypeptide comprising amino acids 1–97 of the human alpha hemoglobin chain ("peptide 1–97") and the polypeptide comprising amino acids 1–94 of the human alpha hemoglobin chain ("peptide 1–94") and (b) a pharmaceutically acceptable carrier. Such pharmaceutical compositions be can composed of a single polypeptide selected from said group, a mixture of polypeptides selected from said group or polypeptides from said group in the form of dimers or multimers, with or without heme.

The invention also includes peptides having the sequences: Phe-Pro-His-Phe-Asp-Leu-Ser-His-Gly-Ser-Ala-Gln-Val ("Peptide 43–55"), Cys-Phe-Pro-His-Phe-Asp-Leu-Ser-His-Gly-Ser-Ala-Gln-Val-Cys where the two Cys residues form a disulfide bond ("Cyclic Peptide 43–55"), Cys-Phe-Pro-His-Phe-Asp-Leu-Ser-His-Gly-Ser-Ala-Gln-Val-Cys where the two Cys residues are joined by a carbon bridge, Asp-Ala-Leu-Thr-Asn-Ala-Val-Ala-His-Val-Asp-Asp-Met-Pro-Asn-Ala-Leu-Ser-Ala ("Peptide 64–82"), and a peptide comprising the first 97 N-terminal amino acids of human alpha hemoglobin as in FIG. 16A.

Also included in the invention are proteins and peptide sequences consisting of modified versions of the human alpha chain which retain stem cell inhibitory and/or stimulatory properties. Such modifications include, but are not limited to, removal or modification of the C-terminal hydrophobic domain (resulting in improved solubility characteristics) and/or removal or modification of the haptoglobin binding domain (resulting in improved pharmacokinetic properties). The C-terminal hydrophobic domain in human alpha hemoglobin is comprised of the region from amino acids 98 (phenylalanine) to 141 (arginine) and contains 23 hydrophobic amino acids out of a total of 44. The entire domain or one or more of these hydrophobic amino acids (6 alanines, 4 valines, 8 leucines, 2 proline and 3 phenylalanines) can be removed by deletion ("deleted" C-terminal hydrophobic domain). Alternatively, one or more of these amino acids can be substituted with a non-polar amino acid (e.g., glycine, serine, threonine, cysteine, tyrosine, asparagine or glutamine) ("substituted" C-terminal hydrophobic domain).

In another embodiment, chemical modifications such as carboxymethylation, which decrease the hydrophobic character of this region and increases solubility, is used.

In another embodiment, hydrophobic residues are substituted with the corresponding hydrophilic regions in the human beta hemoglobin sequence. For example, in the human beta hemoglobin sequence, the region between amino acids 107 (glycine) to 117 (histidine) or the region between amino acids 130 (tyrosine) to 139 (asparagine) are each relatively hydrophilic and each or both can be substituted for the equivalent hydrophobic regions in human alpha hemoglobin.

The haptoglobin binding domain is contained within the C-terminal hydrophobic region and is comprised of amino acids 121–127. This region can be removed by deletion in its entirety or one or more amino acids in this region can be deleted ("deleted" C-terminal haptoglobin binding domain). This region or one or more amino acids in this region can be substituted with other amino acids such as, for example, poly-alanine or poly-glycine or other amino acids which have the effect of abolishing the binding of the polypeptide to haptoglobin but maintain the stem cell inhibitory activity ("substituted" C-terminal haptoglobin binding domain).

Other embodiments of the invention encompass corresponding modifications to the beta hemoglobin chain (either in the C-terminal hydrophobic region and/or in one or both haptoglobin binding domains (amino acids 11–25 and 136–146)), and corresponding modifications to the delta, gamma, epsilon and/or zeta hemoglobin chains.

Also included in the invention are DNA sequences encoding the above identified peptides, vectors containing said DNA sequences and host cells containing said vectors. These peptides can be synthesized using standard chemical techniques (e.g., solid phase synthesis) or by using recombinant techniques (including fusion systems such as those employing glutathione-S-transferase (D. B. Smith and K. S. Johnson, Gene 67:31–40, 1988), thioredoxin (LaVallie et al., Biotechnology 11: 187–193, 1993) or ubiquitin (Butt et al., PNAS 86:2540–4, 1989; Cherney et al., Biochem. 30: 10420–7, 1991; Baker et al., JBC 269:25381–6, 1994; U.S. Pat. Nos. 5,132,213; 5,196,321 and 5,391,490 and PCT WO 91/17245). Each of these articles, applications and patents is hereby incorporated by reference.

Additionally the invention includes a method of inhibiting or stimulating stem cell proliferation comprising contacting hematopoietic cells with a compound capable of binding opiate receptors, advantageously the mu subclass of opiate receptors. Additionally the invention includes a method of inhibiting or stimulating stem cell proliferation comprising contacting hematopoietic cells with a compound capable of binding nociceptin receptors (e.g., ORL1). Further, the invention includes a method of inhibiting or stimulating stem cell proliferation comprising contacting hematopoietic cells with a compound capable of binding "opiate-like" receptors.

Peptides (called "hemorphins") have been isolated from hemoglobin which exhibit opiate activities (e.g., Brantl et al., Eur. J. Pharm, 125:309–10, 1986; Davis et al. Peptides 10:747–51, 1989; Hoffman et al., PNAS 87:8521–25, 1990; Hernan et al., Biochem. 31:8619–28, 1992; Karelin et al. Bioch. Biophys. Res. Comm, 202:410–5, 1994; Zhao et al., Ann. N.Y. Acad. Science 750:452–8, 1995: Petrov et al., Bioscience Reports, 15:1–14, 1995; Karelin et al., Peptides 16:693–697, 1995). Each of these articles is hereby incorporated by reference. Other a typical opiate peptides and small molecules also exist (Zioudrou et al., JBC 254: 2446–9, 1979; Quirion and Weiss, Peptides 4:445, 1983; Loukas et al., Biochem. 22:4567, 1983; Brantl, Eur. J. Pharm. 106:213–14, 1984; Brantl et al., Eur. J. Pharm. 111:293–4, 1985; Brantl and Neubert, TIPS 7:6–7,1986; Hruby and Gehrig, Med. Res. Rev. 9:343–401, 1989; Schiller, Prog. Med. Chem. 28: 301–40, 1991; Glamsta et al., BBRC 184:1060–6, 1992; Teschemacher, Handbook Exp. Pharm. 104:499–28, 1993; Handbook of Experimental Pharmacology, A. Hertz (Ed.) volumes 104/I and 104/II, 1993, Springer Verlag, Berlin; Reed et al., Neurosci. and Biobehav. Rev. 18:519–25, 1994; Karelin et al., Peptides 16:693–7, 1995). Each of these articles is hereby incorporated by reference. As used herein, "opiate-like receptors" are defined by their ability to bind opiates, INPROL, hemorphins, exorphins, nociceptin, Tyr-MIF-1 family members, alkaloids and/or other compounds which either inhibit or stimulate stem cell proliferation in a manner antagonized by the inclusion of an appropriate amount of naloxone (see Examples 29 and 38).

In addition, the invention includes a method of identifying receptor(s) and ligands comprising using INPROL (advantageously peptide forms such as Peptide 1–94, 1–97, 43–55 or 64–82) in a receptor binding assay. Further, the invention includes a method of identifying receptor(s) and ligands comprising using INPROL in an adenylate cyclase assay.

Additionally the invention includes a method of inhibiting or stimulating stem cell proliferation comprising contacting hematopoietic cells with a compound (for example, mastoparan) capable of activating GTP-binding proteins, advantageously those of the Ginhibitory subtype.

The invention also includes a method of inhibiting or stimulating stem cell proliferation comprising contacting hematopoietic cells with a peptide selected from the group of hemorphin peptides having the sequence:
Leu-Val-Val-Tyr-Pro-Trp-Thr-Gln-Arg-Phe,
Leu-Val-Val-Tyr-Pro-Trp-Thr-Gln-Arg.
Leu-Val-Val-Tyr-Pro-Trp-Thr-Gln,
Leu-Val-Val-Tyr-Pro-Trp-Thr,
Leu-Val-Val-Tyr-Pro-Trp,
Leu-Val-Val-Tyr-Pro,
Val-Val-Tyr-Pro-Trp-Thr-Gln,
Tyr-Pro-Trp-Thr-Gln-Arg-Phe,
Tyr-Pro-Trp-Thr-Gln-Arg,
Tyr-Pro-Trp-Thr-Gln, and
Tyr-Pro-Trp-Thr.

The above peptides have sequence similarity and/or biological activity similar to other a typical opiate peptides such as those of the Tyr-MIF-1 family (see Reed et al., Neurosci. Biobehav. Rev. 18:519–25, 1994 for review), the casein-derived casomorphins (Brantl et al., Hoppe-Seyler's Z. Physiol. Chem. 360:1211–16, 1979; Loukas et al., Biochem. 22:4567–4573, 1983; Fiat and Jolles, Mol. Cell. Biochem. 87:5–30, 1989), peptides derived from cytochrome b, termed cytochrophins (Brantl et al., Eur. J. Pharm. 111:293–4, 1985), various exorphins and opiate peptides from human and non-human species (Zioudrou et al., JBC 254: 2446–9, 1979; Brantl, Eur. J. Pharm. 106:213–14, 1984; Brantl et al., Eur. J. Pharm. 125:309–10, 1986; Brantl and Neubert, TIPS 7:6–7,1986; Glamsta et al., BBRC 184: 1060–6, 1992; Teschemacher, Handbook Exp. Pharm. 104: 499–28, 1993; Karelin et al., Peptides 16:693–7, 1995) as well as to peptides derived from combinatorial libraries screened for binding to opiate receptors (see Dooley et al., Peptide Research 8:124–137, 1995 for review). Each of these articles is hereby incorporated by reference.

The invention also includes a method of inhibiting or stimulating stem cell proliferation comprising contacting hematopoietic cells with a peptide selected from the group consisting of Tyr-MIF-1 related peptides, casomorphins, cytochrophins and exorphins. Specifically included are the Tyr-MIF-1 peptides having the sequences:
Tyr-Pro-Try-Gly-NI-12,
Tyr-Pro-Lys-Gly-NH2,
Tyr-Pro-Leu-Gly-NH2, and
Pro-Leu-Gly-NH2.

The invention also includes a method of inhibiting or stimulating stem cell proliferation comprising contacting hematopoietic cells with an opiate peptide selected from the group consisting of
(D-Ala$^2$,N-Me-Phe$^4$,Gly-ol$^5$)-Enkephalin (DAMGO),
(D-Arg$^2$,Lys$^4$)-Dermorphin-(1-4)-amide (DALDA),
(Phe$^4$)-Dermorphine (1-4) amide
Ac-Arg-Phe-Met-Trp-Met-Arg-NH$_2$,
Ac-Arg-Phe-Met-Trp-Met-Lys-NH$_2$, and
H-Tyr-Gly-Gly-Phe-Met-Arg-Arg-Val-NH$_2$.

The invention also includes a method of inhibiting or stimulating stem cell proliferation comprising contacting hematopoietic cells with an opiate agonist compound selected from the group consisting of morphine, codeine, methadone, heroin, meperidine, alphaprodine, diphenoxylate, fentanyl, sufentanil, alfentanil, levorphanol, hydrocodone, dihydrocodeine, oxycodone, hydromorphone, propoxyphene, buprenorphine, etorphine, oxymorphone dextropropoxyphene, and meptazinol. Specifically included is morphine at inhibitory amounts less than $10^{-7}$ molar.

The invention also includes a method of inhibiting or stimulating stem cell proliferation comprising contacting hematopoietic cells with an opiate antagonist or mixed agonist/antagonist selected from the group consisting of naloxone, naltrexone, nalorphine, pentazocine, nalbuphine and butorphanol. Specifically included is naloxone at inhibitory amounts of less than $10^{-8}$ molar.

The invention also includes a method of stimulating stem cell proliferation comprising contacting hematopoietic cells with a stem cell stimulating amount of protein or peptide selected from the group that includes INPROL, myoglobin, DAMGO and DALDA.

The invention also includes a method of conducting gene therapy in a mammal comprising:

a) removing hematopoietic cells from said mammal,
b) treating said hematopoietic cells ex vivo with a stem cell stimulatory amount of INPROL and/or an opiate compound,
c) transfecting or infecting said hematopoietic cells with a predetermined gene,
d) contacting said transfected hematopoietic cells ex vivo with a stem cell inhibitory amount of INPROL and/or an opiate compound,
e) transplanting into said mammal the hematopoietic cells of step d
f) optionally treating said mammal in vivo with a stem cell inhibitory or stimulatory quantity INPROL and/or an opiate compound.

The invention also includes a method of conducting ex vivo stem cell expansion comprising treating said hematopoietic cells with stem cell inhibitory amounts of INPROL and at least one stimulatory cytokine. INPROL is contacted with the hematopoietic cells before, during and/or after contact with the stimulatory cytokine. Ex vivo stem cell expansion allows the production of sufficient amounts of stem cells from limiting sources such as cord blood, fetal liver, autologous bone marrow after chemotherapy, etc. or after purification (e.g., through fluorescent activated cell sorting using markers such as CD34, CD38 or rhodamine). The ability to selectively grow particular hematopoietic lineages also allows the clinician to specifically design stem cell transplants according to the needs of an individual patient.

The invention also includes a method of conducting ex vivo stem cell expansion comprising treating hematopoietic cells with stem cell stimulatory amounts of INPROL with or without at least one additional stimulatory cytokine. INPROL is contacted with the hematopoietic cells before, during and/or after contact with the stimulatory cytokine(s). Ex vivo, a stem cell stimulator will allow for expansion of stem cells and/or progenitors while a stem cell inhibitor will maintain stem cells in their undifferentiated state. The procedure can also be optimized by the use of INPROL at stem cell inhibitory amounts in vivo to maintain stem cells in a quiescent state until they are engrafted, after which INPROL at stem cell stimulatory amounts can be used to stimulate bone marrow regeneration. Optionally, the hematopoietic cells may be split into two preparations and one treated with stem cell stimulatory amounts of INPROL to promote expansion of stem cells and/or progenitors while the other is treated with stem cell inhibitory amounts of INPROL to maintain stem cells in their undifferentiated state. The two preparations can then be combined and infused into a patient.

The invention also includes a pharmaceutical composition comprising (a) INPROL and (b) at least one inhibitory compound selected from the group consisting of MIP-1α, TGFβ, TNFα, INFα, INFβ, INFγ, the pentapeptide pyro-Glu-Glu-Asp-Cys-Lys, the tetrapeptide N-Acetyl-Ser-Asp-Lys-Pro, and the tripeptide glutathione (Gly-Cys-γGlu).

The invention also includes a pharmaceutical composition comprising (a) INPROL and (b) at least one stimulatory cytokine selected from the group consisting of IL-1, IL-2, IL-3, IL-4, IL-5, IL-6, IL-7, IL-9, IL-11, IL-13, IL-14, IL-15, G-CSF, GM-CSF, M-CS, erythropoietin, thrombopoietin, stem cell factor, delta-like protein and flk2/flt3 ligand.

The current invention describes an inhibitor of stem cells (INPROL) which is different from those known in the art such as MIP-1α, TGFβ, the tetrapeptide of Frindel and colleagues or the pentapeptide of Paukovits and coworkers (cf., Wright & Pragnell, 1992 (op. Cit.)). Naturally occuring native INPROL has a molecular weight exceeding 10,000 daltons by ultrafiltration which distinguishes it from the tetrapeptide as well as the pentapeptide. It is more hydrophobic than MIP-1α or TGFβ in reverse phase chromatography systems, distinguishing it from those cytokines. Further, its mode of action is different from that of any previously described inhibitor in that it is active in an in vitro assay when used during a preincubation period only. MIP-1α for example, is not effective when used during a preincubation period only (Example 5). Further, naturally occuring INPROL is active in an assay measuring "high proliferative potential cells" (HPP-PFC) whereas MIP-1α is not (Example 6). INPROL is different from those stimulators known in the art such as IL-1, IL-2, IL-3, IL-4, IL-5, IL-6, IL-7, IL-9, IL-10, IL-11, IL-12, IL-13, IL-14, IL-15, L-16, G-CSF, GM-CSF, M-CSF, erythropoietin, thrombopoietin, stem cell factor, and flk2/flt3 ligand. Naturally occuring INPROL has little or no sequence similarity to these cytokines.

BRIEF DESCRIPTION OF THE DRAWINGS

FIG. 1—Lane 1 is chymotrypsinogen, Lane 2 is ovalbumin, Lane 3 is BSA, Lane 4 is fractions <30 kD, Lane 5 is fractions 30–50 kD and Lane 6 is fractions 50–100 kD.

FIG. 2—Lane 1 is after ammonium sulfate precipitation (40–80%) and lanes 2–5 are DEAE fractions (Lane #2 represents the active fraction).

FIG. 3—Lane 1 is the supernatant after ammonium sulfate precipitation, Lane 2 is the active DEAE fraction, Lanes 3–5 represent gel filtration fractions (lane #5 represents the active fraction)

FIG. 4—Lane 2 represents the final product.

FIG. 16 shows hemoglobin sequences: FIG. 16A shows the cDNA and amino acid sequences of human alpha hemoglobin and FIG. 16B shows the cDNA and amino acid sequences of human beta hemoglobin. Numbering is according to the amino acid. FIG. 16C shows an amino acid sequence comparison of the alpha and beta chains of human, murine and porcine hemoglobins.

Figure 1:
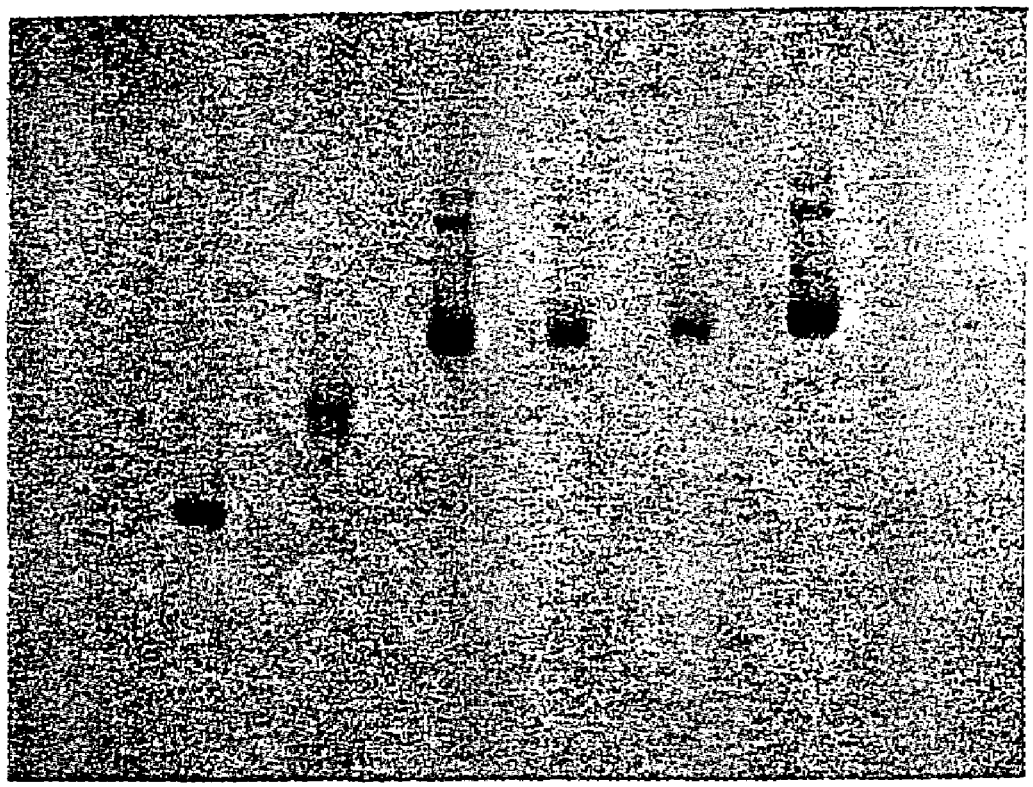
FIGS. 1–4 show an SDS polyacrylamide gel run of the product after each stage of purification.

In order that the invention herein described may be more fully understood, the following detailed description is set forth. This description, while exemplary of the present invention, is not to be construed as specifically limiting the invention and such variations which would be within the purview of one skilled in this art are to be considered to fall within the scope of this invention.

DETAILED DESCRIPTION OF THE PREFERRED EMBODIMENTS

INPROL reversibly inhibits or stimulates division of stem cells. While not wishing to be bound to a specific theory, stem cell inhibitors and stimulators are thought to exert their effects by influencing the rate at which stem cells transit through the cell cycle. Specifically, INPROL is effective in temporarily inhibiting or stimulating cell division of hematopoietic stem cells depending on the amount used. The ability to use a compound clinically which can inhibit or stimulate stem cell proliferation allows for exquisite control of the cycling of hematopoietic stem cells during, for example, chemotherapy, stem cell transplantation or gene therapy protocols. Thus, the method of this invention can be employed in alleviating the undesirable side effects of chemotherapy on the patient's hematopoietic, myeloid and immune systems by protecting stem cells from damage caused by chemotherapeutic agents or radiation used to destroy cancer or virally infected cells or by stimulating recovery after such damage. In one embodiment of the invention, INPROL is administered to the patient in a dosage sufficient to inhibit stem cell division while the chemotherapeutic agent acts on diseased cells. After the chemotherapeutic agent has performed its function, the stem cells inhibited by INPROL will, without further treatment, revert to dividing cells. If it is desired to enhance the regeneration of hematopoiesis, stimulatory growth factors, cytokines or stem cell stimulatory amounts of INPROL can be used in addition.

As used herein, the term "INPROL" includes mammalian and non-mammalian proteins, purified as in the Examples, hemoglobin, the alpha chain of hemoglobin (with or without the heme group), the beta chain of hemoglobin (with or without the heme group), mixtures of alpha and beta chains (with or without the heme group), and fragments or analogs of these proteins including embryonic, fetal or adult forms (e.g., alpha, beta, gamma, delta, epsilon or zeta chains, either alone or as mixtures, dimers or multimers, with or without the heme group) having the ability to inhibit and/or stimulate stem cell proliferation. The term "INPROL" includes naturally occurring as well as non-naturally occurring (e.g., recombinantly and/or synthetically produced) forms of these proteins. The term "INPROL polypeptide" refers to INPROL consisting of 40 or more amino acids.

As used herein, the term "opiate compounds" are compounds, including opiates but not INPROL, which bind to opiate receptors (or to receptors bearing sequence relatedness to opiate receptors, e.g., ORL1) and exert either agonist, antagonist or mixed agonist/antagonist activities. For example, specific agonists and antagonists exist for mu receptors (which are selectively activated by DAMGO and DALDA and selectively antagonized by CTOP and naloxonazine), for kappa receptors (which are selectively activated by GR 89696 fumarate or U-69593 and selectively antagonized by nor—binaltorphimine hydrochloride) and for delta receptors (which are selectively activated by DADLE and DPDPE and selectively antagonized by natrindole). In addition, there are broad-spectrum antagonists (such as naloxone) and agonists (such as etorphine) which act on all three receptor subtypes. Nociceptin specifically agonizes the ORL1 receptor. Opiate compounds with stem cell stimulatory and/or inhibitory activities can be used for each of the applications described herein for INPROL.

As used herein, "stem cell stimulatory amount" is that amount which induces proliferation of stem cells. As used herein, "stem cell inhibitory amount" is that amount which inhibits proliferation of stem cells. In all cases, both in vivo and ex vivo, the amount selected will depend upon the specific INPROL or opiate compound selected and the specific condition or application; in particular, equimolar doses of polypeptides or fragments of INPROL are active as are equimolar opiate peptides or small molecules.

In a typical clinical situation, where stem cell inhibition is desired, INPROL is administered to a patient in a daily regimen by intravenous injection or infusion in dosage unit form using, for example, 0.01 to 100 mg/kg, advantageously 0.1 to 1.0 mg/kg, of INPROL administered, e.g., 4 to 60 hours prior to standard chemotherapy or radiation treatments when it is desirable to inhibit stem cell cycling.

In situations where stimulation of stem cell cycling is desirable, such as to promote recovery after chemotherapy or radiation, INPROL at stem cell stimulatory amounts are used. Such doses are typically 1–500 mg/kg, advantageously 10 mg to 100 mg/kg.

In cases where it is desirable to use opiate compound(s) to inhibit or to stimulate stem cell cycling, the opiate compound(s) are used at equimolar concentrations to that described for INPROL.

In another embodiment of the invention, pretreatment with INPROL at stem cell inhibitory amounts allows for increased doses of chemotherapeutic agents or of radiation beyond doses normally tolerated in patients. Similarly, post-chemotherapy or post-radiation treatment with INPROL at stem cell stimulatory amounts also allows for increases in normally tolerated doses of chemotherapy or radiation.

A large fraction of hematopoietic stem cells are normally quiescent (slowly or non-cycling). However, as a compensatory response to chemotherapy-induced hematopoietic damage, a larger proportion of stem cells enter into cycling after chemotherapy, which makes them particularly vulnerable to subsequent doses of cytotoxic chemotherapy or therapeutic irradiation. By inhibiting cycling of such stem cells, INPROL treatment permits earlier or more frequent administration of subsequent doses of cytotoxic chemotherapy, either at conventional or elevated doses.

Some normal individuals have stem cells that spontaneously cycle rapidly; INPROL at stem cell inhibitory amounts is useful in such individuals even if given prior to the first dose of radiation or chemotherapy.

In one embodiment of the invention, INPROL (0.1 mgs. to 6 gms/kg body weight—advantageously 1.0 to 60 mgs./kg) is administered about 24 hours to 10 days after an initial dose of chemotherapy. After another 4 to 60 hours, advantageously 24 to 48 hours, another dose of chemotherapy is administered. This cycle of alternating chemotherapy and INPROL is continued according to therapeutic benefit. Chemotherapy agents and protocols for administration are selected according to suitability for particular tumor types in standard clinical practice. Optionally, stimulatory growth factors such as G-CSF, stem cell factor, or INPROL at stem cell stimulatory amounts is used after chemotherapy or radiation treatment to further improve hematopoietic reconstitution.

For ex vivo applications 0.1 ng to 100 ng/$10^6$ cells/ml, advantageously 2–50 ng/$10^6$ cells/ml, of INPROL are used in cases where inhibition of stem cell proliferation is desired. For cases where stem cell stimulation is desired, 10 ng–100 μg/$10^6$ cells/ml, advantageously 1–100 μg/$10^6$ cells/ml, of INPROL are used.

In cases where it is desirable to use opiate compound(s) to inhibit or stimulate stem cell cycling, the opiate compound(s) are used at equimolar concentrations to that described for INPROL.

In another embodiment of the invention, INPROL is employed in a method for preparing autologous hematopoietic cells for transplantation. The hematopoietic cells are treated ex vivo with an effective amount of INPROL to inhibit stem cell division and then purged of cancerous cells by administering to the marrow cultures an effective amount of a chemotherapeutic agent or radiation. Chemotherapy agents with specificity for cycling cells are preferred. Marrow thus treated is reinjected into the autologous donor. Optionally, the patient is treated with stem cell stimulatory amounts of INPROL and/or another agent known to stimulate hematopoiesis to improve the hematopoietic reconstitution of the patient. Such a technique allows for effective purging of tumor cells during autologous bone marrow grafts while protecting hematopoietic stem cells. Such protection can be afforded with either ex vivo or in vivo purging protocols. Once successfully transplanted, there is a need for stem cells to rapidly proliferate to regenerate normal bone marrow function. This can be afforded by the use of INPROL at stem cell stimulatory amounts which stimulates cycling of stem cells and enhances recovery of bone marrow function.

In another embodiment of the invention, INPROL is employed in a method for preparing hematopoietic cells for gene therapy. The hematopoietic cells are treated ex vivo with INPROL at stem cell stimulatory amounts and/or other stimulatory cytokine(s) to stimulate stem cell division, and then transfected (advantageously infected using e.g. a retroviral vector) with the gene(s) of interest. After transfection has been achieved, cells are washed and treated with INPROL at stem cell inhibitory amounts to return stem cells to quiescence. Marrow thus treated is reinjected into the donor. Optionally, the patient is treated in vivo with INPROL at stem cell inhibitory amounts to maintain stem cells in their quiescent form and to increase their marrow repopulating ability.

In another embodiment of the invention, INPROL is employed as an adjunctive therapy in the treatment of leukemia. For example, in disease states where the leukemic cells do not respond to INPROL, the hematopoietic cells are treated ex vivo with INPROL at stem cell inhibitory amounts. The proliferation of normal stem cells is prevented by administration of INPROL. Thus, during the time that the proliferating leukemic cells are treated with a cell cycle-specific cytotoxic agent, a population of normal stem cells is protected from damage. Additionally, a stimulatory cytokine, such as IL-3, GM-CSF, is optionally administered to induce cycling in the leukemic cells during drug or radiation treatment while the normal stem cells are protected with INPROL. The patient is treated with chemotherapy agents or radiation to destroy leukemic cells, and the purged marrow is then transplanted back into the patient to establish hematopoietic reconstitution.

Similarly, in another embodiment of the invention for treatment of patients with serious viral infections that involve blood cells or lymphocytes, such as HIV infection, hematopoietic cells are treated ex vivo or in vivo with INPROL followed by antiviral agents, drugs which destroy infected cells, or antibody-based systems for removing infected cells. Following myeloablative antiviral or myeloablative chemotherapy to eradicate viral host cells from the patient, the INPROL-treated marrow cells are returned to the patient.

In another embodiment of the invention, INPROL is employed to treat disorders related to hyperproliferative stem cells. For example, psoriasis is a disorder caused by hyperproliferating epithelial cells of the skin and is sometimes treated with cytotoxic drugs. Other pre-neoplastic lesions in which stem cell proliferation is involved are also amenable to effective amounts of INPROL employed to inhibit the proliferation of the stem cells. Patients with acquired immune deficiency syndrome have abnormally high rates of stem cell cycling resulting in stem cell exhaustion; these patients also benefit from treatment with effective amounts of INPROL to inhibit stem cell cycling. For these uses, topical or transdermal delivery compositions (e.g., ointments. lotions, gels or patches) containing INPROL are employed where appropriate, as an alternative to parenteral administration.

In most cases of leukemia, the leukemia progenitors are differentiated cell populations which are not affected by INPROL and which are therefore treated by methods using INPROL such as those described above. In cases where leukemia progenitors are very primitive and are directly sensitive to inhibition by INPROL, proliferation of leukemia cells is attenuated by administration of effective amounts of INPROL.

In another embodiment of the invention, INPROL is employed to treat disorders related to hypoproliferative stem cells. For example, myelodysplasic syndromes and aplastic anemia are disorders caused by hypoproliferating stem cells of the bone marrow. Other syndromes in which stem cell hypoproliferation is involved are treatable with stem cell stimulating amounts of INPROL.

Antibodies, monoclonal or polyclonal, are developed by standard techniques to the INPROL peptides or polypeptides. These antibodies or INPROL peptides or polypeptides are labeled with detectable labels of which many types are known in the art. The labeled INPROL or anti-INPROL antibodies are then employed as stem cell markers to identify and isolate stem cells by administering them to a patient directly for diagnostic purposes. Alternatively, these labeled peptides, polypeptides or antibodies are employed ex vivo to identify stem cells in a hematopoietic cell preparation to enable their removal prior to purging neoplastic cells in the marrow. In a similar manner, such labeled peptides, polypeptides or antibodies are employed to isolate and identify epithelial or other stem cells. In addition, such antibodies, labeled or unlabeled, are used therapeutically through neutralization of INPROL activity or diagnostically through detection of circulating INPROL levels.

INPROL can be cloned from human gene or cDNA libraries for expression of recombinant human INPROL using standard techniques. For example, using sequence information obtained from the purified protein, oligonucleotide probes are constructed which can be labeled, e.g., with 32-phosphorus, and used to screen an appropriate cDNA library (e.g., from bone marrow). Alternatively, an expression library from an appropriate source (e.g., bone marrow) is screened for cDNA's coding for INPROL using antibody or using an appropriate functional assay (e.g., that described in Example 2). Hemoglobin itself, as well as the individual alpha and beta chains, have been cloned and expressed using methods known in the state of the art (see Pagnier et al., Rev. Fr. Transfus. Hemobiol. 35:407–15, 1992; Looker et al., Nature 356:258–60, 1992; Methods in Enzymology vol. 231, 1994).

The present invention includes DNA sequences which include: the incorporation of codons "preferred" for expression by selected nonmammalian hosts: the provision of sites for cleavage by restriction endonuclease enzymes; and the provision of additional initial, terminal or intermediate DNA sequences which facilitate construction of readily-expressed vectors or production or purification of the alpha, beta, gamma, delta, epsilon and/or zeta chain of hemoglobin.

The present invention also provides DNA sequences coding for polypeptide analogs or derivatives of hemoglobin alpha, beta, gamma, delta, epsilon and/or zeta chains which differ from naturally-occurring forms in terms of the identity or location of one or more amino acid residues (i.e., deletion analogs containing less than all of the residues specified; substitution analogs, wherein one or more residues specified are replaced by other residues; and addition analogs wherein one or more amino acid residues is added to a terminal or medial portion of the polypeptide) and which share some or all of the properties of naturally-occurring forms.

In an advantageous embodiment, INPROL is the product of prokaryotic or eukaryotic host expression (e.g., by bacterial, yeast, higher plant, insect and mammalian cells in culture) of exogenous DNA sequences obtained by genomic or cDNA cloning or by gene synthesis. That is, in an advantageous embodiment, INPROL is "recombinant INPROL". The product of expression in typical yeast (e.g., *Saccharomyces cerevisiae*) or prokaryote (e.g., *E. coli*) host cells are free of association with any mammalian proteins. The products of expression in vertebrate (e.g., non-human mammalian (e.g., COS or CHO) and avian) cells are free of association with any human proteins. Depending upon the host employed, polypeptides of the invention can be glycosylated or can be non-glycosylated. Polypeptides of the invention optionally also include an initial methionine amino acid residue (at position−1).

The present invention also embraces other products such as polypeptide analogs of the alpha, beta, gamma, delta, epsilon and/or zeta chain of hemoglobin. Such analogs include fragments of the alpha, beta, gamma, delta, epsilon and/or zeta chain of hemoglobin. Following well known procedures, one can readily design and manufacture genes coding for microbial expression of polypeptides having primary sequences which differ from that herein specified for in terms of the identity or location of one or more residues (e.g., substitutions, terminal and intermediate additions and deletions). Alternatively, modifications of cDNA and genomic genes can be readily accomplished by well-known site-directed mutagenesis techniques and employed to generate analogs and derivatives of the alpha, beta, gamma, delta, epsilon or zeta chains of hemoglobin. Such products share at least one of the biological properties of INPROL but can differ in others. As examples, products of the invention include the alpha, beta, gamma, delta, epsilon or zeta chains which is foreshortened by e.g., deletions; or those which are more stable to hydrolysis (and, therefore, can have more pronounced or longer-lasting effects than naturally-occurring); or which have been altered to delete or to add one or more potential sites for O-glycosylation and/or N-glycosylation or which have one or more cysteine residues deleted or replaced by, e.g., alanine or serine residues and are more easily isolated in active form from microbial systems; or which have one or more tyrosine residues replaced by phenylalanine and bind more or less readily to target proteins or to receptors on target cells. Also comprehended are peptide or polypeptide fragments duplicating only a part of the continuous amino acid sequence or secondary conformations within the alpha, beta, gamma, delta, epsilon or zeta chains which fragments can possess one property of INPROL (e.g., receptor binding) and not others (e.g., stem cell inhibitory activity). It is noteworthy that activity is not necessary for any one or more of the products of the invention to have therapeutic utility (see, Weiland et al., Blut 44:173–5, 1982) or utility in other contexts, such as in assays of inhibitory factor antagonism. Competitive antagonists are useful in cases of overproduction of stem cell inhibitors or its receptor.

In addition, peptides derived from the protein sequence which retain biological activity can be chemically synthesized using standard methods. The present invention also provides for sequences coding for peptide analogs or derivatives of hemoglobin alpha, beta, gamma, delta, epsilon and/or zeta chain which differ from naturally-occurring forms in terms of the identity or location of one or more amino acid residues (e.g., deletion analogs containing less than all of the residues specified; substitution analogs, wherein one or more residues specified are replaced by other residues, either naturally occuring or other analogs known in the state of the art such as D-amino acids; and addition analogs wherein one or more amino acid residues is chemically modified to increase stability, solubility and/or resistance to proteolysis) and which share some or all of the properties of naturally-occurring forms.

Peptide sequences such as described above can be identified by a variety of means. Comparison of the three dimensional structures of native hemoglobin chains active in the assay (e.g., alpha chain) with structurally related proteins which are inactive (e.g., myoglobin) can identify regions which have different conformations in three-dimensional space and which are therefore candidate regions for active peptides. Another approach uses selective proteolysis, in which proteolytic enzymes are used in limited digests of hemoglobin chains resulting in peptides which can separated, for example, by reverse phase HPLC and then assayed for stem cell inhibition. Peptides can also be generated by chemical synthesis (e.g., solid phase synthesis); a series of overlapping peptides (e.g., 15-mers) which encompass the sequence of the hemoglobin chain of interest (e.g., alpha chain) can easily be generated and tested in stem cell assays. Combinatorial libraries can be generated in which multiple chemical syntheses are conducted and where selected amino acid positions are made variable resulting in large numbers of peptide analogs for screening (e.g., Dooley et al., Peptide Research 8:124–137, 1995). Alternatively, recombinant methods can be employed. Site directed mutagenesis can be used to identify critical residues necessary for activity of a particular hemoglobin chain. Regions of a chain which is known to be active as a stem cell inhibitor (e.g., alpha chain) can be substituted with regions from a related but inactive protein (e.g. myoglobin) and tested in stem cell assays, allowing for identification of regions necessary for activity. Such identified regions can be expressed as peptides and tested for activity in stem cell cycling assays.

Homologous or analogous versions of INPROL from other species are employed in various veterinary uses, similar to the therapeutic embodiments of the invention described above.

INPROL at stem cell inhibitory amounts act on cycling stem cells by reversibly placing them in an undividing or slowly dividing "resting" state. When it is desirable to stimulate the quiescent stem cells into division, e.g., after treatment of a patient with cancer chemotherapy agents or radiation, INPROL at stem cell stimulatory amounts can be used. Alternatively, or in addition, colony-stimulating factors and other hematopoietic stimulants are administered to the subject. Examples of such factors include but are not limited to: M-CSF (CSF-1), GM-CSF, G-CSF, Megakaryocyte-CSF, thrombopoieitin, stem cell factor or other cytokines, such as IL-1, IL-2, IL-3, IL-4, IL-5, IL-6, IL-7, IL9, IL-11, IL-12, IL-13, IL-14, or erythropoietin.

INPROL polypeptides or active fragments having stem cell inhibitory activity are purified or synthesized by conventional chemical processes combined with appropriate bioassays for stem cell inhibitory activity, as exemplified in the protocols described below.

In one embodiment of the invention, a therapeutically effective amount of the INPROL protein or a therapeutically effective fragment thereof is employed in admixture with a pharmaceutically acceptable carrier. This INPROL composition is generally administered by parenteral injection or infusion. Subcutaneous, intravenous, or intramuscular injection routes are selected according to therapeutic effect achieved.

When systemically administered, the therapeutic composition for use in this invention is in the form of a pyrogen-free, parenterally acceptable aqueous solution. Pharmaceutically acceptable sterile protein solution, having due regard to pH, isotonicity, stability, carrier proteins and the like, is within the skill of the art.

Also comprehended by the invention are pharmaceutical compositions comprising therapeutically effective amounts of peptide or polypeptide products of the invention together with suitable diluents, preservatives, solubilizers, emulsifiers, adjuvants and/or carriers useful in INPROL therapy. A "therapeutically effective amount" as used herein refers to that amount which provides a therapeutic effect for a given condition and administration regimen. Such compositions are liquids, gels, ointments, or lyophilized or otherwise dried formulations and include diluents of various buffer content (e.g., Tris-HCl, acetate, phosphate), pH and ionic strength, additives such as albumin or gelatin to prevent adsorption to surfaces, detergents (e.g., Tween 20, Tween 80, Pluronic F68, bile acid salts), solubilizing agents (e.g., glycerol, polyethylene glycol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc. or into liposomes, niosomes, microemulsions, micelles, unilamellar or multilamellar vesicles, biodegradable injectable microcapsules or microspheres, or protein matrices, erythrocyte ghosts, spheroplasts, skin patches, or other known methods of releasing or packaging pharmaceuticals. Such compositions will influence the physical state, solubility, stability, rate of in vivo release, and rate of in vivo clearance of INPROL. Controlled or sustained release compositions include formulation in lipophilic depots (e.g., fatty acids, waxes, oils). Also comprehended by the invention are particulate compositions coated with polymers (e.g., poloxamers or poloxamines) and INPROL coupled to antibodies directed against tissue-specific receptors, ligands or antigens or coupled to ligands of tissue-specific receptors. Other embodiments of the compositions of the invention incorporate particulate forms of protective coatings, protease inhibitory factors or permeation enhancers for various routes of administration, including parenteral, pulmonary, nasal, topical (skin or mucosal) and oral. In another embodiment, the composition containing INPROL is administered topically or through a transdermal patch.

In one embodiment, the compositions of the subject invention are packaged in sterile vials or ampoules in dosage unit form.

The invention also comprises compositions including one or more additional factors such as chemotherapeutic agents (e.g., 5-fluorouracil (5FU), cytosine arabinoside, cyclophosphamide, cisplatin, carboplatin, doxyrubicin, etoposide, taxol, alkylating agents), antiviral agents (e.g., AZT, acyclovir), TNF, cytokines (e.g., interleukins), antiproliferative drugs, antimetabolites, and drugs which interfere with DNA metabolism.

The dosage regimen involved in a method for treating the subject anticipating exposure to such cytotoxic agents or for treatment of hyperproliferating stem cells is determined by the attending physician considering various factors which modify the action of drugs; e.g., the condition, body weight, sex, and diet of the patient, the severity of any infection, time of administration and other clinical factors.

Following the subject's exposure to the cytotoxic agent or radiation, the therapeutic method of the present invention optionally employs administering to the subject INPROL at stem cell stimulatory amounts optionally including one or more lymphokines, colony stimulating factors or other cytokines, hematopoietins, interleukins, or growth factors to generally stimulate the growth and division of the stem cells (and their descendants) inhibited by the prior treatment with INPROL. Such therapeutic agents which encourage hematopoiesis include IL-1, IL-2, IL-3, IL-4, IL-5, IL-6, IL-7, Meg-CSF, M-CSF (CSF-1), GM-CSF, G-CSF or erythropoietin. The dosages of these agents are selected according to knowledge obtained in their use in clinical trials for efficacy in promoting hematopoietic reconstitution after chemotherapy or hematopoietic stem cell transplant. These dosages would be adjusted to compensate for variations in the physical condition of the patient, and the amount and type of chemotherapeutic agent or radiation to which the subject was exposed. Progress of the reversal of the inhibition of the stem cells caused by administration of INPROL in the treated patient is monitored by conventional methods.

In the treatment of leukemia, it is beneficial to administer both INPROL to inhibit normal stem cell cycling and a stimulator of leukemic cell growth, such as IL-3 or GM-CSF, simultaneously with the cytotoxic drug treatment or during irradiation. By this protocol, it is possible to achieve the greatest differences between the cycling statuses and drug sensitivities of normal and leukemic cells.

EXAMPLE 1

In Vivo Stem Cell Proliferation Inhibition Assay

For the detection of stem cells proliferation the number of CFU-S in S-phase of the cell cycle was measured by the $^3$H-Thymidine "suicide" method (Becker et al., Blood 26:296–308, 1965).

Immature hematopoietic progenitors—Colony Forming Units in spleen (CFU-S)—can be detected in vivo by forming macroscopic colonies in the spleens of lethally irradiated mice, 8–12 days after the intravenous injection of hematopoietic cells (Till & McCulloch, 1961).

For the standard CFU-S proliferation assay the method of $^3$H-Thymidine "suicide" is usually applied (Becker et al., 1965). The method is based on incorporation of radiolabelled Thymidine, ($^3$H-Thymidine) a precursor of DNA into cells during DNA synthesis. The CFU-S which are in S-phase of the cycle at the time of testing, are killed by the high radioactivity and therefore not able to form colonies in spleen. Thus, the difference between the number of CFU-S formed by the injection of the cell sample incubated without $^3$H-Thymidine and the same cells incubated with $^3$H-Thymidine shows the percentage of the proliferating CFU-S in the original sample.

The inhibitor testing can not be done with the bone marrow stem cell population from unstimulated animals, as far as the inhibitor only effects cycling CFU-S, which are as low as 7–10% of the total CFU-S population in the bone marrow of normal mice.

To stimulate CFU-S proliferation, phenylhydrazine (PHZ), or sublethal irradiation were used (Lord, 1976).

We have developed the method of using testosterone-propionate (TSP) based on its stimulatory effect on CFU-S cycling (Byron et al., Nature 228:1204, 1970) which simplified the testing and did not cause any side effects. The TSP induced stimulation of CFU-S proliferation within 20–24 hours after injection and the effect could be seen for at least 7 days.

The procedure used for the screening of the fractions during purification of the Inhibitor was as follows:

Mice: BDF$_1$ or CBF$_1$ Mice Strains Were Used Throughout all Testing.

Donor mice were treated with a 10 mg/100 g dose of TSP by intraperitoneal injection of 0.2 ml/mouse in order to induce 30–35% of the CFU-S into S-phase.

Twenty-four hours later the bone marrow is taken from the femurs for the cell suspension preparation. Five to ten million cells per ml are then incubated with different control and test fractions for 3.5 hours at 37° C. in water bath, with two tubes for each group (one for hot (radioactive) and one for cold (non-radioactive)).

After 3.5 hours, $^3$H-Thymidine (1 mCi/ml, specific activity 18–25 Ci/mmole) is added to each hot tube in a volume of 200 µl per 1 ml of cell suspension; nothing is added to the cold tubes. Incubation is continued for 30 more minutes at 37° C.

After the 30 minute incubation the kill reaction is terminated by adding 10 ml of cold (4° C.) medium containing 400 µg/ml nonradioactive Thymidine. Cells are washed extensively (3 times).

Cells are resuspended and diluted to a desirable concentration for the injections, usually 2–4×10$^4$ cells per mouse in 0.3–0.5 ml.

Recipient mice, 8–10 per group, are irradiated not later than 6 hours before the injections.

Recipient spleens are harvested on day 9–12 and fixed in Tellesnitsky's solution; the colonies are scored by eye score. The percentage of cells in S-phase are calculated using the formula.

$$\% S = \frac{a-b}{a} \times (100\%)$$

where a—CFU-S number without $^3$H-Thymidine where b—CFU-S number with $^3$H-Thymidine The test data of INPROL presented in Table 1 demonstrate that cycling stem cells after treatment with INPROL become resistant to the action of $^3$H-Thymidine. For this and all of the following examples, the term "pINPROL" refers to the purified protein from porcine bone marrow. The same protection is seen for the S-phase specific cytotoxic drugs cytosine arabinoside and hydroxyurea (data not shown). If the treated stem cells are then washed with the cold media containing non-radioactive Thymidine, the surviving stem cells proliferate in mouse spleens to form colonies normally.

TABLE 1

Inhibitory Activity Of pINPROL On CFU-S Proliferation During Four Hour Incubation With Bone Marrow Cells

| Group | −$^3$H-TdR | +$^3$H-TdR | Percent CFU-S Killed by $^3$H-TdR |
|---|---|---|---|
| No incubation | 22.2 ± 2.0* | 13.7 ± 2.4* | 38.3 ± 1.7 |
| 4 Hour with Media | 18.7 ± 3.0* | 11.4 ± 1.3* | 43.1 ± 1.4 |
| 4 Hour with pINPROL | 21.2 ± 2.3* | 20.7 ± 2.6* | 2.1 ± 0.08 |

*CFU-S per 2 × 10$^4$ cells

EXAMPLE 2

In Vitro Stem Cell Proliferation Inhibition Assay

Using the following test system (Lord et al., in *The Inhibitors of Hematopoiesis* pp. 227–239, 1987) the direct effect of INPROL was shown. The multilineage factor (IL-3) dependent stem cell line, FDCP mix A4 (A4), was maintained in IMDM medium supplemented with 20% horse serum and 10% WEHI-3-conditioned medium as a source of colony-stimulating IL-3.

A tritiated Thymidine incorporation assay was used to measure proliferation: A4 cells ($5 \times 10^4$ in 100 µl medium with 20% horse serum and 50% of WEHI-3 CM) were incubated at 37° C. in 5% $CO_2$ for 16 hours.

pINPROL or the crude BNE (fraction IV) were added at the start. Tritiated thymidine (($^3$H-Tdr) 3.7 KBq in 50 µl at 740 GBq/mmole) was then added to each group for a further 3 hours of incubation. The level of proliferation was measured by harvesting cells and the % inhibiton calculated using the formula $$\% \text{ Inhibition} = \frac{\text{cpm without INPROL} - \text{cpm with INPROL}}{\text{cpm without INPROL}} \times (100\%)$$

Figure 6:
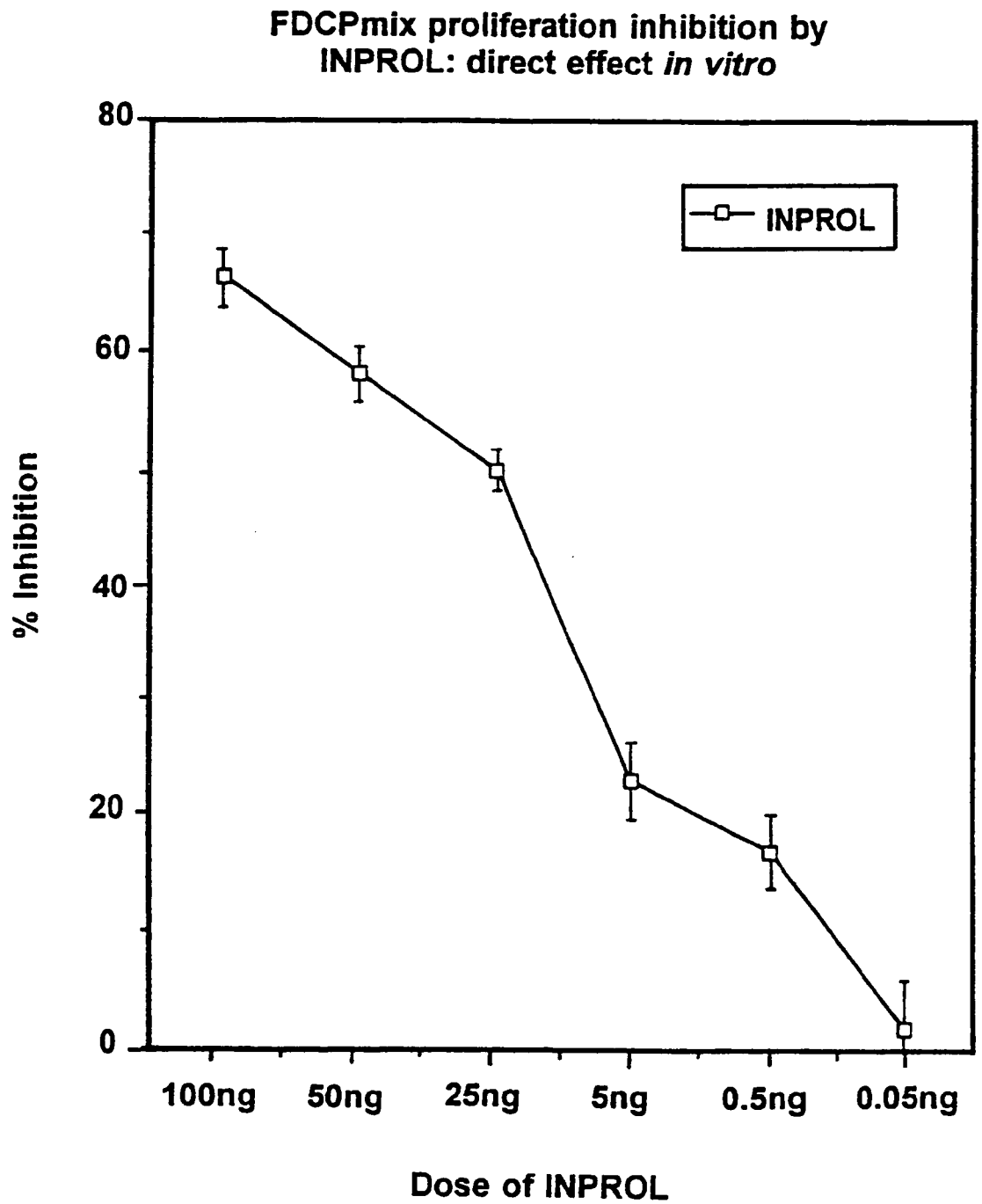
FIG. 6 shows tritiated thymidine incorporation (cpm) into cells of the FDCP-mix line without (Control=0% Inhibition) and with various amounts of INPROL purified from porcine bone marrow (pINPROL). Data are normalized against the control value.

Incorporation of tritiated thymidine ($^3$H-Tdr) by FDCP-mix-A4 cells grown in the presence of graded doses of normal bone marrow extract or pINPROL is depicted on FIG. 6. It can be seen that purified composition of pINPROL is at least 1,000 times more active than the starting material. Time of exposure (16 hours) is an important factor for effective inhibition and shows the evidence of the direct effect of pINPROL on stem cells of the A4 cell line.

EXAMPLE 3

Inhibition of CFU-S Proliferation by INPROL Injected in vivo Doses and the Duration of the Effect The studies of the effect of INPROL injected in vivo revealed that INPROL can effectively block the recruitment of CFU-S into cycle, thus protecting those cells from the cytotoxic effect of further treatment, showing its potential for clinical use.

The experimental protocol had two goals: to check the effect of INPROL on CFU-S when injected in vivo and to define the effective duration of INPROL activity in relation to cycling stem cells.

To stimulate CFU-S proliferation, the injection of testosterone-propionate was used based on the effect mentioned above in Example 1.

Mice BDF1 were injected with TSP (10 mg/100 g) on Day 0; 24 hours later mice of each experimental group (4 mice per group) received a single pINPROL injection at doses of 0 µg, 5 µg, 10 µg, and 15 µg/mouse i.p.

Twenty-four hours after pINPROL injection, mice were sacrificed and the percent of cycling CFU-S was measured by the assay described in Example 1. TSP injection induced about 50% CFU-S into cycling in comparison with 7% in untreated mice pINPROL in doses as low as 2 µg/mouse was able to inhibit TSP induced proliferation down to the normal level.

Figure 7:
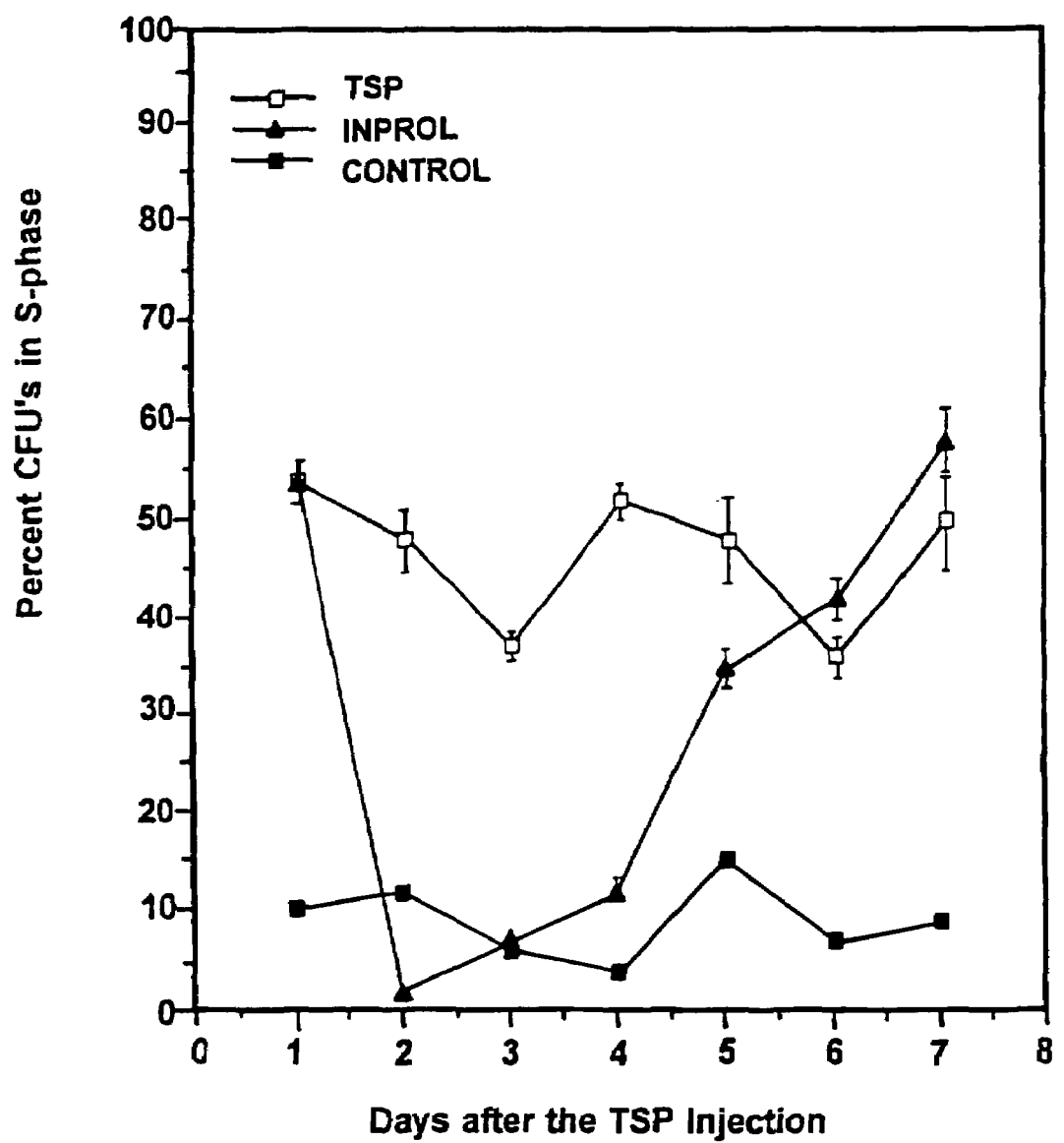
FIG. 7 shows the percent of cells in the S phase of the cell cycle after treatment of mice with testosterone propionate (TSP), TSP plus pINPROL, or vehicle (Control). Each group contained 25 animals (3–4 per time point).

For the duration of the effect evaluation, one group of mice (21 mice per group) was injected with TSP only and another group was injected both with TSP and pINPROL (24 hours after TSP). The CFU-S cycling was measured every 24 hours during a week by taking 3 donors from each group and measuring CFU-S cycle status in their bone marrow by method described (see Example 1). Data presented in FIG. 7 show that while the duration of the effect of TSP is at least 7 days, a single injection of INPROL can place CFU-S into quiescence and keep them out of cycle for no more than 48–72 hours. Since the majority of chemotherapeutic agents used for cancer and leukemia chemotherapy have a relatively short in vivo half-life, usually less than 24 hours the INPROL effect according to the data obtained is maintained for longer than the effective time during which the chemotherapeutic agents like cytosine arabinoside or hydroxyurea are active in vivo. More importantly, for chemotherapeutic and radiation treatments having longer intervals (more than 24 hours and less than 96 hours) between the first (non-damaging for the stem cells) and the second (damaging to the CFU-S) treatments, a single injection of INPROL during the intervals between the two applications of chemotherapeutic agent or radiation should be sufficient. For several repeatable cycles of cytotoxic therapy or radiation the same strategy could be applied based on the duration of the INPROL effect.

EXAMPLE 4

Most Primitive Hematopoietic Stem Cells Stimulated to Cycle Rapidly After Treatment with 5-FU are Protected by INPROL from the Second 5-FU Exposure The drug 5-fluorouracil (5-FU) drastically reduces the number of cells in the myeloid and lymphoid compartments. It is usually thought of as being cell-cycle specific, targeting rapidly proliferating cells, because incorporation of the nucleotide analogue into DNA during S-phase of the cell cycle or before results in cell death. The long-term survival and immunohematopoietic reconstitution of the bone marrow of mice is not affected by a single dose of 5-FU; however, it was demonstrated (Harrison et al. Blood 78:1237–1240, 1991) that pluripotent hematopoietic stem cells (PHSC) become vulnerable to a second dose of 5-FU for a brief period about 3–5 days after the initial dose. It can be explained that PHSC normally cycle too slowly for a single dose of 5-FU to be effective and are stimulated into rapid cycling by stimuli resulting from the initial 5-FU treatment. We have proposed that PHSC can be returned to a slow cycle status by INPROL and thus protected from the second 5-FU treatment.

Figure 8:
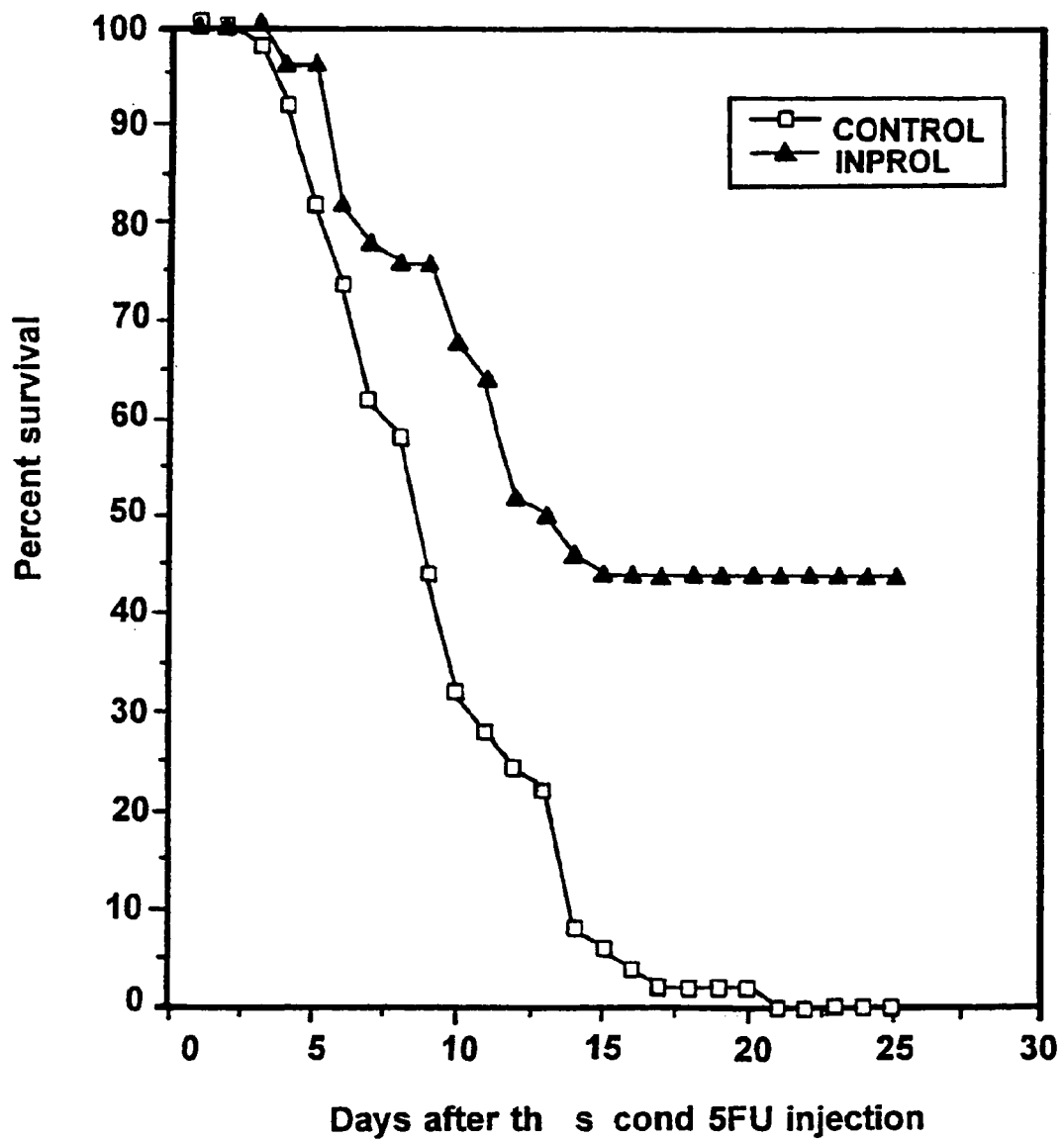
FIG. 8 shows survival of mice treated with two doses of 5-FU, with or without pINPROL treatment. Each group contained 30 animals.

The mice used in these experiments were BDF1 male mice. A stock solution of 5-FU (Sigma) was prepared in physiologic saline at a concentration of 10 µg/ml. Each treated mouse received 2 mg of 5-FU per 10 g body weight via a tail vein at Day 0 of the experiment; 24 hours later mice were injected with pINPROL (10 µg/100 g of body weight) intraperitoneally and on Day 3 were injected with the second dose of 5-FU. The survival study was conducted by monitoring the death of mice in experimental (treatment with pINPROL) and control groups of 30 mice each. The survival curves are shown in FIG. 8.

EXAMPLE 5

Effects of Pre-Incubation with INPROL vs. MIP-1α in Bone Marrow Cells

The purpose of this experiment was to compare the inhibitory effects of pre-incubation with pINPROL and MIP-1α on mouse bone marrow cells in vitro.

The following procedure was used:

in vivo: BDF1 mice, 6–15 weeks of age, are injected with 200 mg/kg 5FU i.p. 48 hours before harvesting marrow from the femurs.

in vitro: A single cell pooled suspension is counted and $5 \times 10^6$ cells are incubated in a total of 2 mls with or without pINPROL or MIP-1α, with 5% horse serum, IMDM media with added L-glutamine, at 37° C. and 5% $CO_2$ for 4 hours. The cells are then washed twice and recounted. They are plated in methylcellulose in the following final conditions:

0.8% methylcellulose

25% horse serum 20 ng/ml recombinant murine IL3

L-glutamine added $5 \times 10^5$ cells per ml

IMDM media

Plates were incubated for 11 days at 37° C. and 5% $CO_2$ in 100% humidity. Colonies more than 50 cells were counted.

TABLE 2

| Groups | Colony Number | Percent of Control |
|---|---|---|
| Control | 31.0 | 100% |
| pINPROL | 21.25 | 68.5% |
| MIP-1α | 35.25 | 114% |

EXAMPLE 6

INPROL Inhibits HPP-CFC Proliferation

An in vitro assay for assessing murine reconstituting stem cells and early precursors is the high proliferative potential colony (HPP-PFC) assay; other related assays, e.g., CFU-A, CFU-GM, CFU-E, and CFU-GEMM, detect progressively restricted progenitor populations (M. Moore, Blood 177: 2122–2128, 1991). This example shows that pretreatment of cells with pINPROL inhibits their proliferation, whereas MIP-1α fails to do so under these experimental conditions.

BDF1 mice were treated with 5-fluorouracil (200 mg/kg i.p.) before their bone marrow was assayed for HPP-CFC numbers. Cells were washed by centrifugation and incubated at densities of $10^6$ to $5 \times 10^6$/ml in medium with either no added agent (Controls), pINPROL (25 ng/ml) or MIP-1α (200 ng/ml) for 4 hours. After incubation, cells were washed and plated in agar (0.3%) with 30% FCS and combined conditioned medium from 5637 and WEHI-3B cell lines (7.5% of each conditioned medium, as recommended by Sharp et al., 1991). Plating concentration was $5 \times 10^4$ cells/ml in 60 mm dishes. Colonies were scored on day 14 and the results are indicated below.

TABLE 3

| Group | HPP-CFU | % of Control |
|---|---|---|
| Control | 15.5 ± 1.2 | 100% |
| pINPROL | 8.3 ± 0.7 | 53.5% |
| MIP-1α | 15.8 ± 0.9 | 101% |

According to these results, MIP-1α did not inhibit proliferation of the most immature precursors when present only during the pre-incubation period. pINPROL did effectively inhibit proliferation under these conditions, indicating fundamental differences between pINPROL and MIP-1α in terms of biological activity.

EXAMPLE 7

INPROL Therapy Effect on the Recovery from Radiation-induced Bone Marrow Aplasia Bone marrow aplasia is the primary limiting toxicity of radiation cancer therapy. It has been demonstrated that some growth factors (e.g., G-CSF, GM-CSF, erythropoietin) can accelerate recovery from radiation-induced bone marrow aplasia. The concept of protection by using an inhibitor of stem cell proliferation is a different and complementary approach in coping with hematological damage. To follow the treatment procedure developed earlier (Examples 3, 4) a model of lethal irradiation of mice was established. It is known in the art that mice receiving 9Gy of cobalt 60 start dying after 10–14 days; by Day 30, mortality approximates 50%. This lethal dose was used in our model by splitting it into two subsequent applications of 4.5Gy each with an interval 3 days between doses. Preliminary data showed that the survival curve in that model was very close to that known for a single irradiation with 9Gy; moreover the test for the CFU-S proliferation showed that 24 hours after the first irradiation, 35–50% of CFU-S are induced to proliferate. Such cells can be protected by a stem cell inhibitor delivered prior to the second dose.

To examine this possibility, mice (50 mice/group) received 4.5Gy on Day 0. Twenty four hours later, one group received pINPROL (2 μg/mouse i.p.) and another, control group was injected with saline. The second dose of radiation (4.5 Gy) was given on Day 3.

Figure 9:
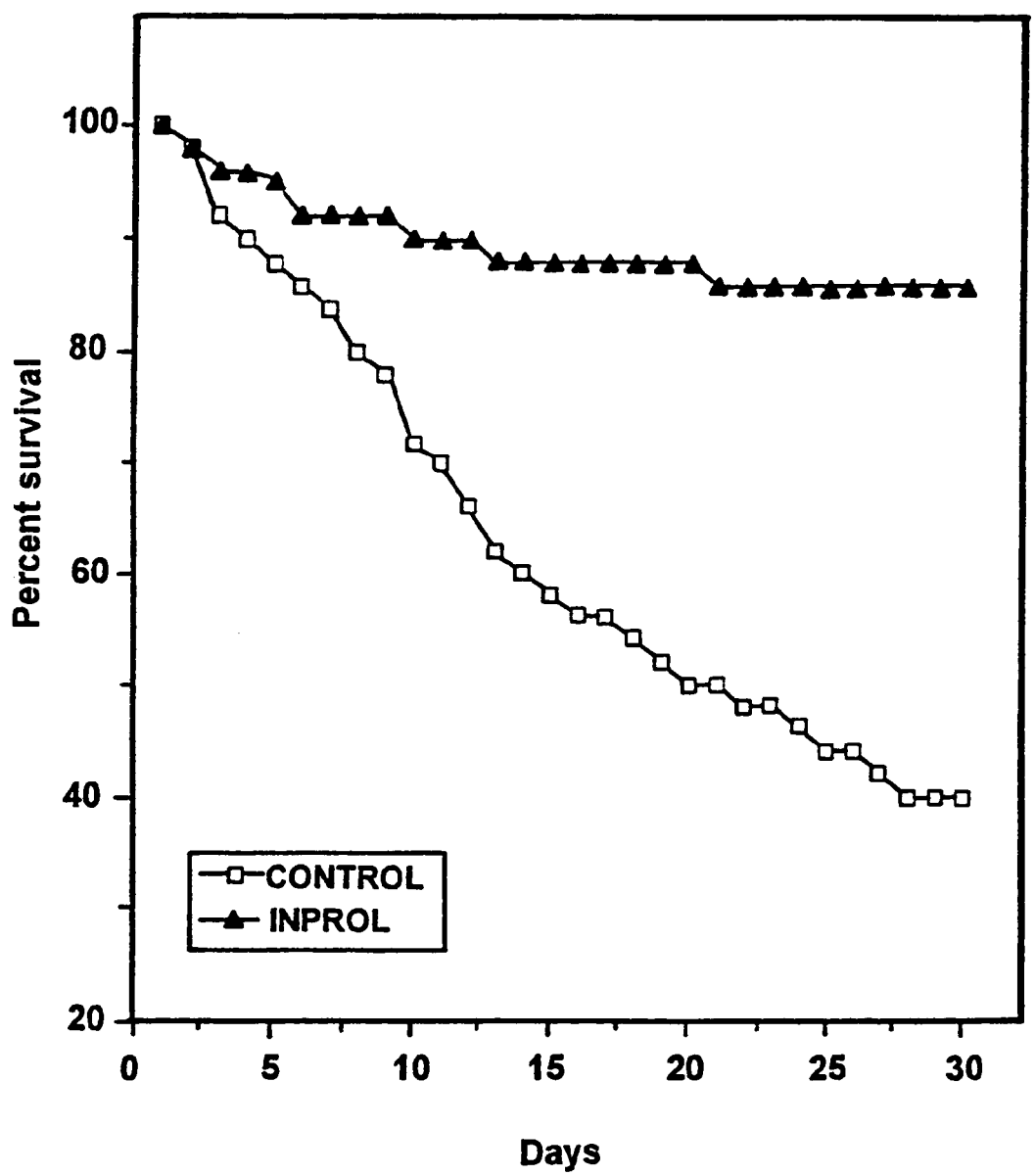
FIG. 9 shows survival of irradiated mice, with and without pINPROL treatment. Each group contained 50 animals.

FIG. 9 shows the increased survival after a single dose of pINPROL. The conditions of the model are clinically relevant for treating any cancer, including those characterized by solid tumors; such treatment would be administered to a patient having cancer by delivering an effective dose of INPROL between two consecutive dosages of radiation, thereby allowing greater dosages of radiation to be employed for treatment of the cancer. It should also be possible to extend this modality to chemotherapeutic agents.

EXAMPLE 8

INPROL Use for the Autologous Bone Marrow Transplantation

Bone marrow transplantation is the only known curative therapy for several leukemias (CML, AML, and others). Ex vivo conditioning of autologous BMT for infusion should provide potential autologous sources of normal stem cells free of leukemic contamination and able to repopulate the recipient's hematopoietic system to allow aggressive and effective therapy.

1. Long-term Bone Marrow Culture L1210 Leukemia Model For The Study of INPROL Effect Preserving Normal Hematopoiesis During Purging with AraC.

Long-Term Bone Marrow Cultures (LTBMC) were established according to Toksoz et al. (Blood 55:931–936, 1980) and the leukemic cell line L1210 was adopted to the LTBMC by co-cultivation during 2 weeks. The simultaneous growth of normal and leukemic progenitors occurred in these combined LTBMC/L1210 cultures, similar to the situation in the bone marrow of a leukemic patient. Discrimination between normal colony forming units CFU and leukemic CFU was possible by growing them as agar colonies in the presence or absence of the conditioned medium from WEHI-3 (a murine IL-3 producing cell line). Normal cells undergo apoptosis in the absence of IL-3 whereas leukemic cells can form colonies in its absence. Suspension cells from LTBMC-L1210 composition give approximately 150 colonies in presence of IL-3 (normal hematopoietic clones) and 70 colonies when growing without IL-3 (leukemic clones) per 50,000 cells plated.

The procedure of purging was as follows: on Day 0 all suspension cells and media (10 ml/flask) were taken off the flasks with LTBMC-L1210 and replace with 2 ml of media containing 200 μg cytosine arabinoside (AraC) (Tsyrlova et al. in *Leukemia: Advances in Biology and Therapy* v. 35, 1988); after 20 hours of incubation, flasks were washed out and replaced with 2 ml of fresh media alone (control group) or media containing pINPROL at 25 ng/ml for 4 hours. After this preincubation, cells were incubated again with 100 μg/flask AraC for 3 hours at 37° C. Each group contained 4 flasks. LTBMC-L1210 cultures were washed 3 times and replaced with fresh LTBC media; they were maintained as before for the regeneration studies for 3–4 weeks.

Figure 10A:
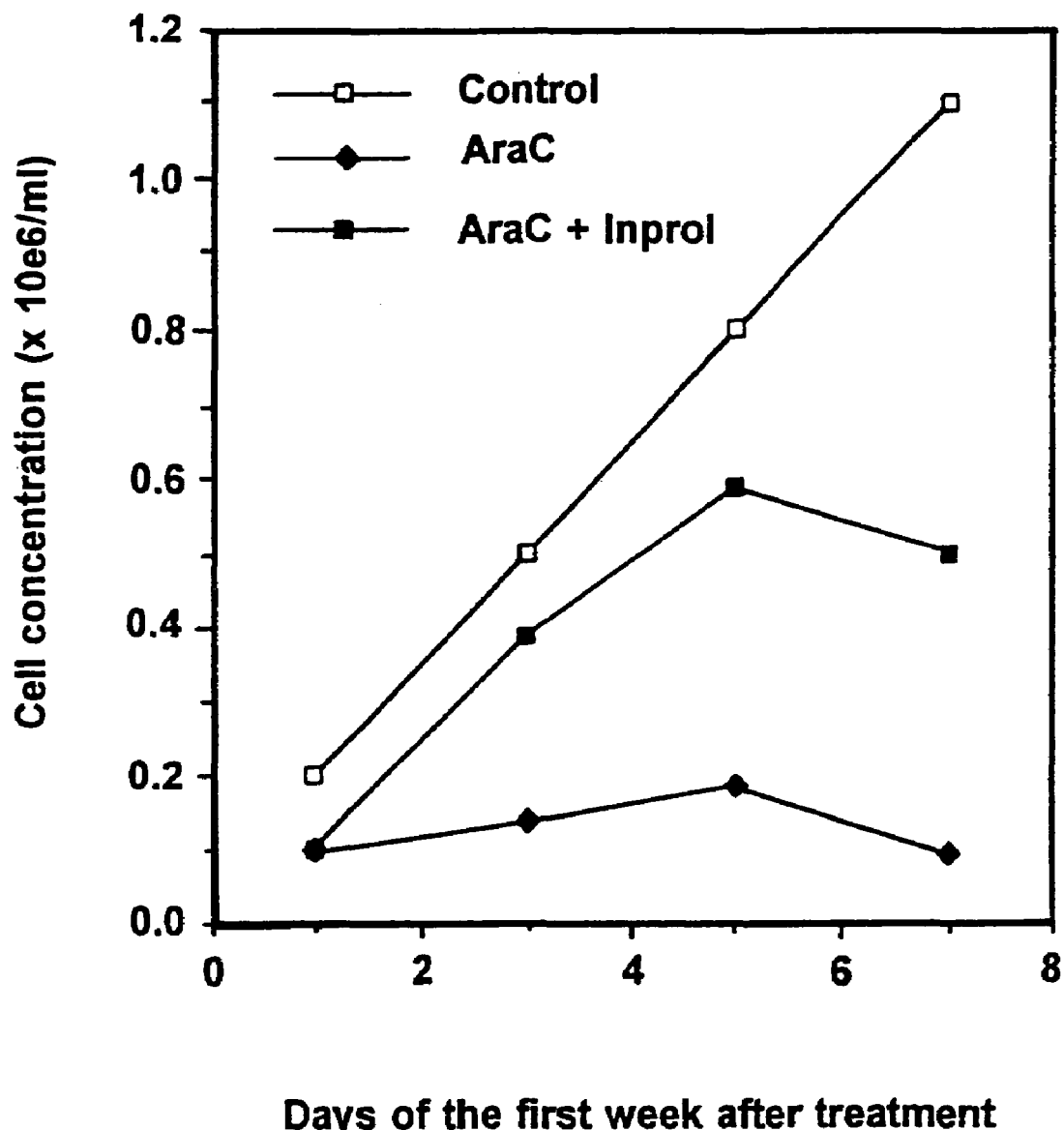
FIGS. 10A and 10B show regeneration of normal bone marrow long term culture cells 1 week (10 A) and 3 weeks (10 B) after treatment with Ara-C or Ara-C plus pINPROL.
Figure 10B:
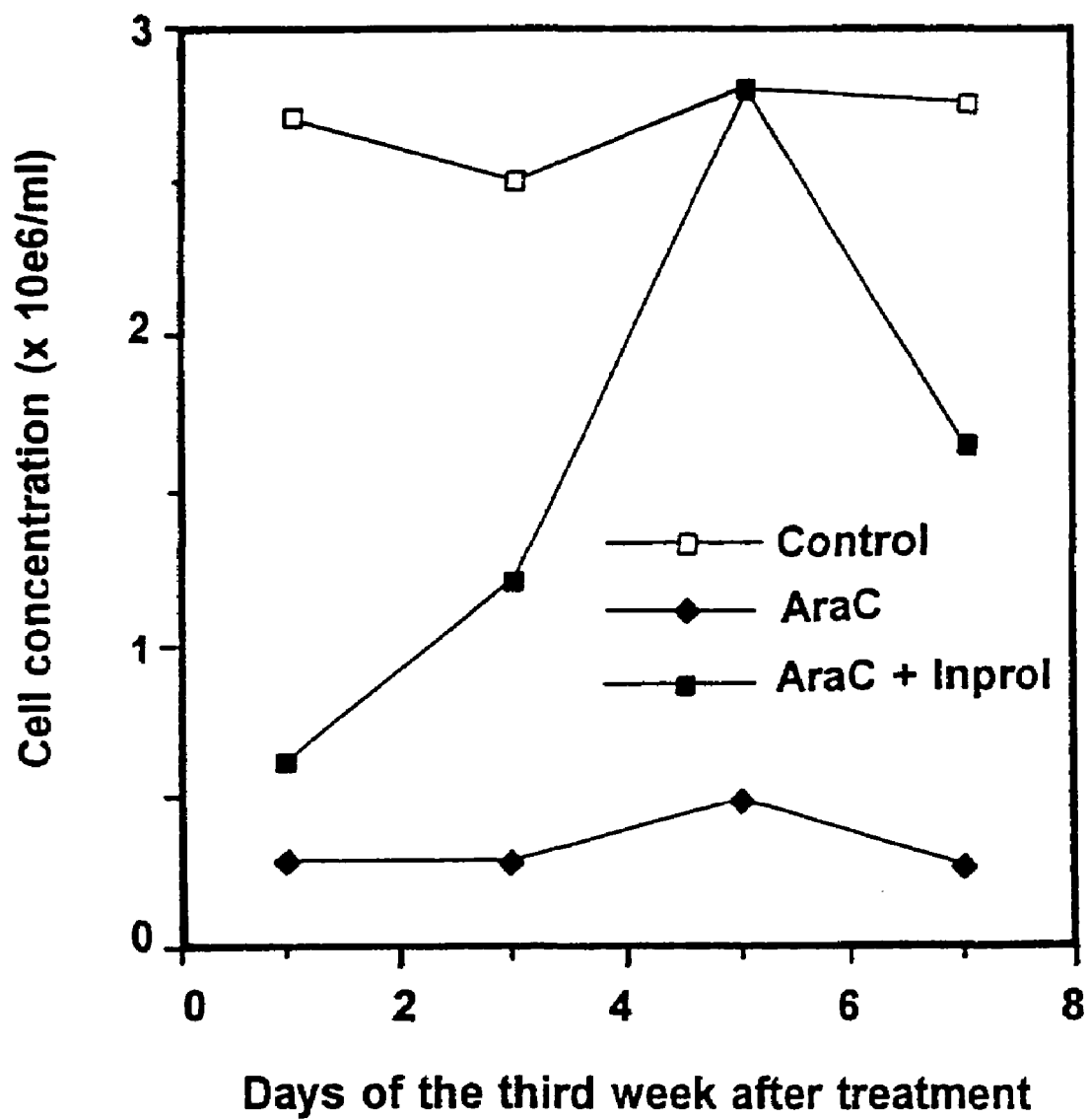

Data are presented in FIG. 10. There was no cell growth seen in control cultures treated with AraC only, while in INPROL protected flasks regeneration of hematopoiesis occurred much more rapidly due to proliferation of progenitors from the adherent layer. Moreover, the cells from the experimental group when plated in agar grew only in the presence of IL-3 giving about 100 CFU per 50,000 cells; no leukemic cell growth was observed at least during 4 weeks. Thus, marrow treated ex vivo with an effective dose of AraC in combination with INPROL can be purged of cancerous cells while the stem cells are be protected. It should be possible to extend this modality to other forms of chemotherapy or radiation treatments.

2. Marrow Repopulating Ability (MRA) and Thirty Days Radioprotection are Increased by INPROL Treatment In Vitro.

MRA, the ability of cells to repopulate the bone marrow of lethally irradiated mice, together with the ability to confer radioprotection for 30 days, is a direct in vivo measurement of the potential to rescue myelosuppressed animals (Visser et al. Blood Cells 14:369–384, 1988).

Figure 11:
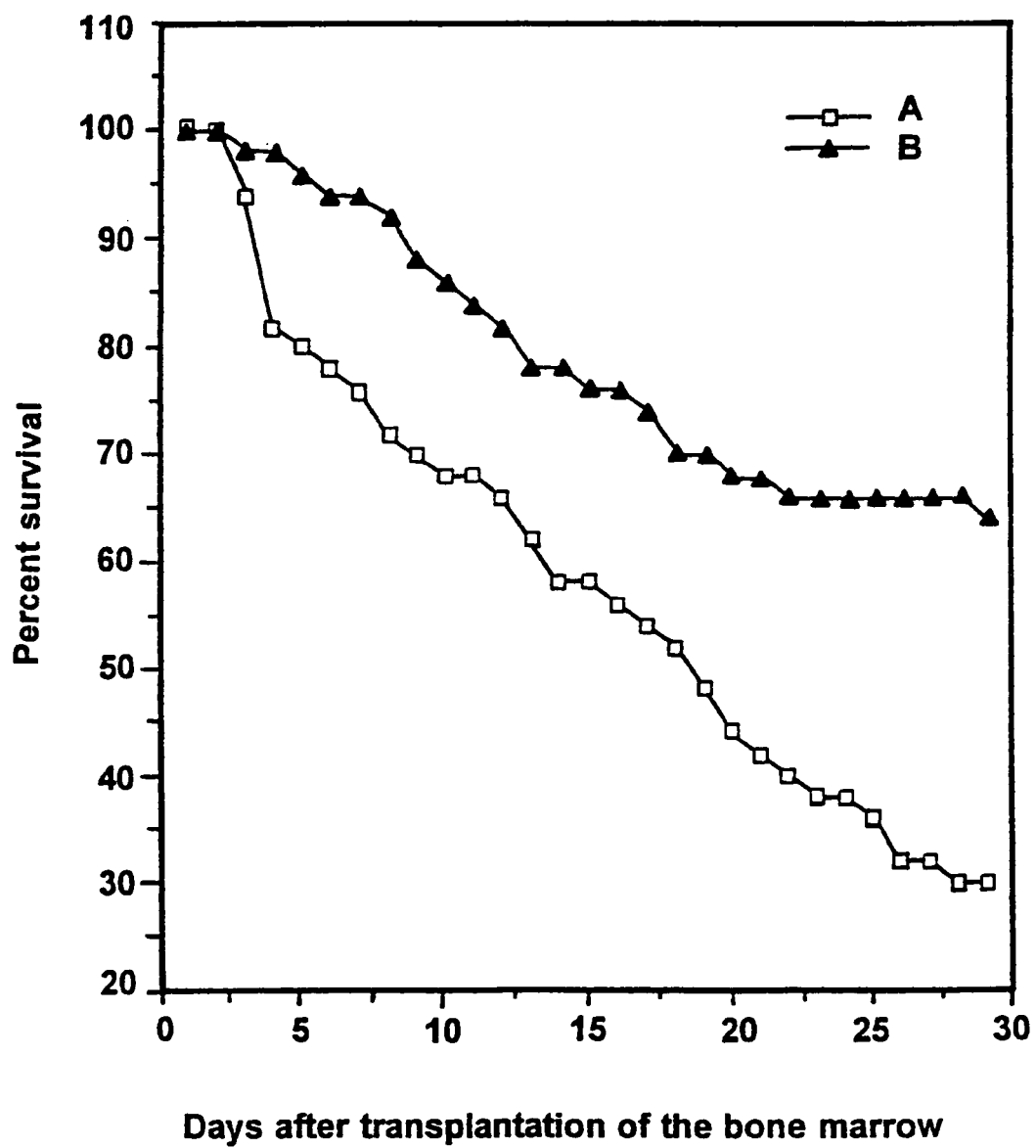
FIG. 11 shows survival of mice (75 per group) after lethal irradiation and transplantation of $3 \times 10^4$ bone marrow cells after pre-incubation with medium (Control) or pINPROL (25 ng/ml) for 4 hours. Survival was monitored for 30 days.

For radioprotection studies BDF1 mice were irradiated with 9.5Gy and restored by transplantation of bone marrow from testosterone-stimulated donors. One group of recipients was restored by bone marrow cells preincubated for 4 hours with medium (controls—group A) and another (group B) with 25 ng/ml pINPROL. Cells in both groups were washed and 30,000 cells per mouse were transplanted into irradiated animals. The survival data are shown (FIG. 11). The sum of 3 experiments is depicted, with controls normalized to 100%. pINPROL incubation increased the survival of mice from 36.5% in control group up to 61.8% by Day 30.

The increase of MRA induced by preincubation with INPROL could be one of the mechanisms in the improving of the radioprotection. To examine this hypothesis, MRA was measured according to Visser et al. (op. cit.). Briefly, the donor BDF1 mice were pretreated with testosterone, their bone marrow was preincubated with medium or pINPROL for 4 hours and injected into irradiated animals. On Day 13, the bone marrow cells from recipient femurs were plated in agar in 3 different concentration (0.01, 0.05, 0.1 equivalent of a femur) in the presence of 20% of horse serum and 10% of WEHI-CM. The number of Day 7 colonies represented the MRA as far as the colony-forming cells in the bone marrow of recipients at the time were the progenitors of the donor's immature stem cells.

Figure 12:
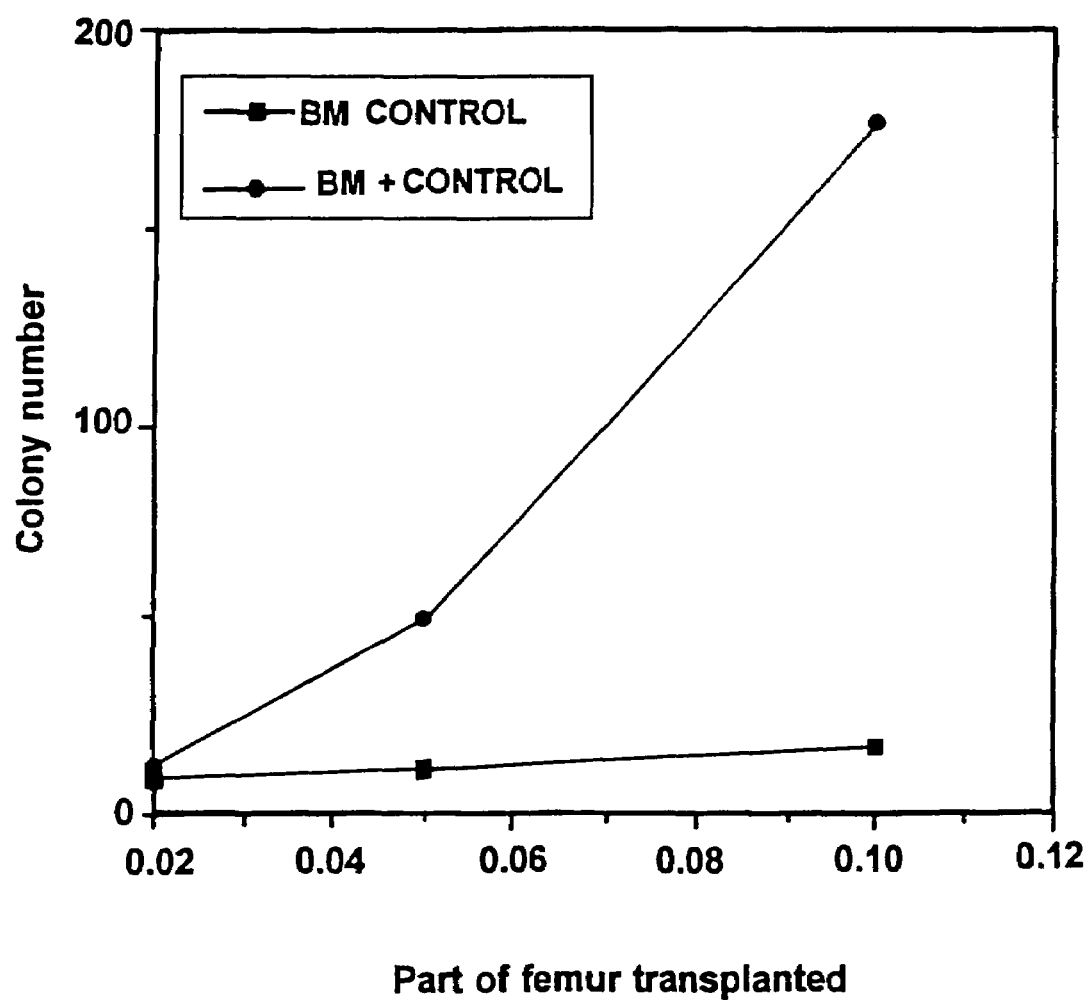
FIG. 12 shows the CFU-GM number formed after 14 days in culture by bone marrow cells from mice after lethal irradiation and restoration with donor bone marrow cells preincubated with pINPROL or medium for 4 hours.

As can be seen on FIG. 12 the MRA of the preincubated with INPROL cell population is greater than in the control group (B).

EXAMPLE 9

Antihyperproliferative Effect of INPROL on Stem Cells Can Change Their Differentiation Abnormalities Hyperproliferation of CFU-S is not only seen during restoration from cytotoxic drugs or irradiation but also as a consequence of normal aging, and is thought to be a major feature in Myelodysplastic Syndrome (MDS). It is accompanied by the differentiation disturbances such as a prevalence of the erythroid differentiation while the differentiation along the granulocytic pathway is reduced.

Bone marrow cells were incubated for 4 hours at 37° C. with 25 ng/ml of pINPROL or media (Control), washed and then plated in agar with 20% of horse serum, 2 U/ml Erythropoietin, and 10% WEHI-CM. The number of BFU-E and GM-CFU colonies were scored on Day 7. Data presented in Table 4 are summarized from 3 experiments—4 animals per point were taken for each group; 4 dishes were plated.

As is obvious from Table 4, the incubation of normal bone marrow (NBM) from intact young animals (BDF1 8–12 weeks old) with INPROL did not change the number or proportion of different types of colonies. $BDF_1$ donors pretreated with Testosterone Propionate (TSP) showed the same increase in CFU-S proliferation as was seen before (Example 1, 3, 4) a slight increase in the erythroid progenitor number (BFU-E colonies) and a decrease in GM-CFU, which were completely abrogated by the incubation with INPROL. In addition, the abnormally high level of CFU-S proliferation was returned to 10% of CFU-S in S-phase of cell cycle. CFU-S hyperproliferation is known to be a feature of some mouse strains susceptible to viral leukemia induction, for example Balb/c mice (Table 4), and can also be observed in older animals (Table 4). The same redistribution of committed progenitors seen in TSP treated BDF1 mice is observed in Balb/c and in older (23–25 month old) BDF1, which have in common the abnormally high level of CFU-S proliferation. The correction of both the proliferation of CFU-S and the differentiation was induced by the incubation with INPROL. What is even more clinically relevant, the study showed that the in vivo injection of INPROL (2 μg/mouse) affected both proliferation of CFU-S and the ratio of erythroid (BFU-E) and GM-colonies (Table 4).

TABLE 4

INPROL Effect On CFU-S Differentiation Into
Committed Progenitors BFU-E and CFU-GM

| Donors Of Bone Marrow | pINPROL | Percent CFU-S Killed by $^3$HTdR | BFU-E | CFU-GM |
|---|---|---|---|---|
| BDF$_1$ Young | − | 12.0 ± 0.3 | 28.33 ± 1.91 | 46.22 ± 3.44 |
|  | + | 15.0 ± 1.3 | 22.00 ± 3.74 | 47.70 ± 3.72 |
| BDF$_1$ Old | − | 47.1 ± 1.9 | 43.75 ± 1.54 | 24.0 ± 1.33 |
|  | + | 11.4 ± 0.7 | 15.25 ± 1.45 | 44.0 ± 7.63 |
| BDF$_1$ Stimulated by TSP | − | 53.2 ± 1.6 | 32.67 ± 2.44 | 15.71 ± 2.28 |
|  | + | 7.2 ± 0.4 | 12.00 ± 1.83 | 35.50 ± 1.4 |
| Balb/C | − | 57.0 ± 1.9 | 47.60 ± 2.96 | 33.57 ± 3.45 |
|  | + | 23.0 ± 2.4 | 24.86 ± 2.53 | 70.60 ± 4.96 |

EXAMPLE 10

Immunostimulatory Activity of INPROL

It has been observed that the incubation of bone marrow cells containing a high proportion of proliferating CFU-S with INPROL not only changes the cycling of CFU-S, but also their differentiation, switching the predominantly erythroid differentiation in favor of granulocytic and lymphoid progenitors. This property of INPROL is of importance due to the immunosuppression side effects of cytotoxic chemotherapy or radiotherapy, as well as the immunosuppression accompanying hyperproliferative stem cell disorders and aging.

The example shows the direct effect of INPROL on the differentiation of immature precursors from the Lymphoid Long Term Culture (LLTC) established according to Wittlock & Witte (Ann. Rev. Immun. 3:213–35, 1985) into pre-B progenitors, measured by the formation of colonies in methylcellulose containing IL-7.

Figure 13:
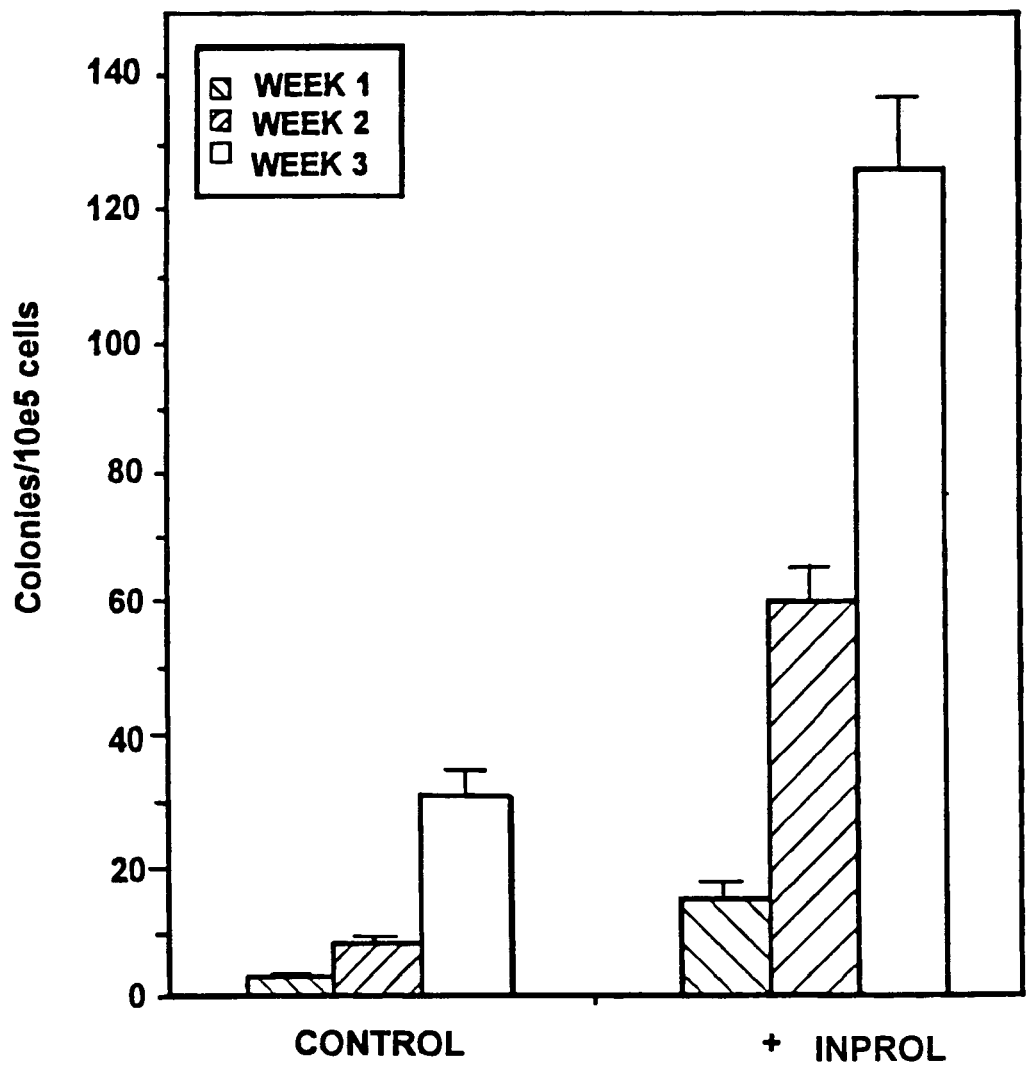
FIG. 13 shows suspension cells from lymphoid long-term culture which were taken every week, washed out, and plated with IL-7 (10 ng/ml) after preincubation with medium or pINPROL for 4 hours.

LLTC were established as described and fed with fresh LLTC-media (Terry Fox Labs., Vancouver, Canada) twice a week. Nonadherent cells were harvested once a week, washed free of factors and incubated for 4 hours with 25 ng/ml pINPROL or medium alone for control. After the incubation, the cells were washed and plated at a concentration of $10^5$ cells/ml in methylcellulose, containing 30% FCS, and 10 ng/ml of IL-7. Data from 3 weeks are shown in FIG. 13. The number of large pre-B colonies varied in control, increasing with time, but preincubation with INPROL always stimulated the growth of colonies 4 to 8 fold above the control level. This demonstrates an immunostimulatory property of INPROL which is of use in correcting immunodeficient states and in increasing desired immune responses, e.g., to vaccination.

EXAMPLE 11

INPROL Improves Repopulating Ability of Stem Cells—Long Term Culture Initiating Cells from Patient with CML Chronic myeloid leukemia (CML) is a lethal malignant disorder of the hematopoietic stem cell. Treatment of CML in the chronic phase with single-agent chemotherapy, combination chemotherapy, splenectomy, or splenic irradiation can control clinical signs and symptoms, but does not significantly prolong survival. As CML progresses from the chronic to the accelerated stage, standard therapy is not effective. At present, bone marrow transplantation (BMT) is the only known curative therapy for CML. Therapy with unrelated donor BMT is difficult due to histoincompatibility problems. Fewer than 40% of otherwise eligible CML patients will have a suitably matched related donor; therefore autologous transplantation is preferred. Ex vivo conditioning of autologous BMT for infusion together with the ability to select non-leukemic (Ph-negative) myeloid progenitors from Ph-positive patients growing in Long Term Culture (LTC) suggest the potential of autologous sources of normal stem cells to allow aggressive and effective therapy of CML.

In the context of BMT, a hematopoietic stem cell can be defined as one having the ability to generate mature blood cells for extensive periods. We have used the human LTC system developed by C. Eaves & A. Eaves both for quantitating stem cell numbers and as a means to manipulate them for therapeutic use. This involves seeding cells onto a pre-established, irradiated human marrow adherent layer; these cultures are then maintained for 5 weeks. The end point is the total clonogenic cell content (adherent+non-adherent) of the cultures harvested at the end of this time. Clonogenic cell output under these conditions is linearly related to the number of progenitors (Long Term Culture Initiating Cells (LTC-IC)) initially added; the average output from individual human LTC-IC is 4 clonogenic progenitors per LTC-IC. It has been shown previously that when marrow from patients with CML is placed under similar conditions, leukemic (Ph-positive) clonogenic cells rapidly decline. By using quantitation of residual normal LTC-IC, in patients with CML it is possible to select those likely to benefit from intensive therapy supported by transplantation of cultured autografts (Phillips et al., Bone Marrow Transplantation 8:477–487, 1991).

The following procedure was used to examine the effect of INPROL on the number of clonogenic cells (LTC-IC) among bone marrow transplant cells established from the peripheral blood of a patient with CML.

Cultures were initiated as long term cultures on pre-irradiated stroma. The peripheral blood of a healthy donor was used as the control. Peripheral blood cells from a CML patient were preincubated with or without pINPROL (25 ng/ml) for 4 hours, washed and placed in the LTC-IC system for 5 weeks to determine the control number of LTC-IC. For experiments, other, parallel cultures were established for 10 days. The mixture of adherent and non-adherent cells from cultures growing for 10 days was preincubated with or without pINPROL and placed on pre-established feeders for an additional 8 weeks. The number of LTC-IC from each experimental culture was estimated by plating both the adherent and non-adherent cells in methylcellulose with the appropriate growth factors (Terry Fox Laboratories, Vancouver, Canada) and counting the resulting total number of colony forming cells. The LTC-IC values obtained using this procedure were derived from assessment of the total clonogenic cells (CFC) content using the formula:

$$\#LTC\text{-}IC=\#CFC/4$$

Figure 14:
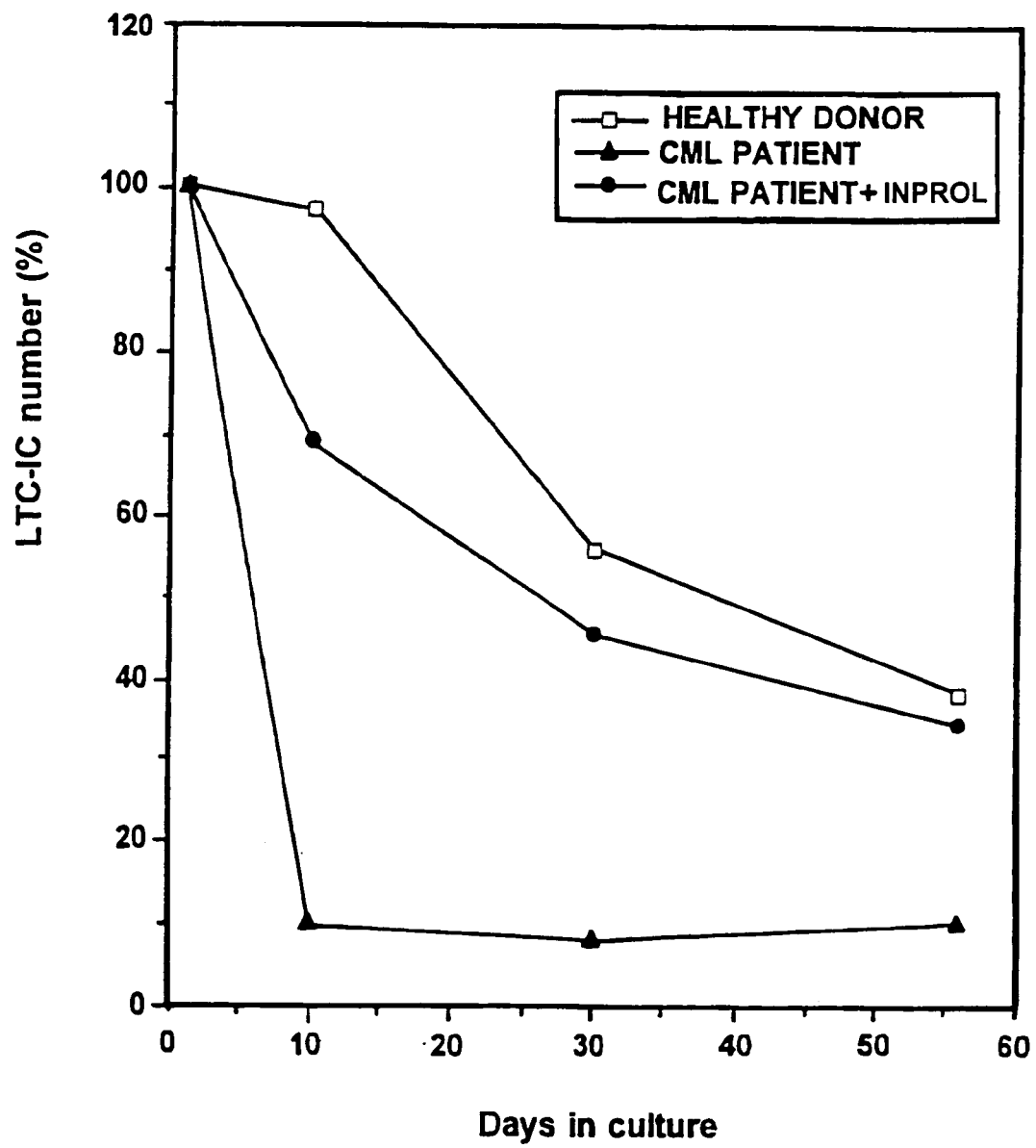
FIG. 14 shows improved repopulating ability of leukemic peripheral blood cells treated with pINPROL. Long term culture initiating cells (LTC-IC) were measured by plating adherent and nonadherent LTC cells with and without pIN-PROL, and scoring CFU-GM on day 7. Data are normalized to control values.

Data presented on FIG. 14 show that there was no loss in LTC-IC during the first 10 days of culture initiated from the healthy donor's bone marrow and approximately 30% of the number of input LTC-IC were still present after 5 weeks in culture. The number of the CML patient's LTC-IC was drastically reduced to about 8% during the 10 day period and did not recover during further incubation, while the preincubation of cells with INPROL increased the LTC-IC level to 30% of initial number and it was maintained during 8 weeks.

Clinically relevant applications of INPROL predicted by these preliminary data include their use in strategies for selectively improving the normal stem cell content of fresh or cultured marrow transplants, strategies for enhancing the recruitment of residual normal stem cells in vivo also protocols for transferring new genetic material into human marrow stem cells for the further transplantation into patients.

EXAMPLE 12A

A Method of Isolation of Immunoactive Inhibitor of Proliferation of Stem Cells from Bone Marrow Preparations The bone marrow was isolated from pigs' ribs. The ribs from the pigs' carcasses were separated and cleaned from the muscle fibers and fat, cut into pieces and the bone marrow was extracted by a hydropress manufactured by the Biophyzpribor. The bone marrow cells are separated by centrifugation in a centrifuge K-70 at 2,000 rpm for 20 minutes. The extract supernatant is then successively subjected to ultrafiltration through Amicon USA membranes XM-100, PM30, PM-50. According to the analysis by electrophoresis, the main component of the product is albumin (see FIG. 1).

Biochemical Purification

The bone marrow extract and protein components of the fractions were analyzed at every step of purification by gel electrophoresis in 10% polyacrylamide, containing 0.1% sodium dodecyl sulfate. Up to 7% of sodium dodecyl sulfate and up to 0.5–1% of mercaptoethanol were added to the samples which were incubated for 5 minutes at 70° C. prior to loading on the gel.

The electrophoresis was conducted at 20Y cm of the gel for five hours. Then the gel was stained in 0.25% Coomassie CBBC250 in a mixture of ethanol:water:acetic acid 5:5:1 for one hour at 20° C. and washed in several changes of 7% acetic acid. The activity of the product was evaluated by the method of inhibition of proliferation of stem hematopoietic cells (CFU-S). The method is detailed hereafter.

Stage 1. Purification by Precipitation with Ammonium Sulfate.

The activity was purified by precipitation with ammonium sulfate at 25% with saturation of 40 to 80% which was selected based on the results in Table 5.

TABLE 5

| Saturation (%) | 0–40 | 40–60 | 60–80 | 80–100 |
|---|---|---|---|---|
| Activity (%) | 37.2 − 35.4 = 1.8% | 37.2 − 1.8 = 35.4% | 37.2 − 12.8 = 24.4% | 37.2 − 26.1 = 11.1% |

The amount of the preparation used for testing after each step of purification was determined in accordance with the level of purification and equivalent to the dose of $2 \times 10^{-2}$ mg of the initial product. Activity was determined by the formula:

% Change = % Sa − % Sb where % Sa is % S in control
% Sb is % S after incubation with the test fraction.

The fraction was desalted in order to lower the concentration of ammonium sulfate 20 times before each testing of activity and before each following purification step.

Stage 2. The impure inhibitor from Stage 1 is applied after desalting and fractionated utilizing ion exchange chromatography, here DEAE 23 cellulose, and then eluted with a gradient of sodium acetate buffer (pH 6.0).

The active fractions of inhibitor elute between 3–5 mM.

Figure 2:
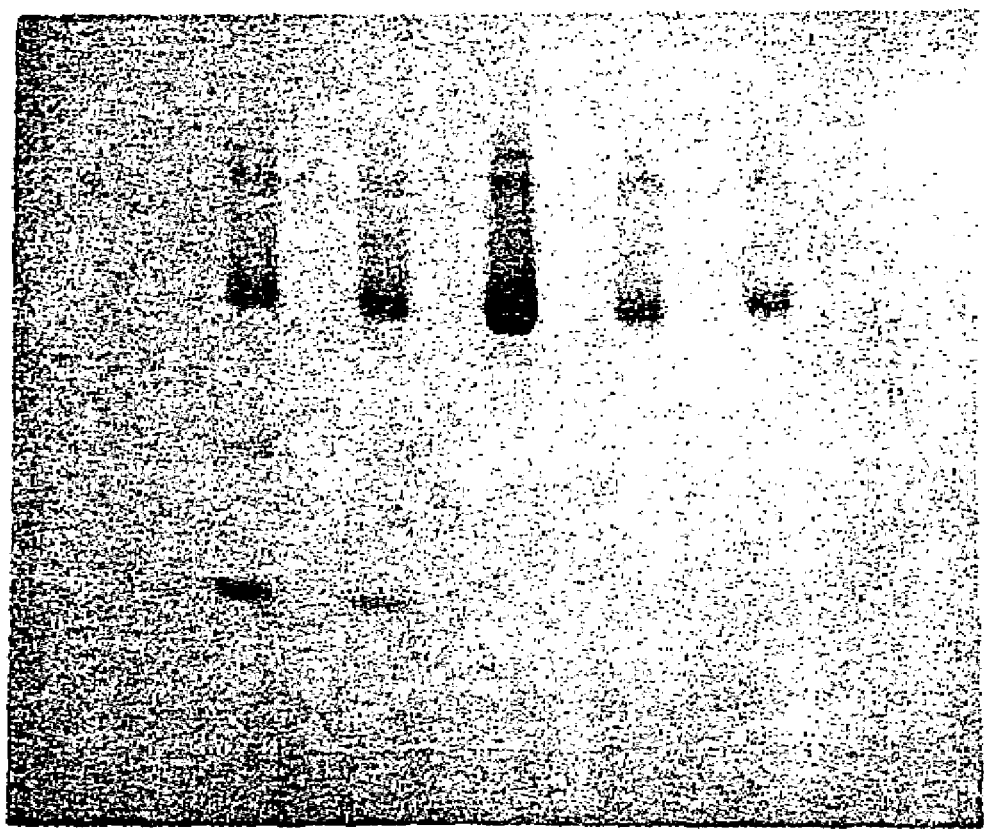

The volume of the column was 1 ml and speed of elution was 4 ml/hour. The detection was conducted by the chromatograph Millicrome at 230 and 280 nm. Fraction 1 (see FIG. 2) which exhibited the highest activity was isolated and eluted in 5 mM sodium acetate buffer (see Table 6).

TABLE 6

| | Fractions | | | | |
|---|---|---|---|---|---|
| | 1 | 2 | 3 | 4 | 5 |
| Activity | 46.3 − 0 = 46.3% | 46.3 − 14.1 = 32.2% | 46.3 − 42.1 = 4.2% | 46.3 − 19.6 = 26.7% | 46.3 − 45.1 = 1.2% |

Figure 3:
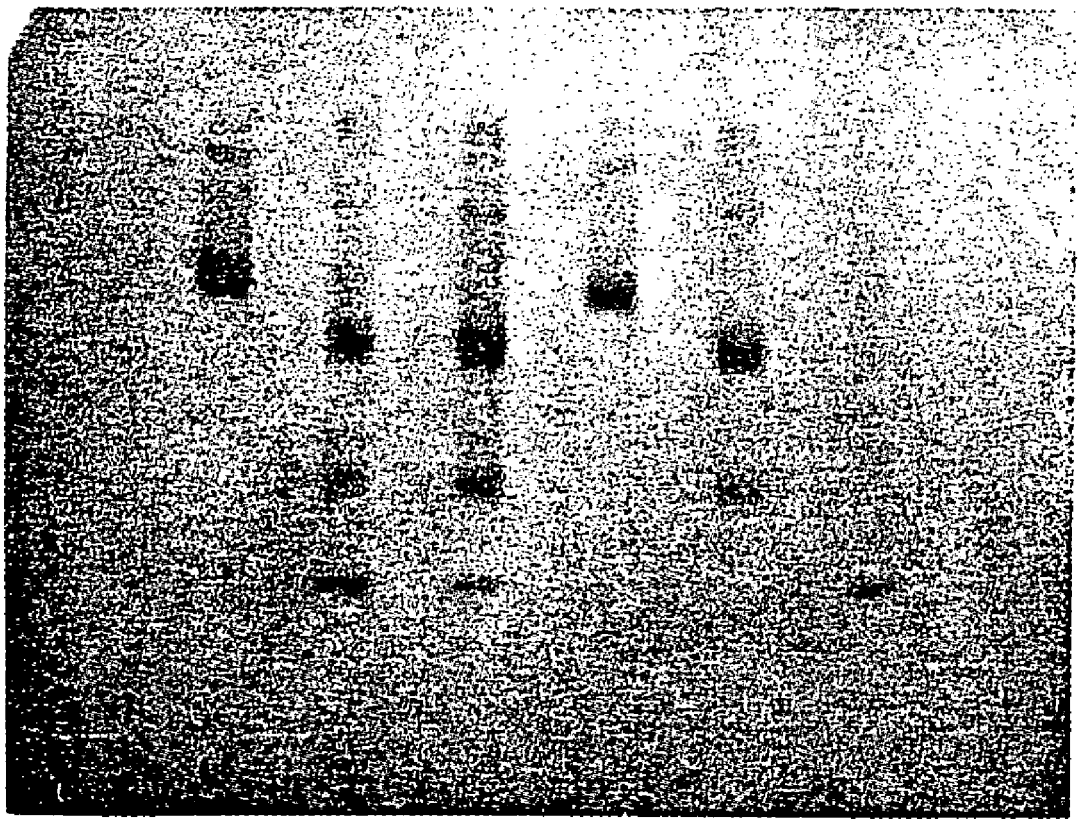

The electrophoresis data indicates that the main protein contaminant—albumin (see FIG. 3) is removed from this fraction which leads to an additional fourfold purification.

Stage 3. The partially purified inhibitor from Stage 2 is applied directly to a G-75 Sephadex column.

The volume of the column is 20 ml (20×1), the elution rate is 2 ml/hour. The elution buffer is 50 mM NaCl, 10 mM Tris-HCl, pH 7.5. Detection was conducted on a chromatograph Millichrome at 230 and 280 nm. Fraction 5 which had the highest activity was isolated.

TABLE 7

| | Fractions | | | | |
|---|---|---|---|---|---|
| | 1 | 2 | 3 | 4 | 5 |
| Activity | 42.2 − 19.1 = 23.1% | 42.2 − 35.2 = 7.0% | 42.2 − 21.5 = 20.7% | 42.2 − 38.8 = 3.4% | 42.2 − 0 = 42.2% |

Stage 4. Reverse-phase chromatography (Pharmacia FPLC System) utilizing Pro-REC columns is performed on an Ultrasfera matrix. Protein is eluted using 0.1% trifluoracetic acid in an acetonitrile gradient.

Figure 4:
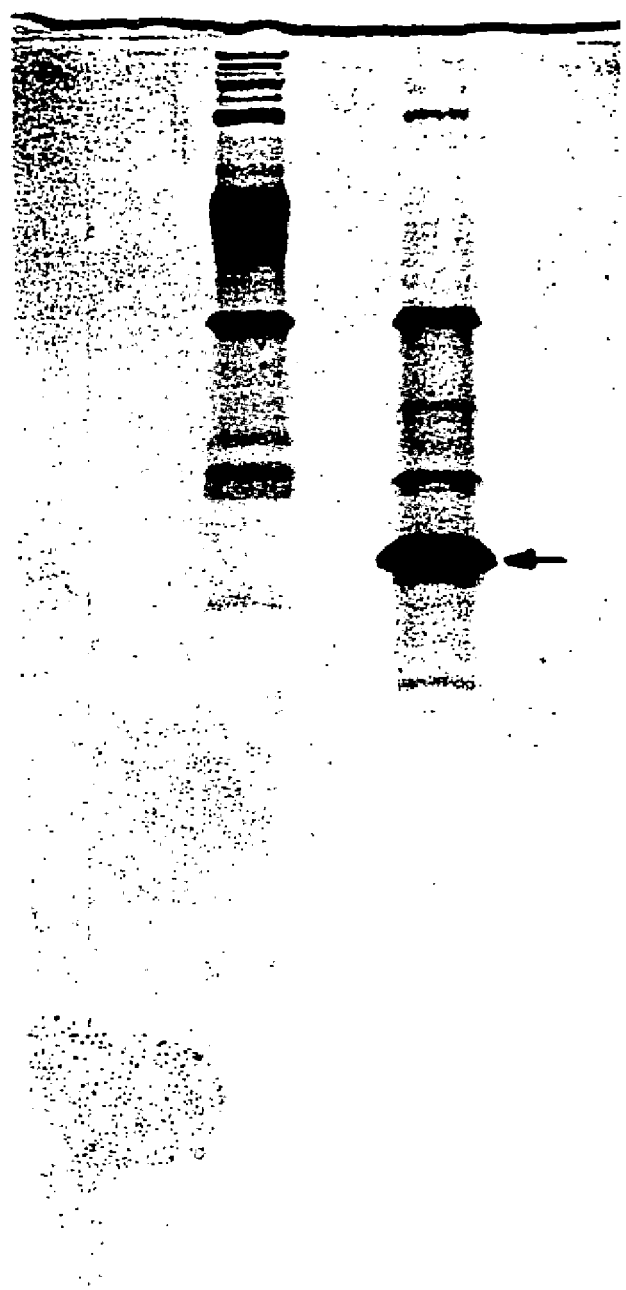

The homogeneity of a product with MW 16–17 kD is equal to 90% as was shown in analyzing the acrylamide/sodium dodecyl sulfate gel (see FIG. 6). The result is represented in FIG. 4. Activity is determined on fraction 5. The final yield of the product is 5%. As a result, the total amount of protein with MW 16 kD after the purification is 650 ng/ml of the initial product. During the purification process the product was submitted to heat incubation at 70° C. for several minutes but no loss of biological activity was detected.

EXAMPLE 12B

Alternative Method for Isolating Larger Quantities of INPROL

Initial Isolation

Ribs from fresh pig carcasses are cleaned of muscle fibers and fat, then cut to pieces and soaked in phosphate-buffered saline in the ratio 1:1 (weight/volume). The obtained mixture is crushed by hydraulic press to separate bone marrow from solid bone material.

The suspension of bone marrow cells is collected and filtered free of solid particles through four layers of the cheese-cloth. The filtrate is incubated at 56° C. for 40 minutes, then cooled in an ice-bath to 4° C. The resulting precipitate is removed by centrifugation at 10,000 g for 30 minutes at 4° C. and discarded.

The clarified supernatant is added dropwise during 30 minutes to 10 volumes of stirred ice-cold acetone containing 1% by volume of concentrated hydrochloric acid. The resulting mixture is kept at 4° C. for 16 hours for complete formation of the precipitate. Then the precipitate is pelleted by centrifugation at 20,000 g for 30 minutes at 4° C. This pellet is washed with cold acetone and dried.

HPLC Purification

The pellet is dissolved in HPLC eluent buffer A containing 5% acetonitrile (MeCN) and 0.1% triflouroacetic acid (TFA) to final protein concentration 8–10 mg/ml. This solution (0.5–0.6 ml) is loaded onto 250×4.6 mm HPLC column packed with Polisil ODS-300 (10 mcm) and equilibrated with the same buffer A.

The elution is accomplished by gradient of buffer B (90% MeCN, 0.1% TFA) in buffer A at the flow rate of 1 ml/min according to the following program:

| Time, min | % of B |
| --- | --- |
| 0 | 0 |
| 4 | 0 |
| 5 | 25 |
| 25 | 90 |

Figure 5:
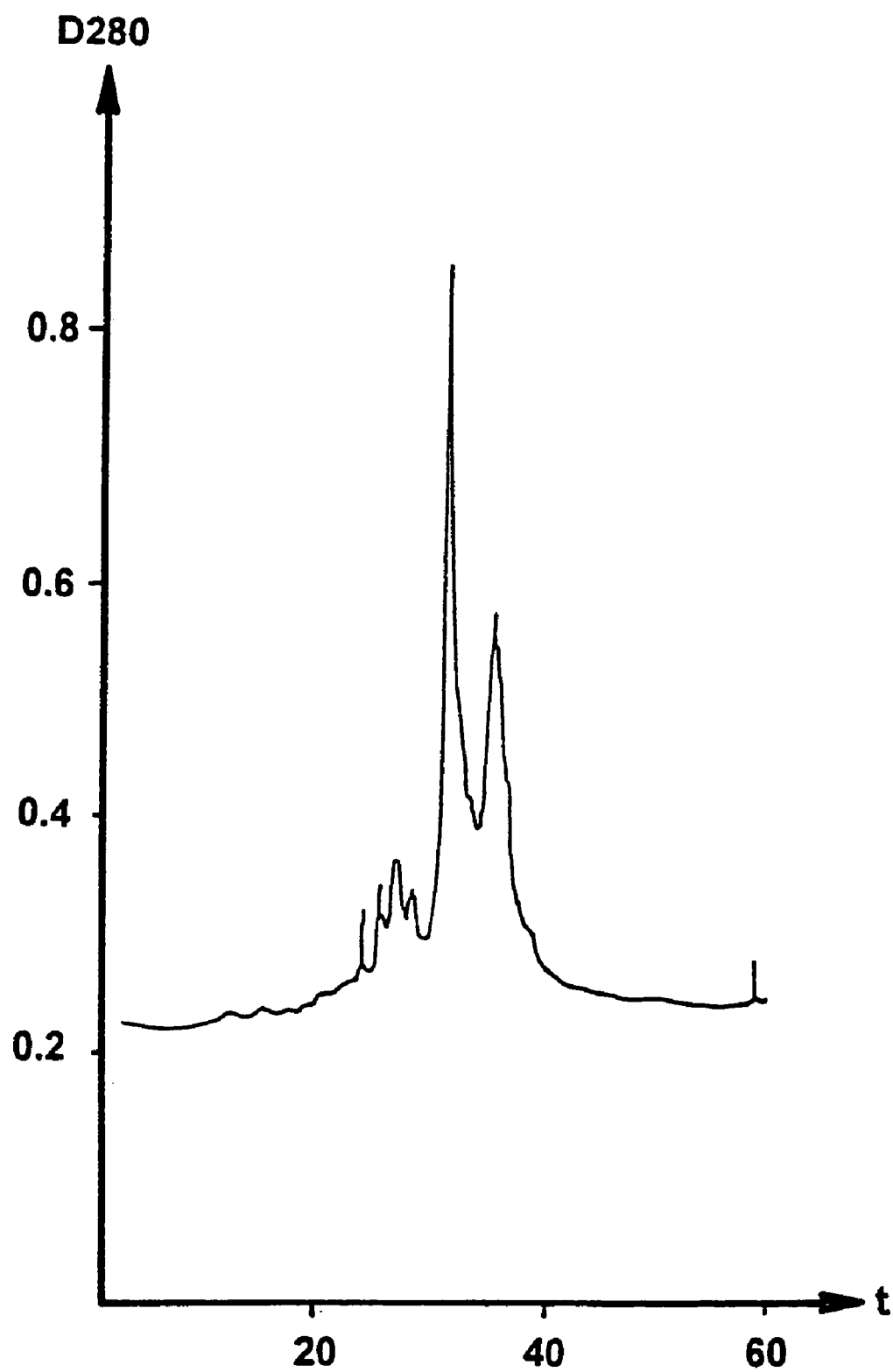
FIG. 5 shows a reverse phase HPLC chromatogram of the final purification.

An additional step of 100% B for 5 minutes is used to wash the column prior to re-equilibration. Then the column is equilibrated again for returning it to the initial state, and the next portion of the protein solution can be loaded. A typical chromatogram is shown in FIG. 5.

During the separation the column effluent is monitored at 280 nm for the detection of protein peak. Fractions containing the protein material are collected, separated peaks are pooled and rotary evaporated at 30° C. to dryness. The obtained residues are dissolved in distilled water and assayed by bioactivity test and by SDS-PAGE (14% gel. reducing conditions). The peak containing the active material is eluted between 70 and 80% of the buffer B and contains the main protein band of 16 kD and the traces of faster moving proteins as assayed by SDS-PAGE.

Figure 15A:
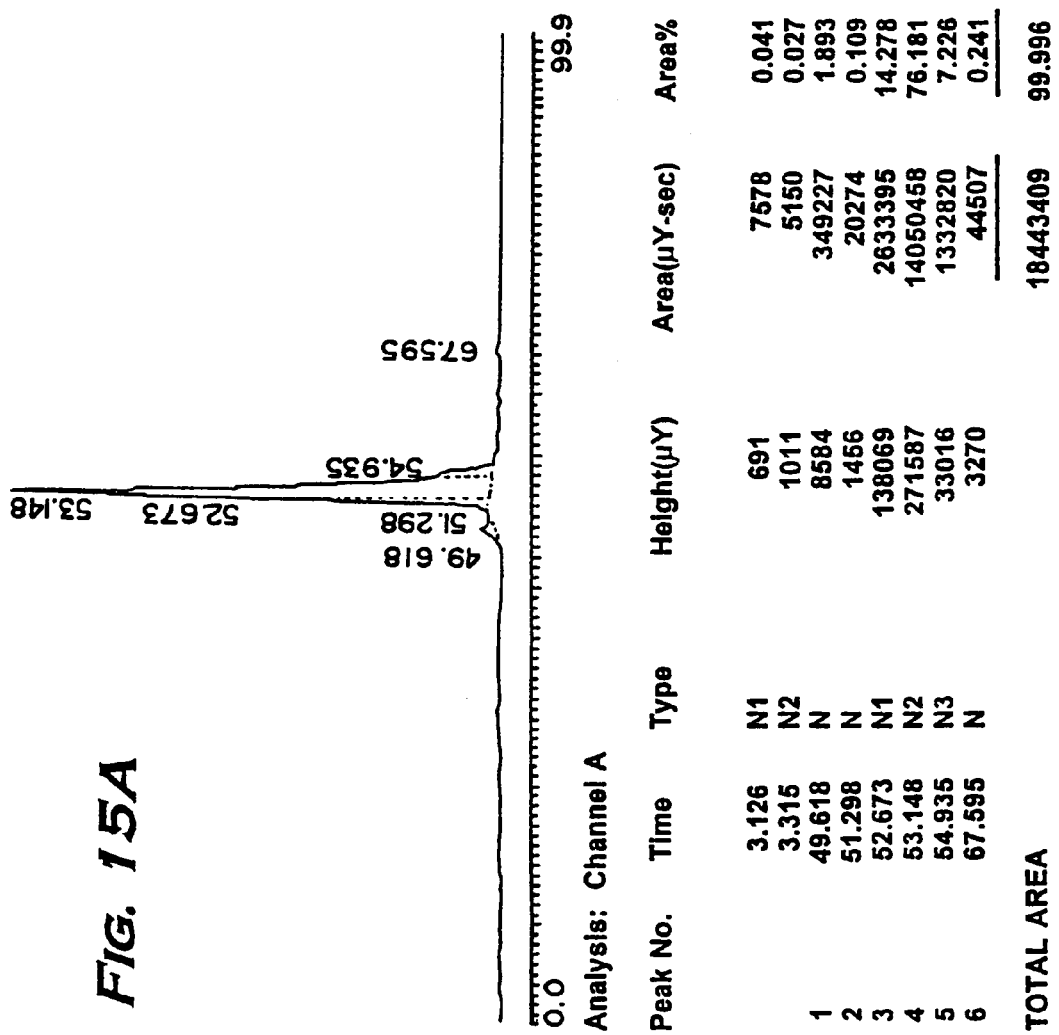
FIG. 15A shows a C4 reverse phase chromatogram of purified pINPROL eluting at 53% acetonitrile. Lane 1 is the crude material, Lane 2 is molecular weight markers and Lane 3 is the purified material.
Figure 15B:
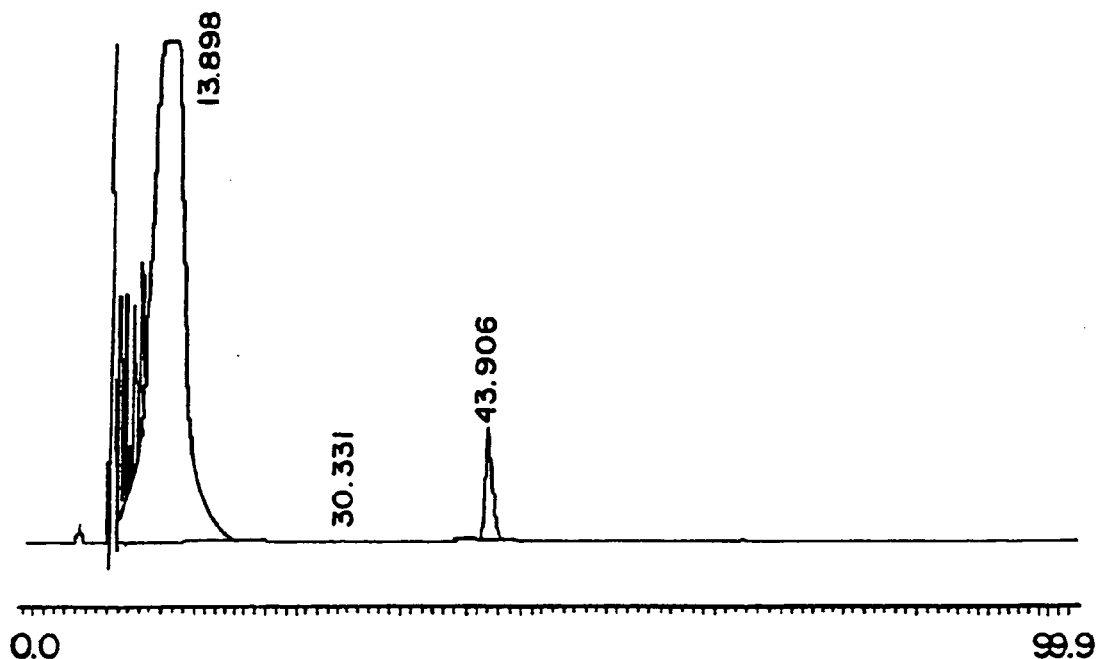
FIG. 15B shows a C4 reverse phase chromatogram of MIP-1α eluting at 43.9% acetonitrile.

An analysis of the material obtained by collecting only the second major HPLC peak is shown in FIG. 15(A and C). Material containing both peaks (e.g., FIG. 5) will be referred to herein as pINPROL Preparation 1 and those consisting of only the second peak will be referred to as pINPROL Preparation 2. 500 ug of this active, purified pINPROL Preparation 2 was loaded onto a C4 reverse phase column (Vydac) and eluted using a linear gradient of 595% acetonitrile in 0.1% trifluoroacetic acid. The material eluted as a single peak at 53% acetonitrile (FIG. 15A). When 250 μg of MIP-1α (R&D Systems), however, was run under indentical conditions, it eluted at 43.9% acetonitrile (FIG. 15B—note that earlier peaks prior to 14% acetonitrile are artifactual and due to air bubbles in the detector). Thus naturally occuring INPROL is substantially more hydrophobic than MIP-1α under these conditions. TGFβ is known to elute at lower concentrations than that observed for pINPROL under these conditions (Miyazono et al. J. Biol. Chem. 263:6407–15, 1988).

Figure 15C:
FIG. 15C shows an SDS-PAGE chromatogram of the crude pINPROL preparation and of the purified preparation after reverse phase.

A gel of the eluted pINPROL material is shown in FIG. 15C. Lane 1 is the crude material, Lane 2 is molecular weight markers and Lane 3 is the purified material. There are two major bands, one at approximately 14 kD and one at approximately 35 kD. It is believed that the 35 kD band is a multimeric form of the 14 kD band.

EXAMPLE 13A

Active INPROL Preparations Contain Hemoglobin Beta Chain pINPROL was prepared as shown in FIG. 5 (i.e., pINPROL Preparation 1 (see Example 12B)). The material was run on SDS-PAGE and transferred to nitrocelluose using standard techniques. The material was subjected to N-terminal sequence analysis using an ABI 477A protein sequencer with 120A Online PTH-AA analyzer using standard techniques. The following N-terminal sequence was obtained:
VHLSAEEKEAVLGLWGKVNVDEV . . .

Computer search of the protein databases reveal that this sequence has identity with the N-terminal sequence of the beta chain of porcine hemoglobin (cf. FIG. 16C).

EXAMPLE 13B

Active INPROL Preparations Contain Hemoglobin Alpha Chain

As shown in FIG. 15C, protein purified by collecting the second major peak shown in FIG. 5 (i.e., pINPROL Preparation 2) resulted in two major bands corresponding to molecular weights of approximately 15K and 30K, as well as several minor bands. SDS-PAGE gels were transferred to nitrocellulose using standard techniques and individual bands were excised and subjected to N-terminal sequence analysis as in Example 13A. The following N-terminal sequence was obtained for the 15 kD band:
VLSAADKANVKAAWGKVGGQ . . .

The 30 kD band was subjected to limited proteolytic digest and the following internal sequence was obtained: * * FPHFNLSHGSDQVK . . .

The first sequence shows identity with the N-terminal sequence of porcine hemoglobin alpha chain whereas the second sequence shows identity with residues 43–56 of the porcine hemoglobin alpha chain (see FIG. 16C for a sequence comparison of human, murine and porcine alpha and beta hemoglobin chains). Repeat sequencing of these bands as well as of some of the minor bands consistently yielded portions of the alpha globin sequence. Thus the various bands observed in FIG. 15C represent either fragments or aggregates of the porcine hemoglobin alpha chain.

EXAMPLE 13C

Further Characterizations of Porcine INPROL

Figure 17A:
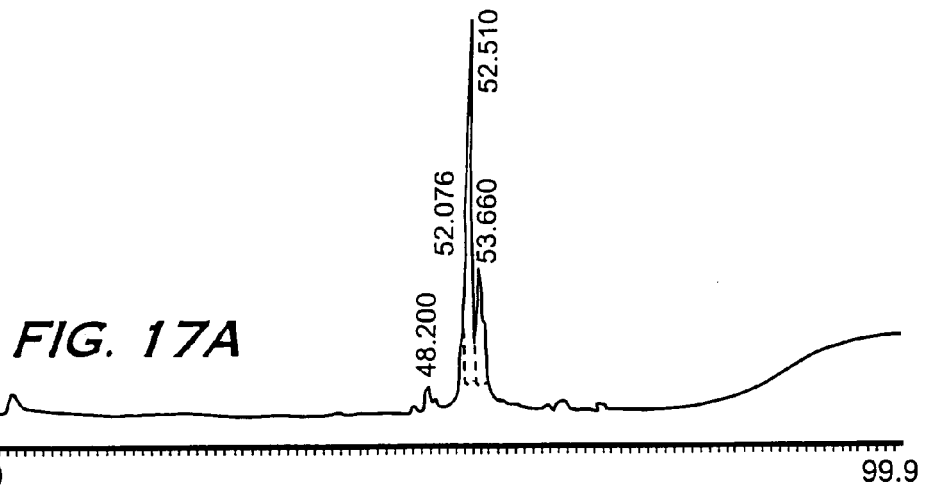
FIG. 17 shows a comparison of the C4 reverse-phase HPLC traces of pINPROL (FIG. 17A) and of crystallized pig hemoglobin (FIG. 17B).
Figure 17B:
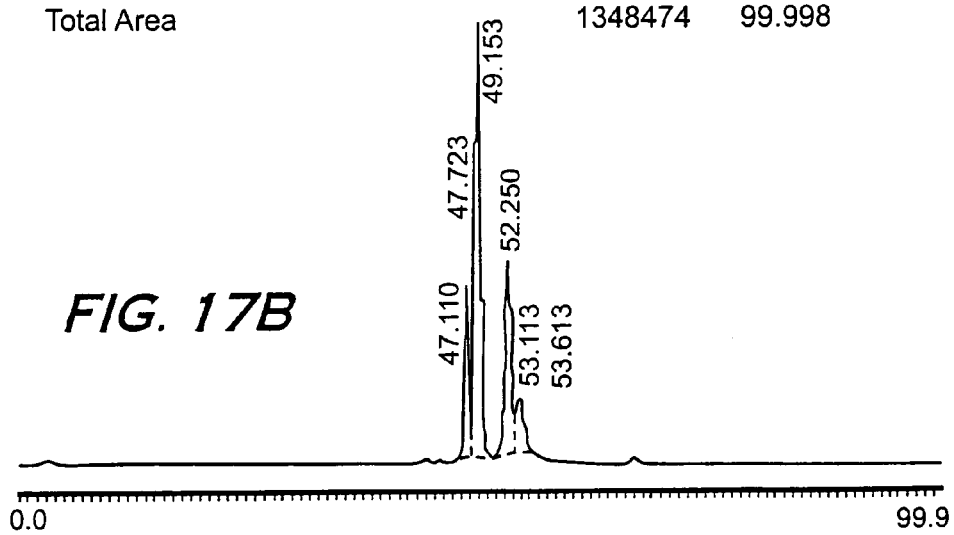

In order to further compare pINPROL to porcine hemoglobin, twice crystallized porcine hemoglobin was obtained from Sigma Chemical Company and subjected to reverse phase HPLC as described in Example 12B for FIG. 15. As can be seen in FIG. 17, the HPLC chromatogram of intact hemoglobin is similar to that seen for the pINPROL Preparation 1. Further, in a direct comparison, the pINPROL Preparation 2 shown in FIG. 17A (i.e., derived from the second peak of FIG. 5) is seen to overlap with that of the second two peaks of porcine hemoglobin (FIG. 17B), with retention times of 52.51 and 52.25 minutes for the major peaks, respectively. It should be noted that heme co-migrates with the first major peak in hemoglobin, in this case at 49.153 minutes; heme is therefore a component of pINPROL Preparation 1 but not of Preparation 2. This is confirmed by the lack of absorption of this pINPROL preparation at 575 nm, a wavelength diagnostic for the presence of heme.

Figure 18:
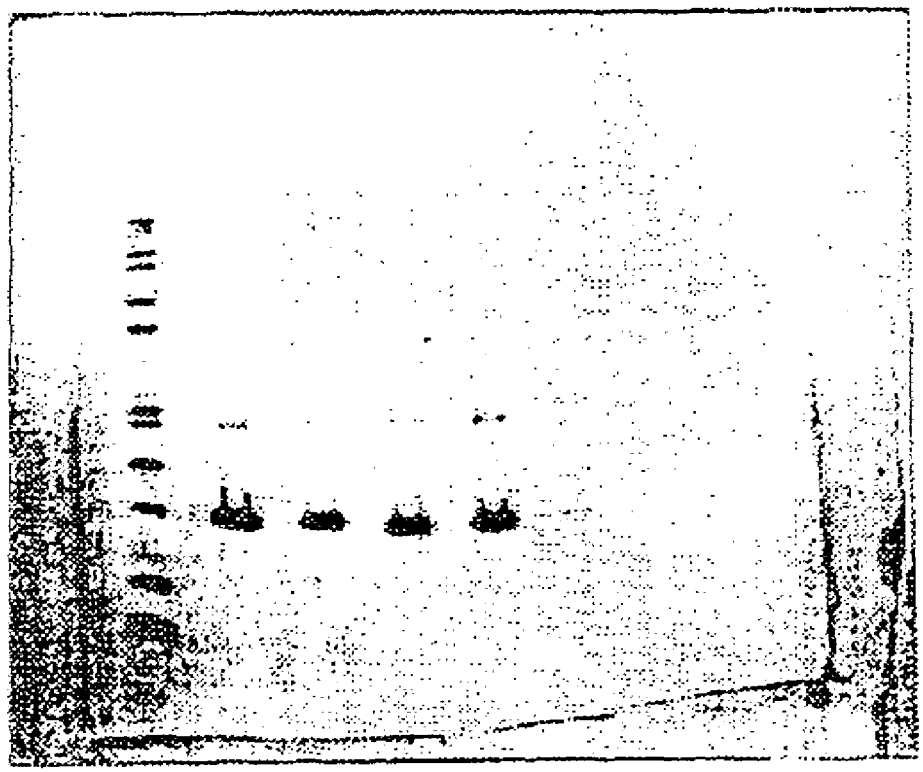
FIG. 18 shows an SDS-PAGE gel of fractions from a $C_4$ reverse phase HPLC separation of crystallized pig hemoglobin. Lane 1 shows molecular weight markers, Lane 2 shows Fractions 48–49, derived from the first peak (at 47.11 min), Lane 3 shows fractions 50–51, derived from the second peak (at 49.153 min), Lane 4 shows fractions 54–55, derived from the third peak (at 52.25 min) and Lane 5 shows fractions 56–57, derived from the fourth peak (at 53.613 minutes).

The predicted molecular weights of porcine hemoglobin alpha and beta chains are 15038 Daltons and 16034 Daltons, respectively. As can be seen in the SDS-PAGE chromatogram in FIG. 18, the first two peaks are composed of the higher molecular weight chain and the second two are composed of the lower molecular weight chain. Thus the first two peaks appeared to represent hemoglobin beta chain and the second two peaks to represent hemoglobin alpha chain.

Figure 21:
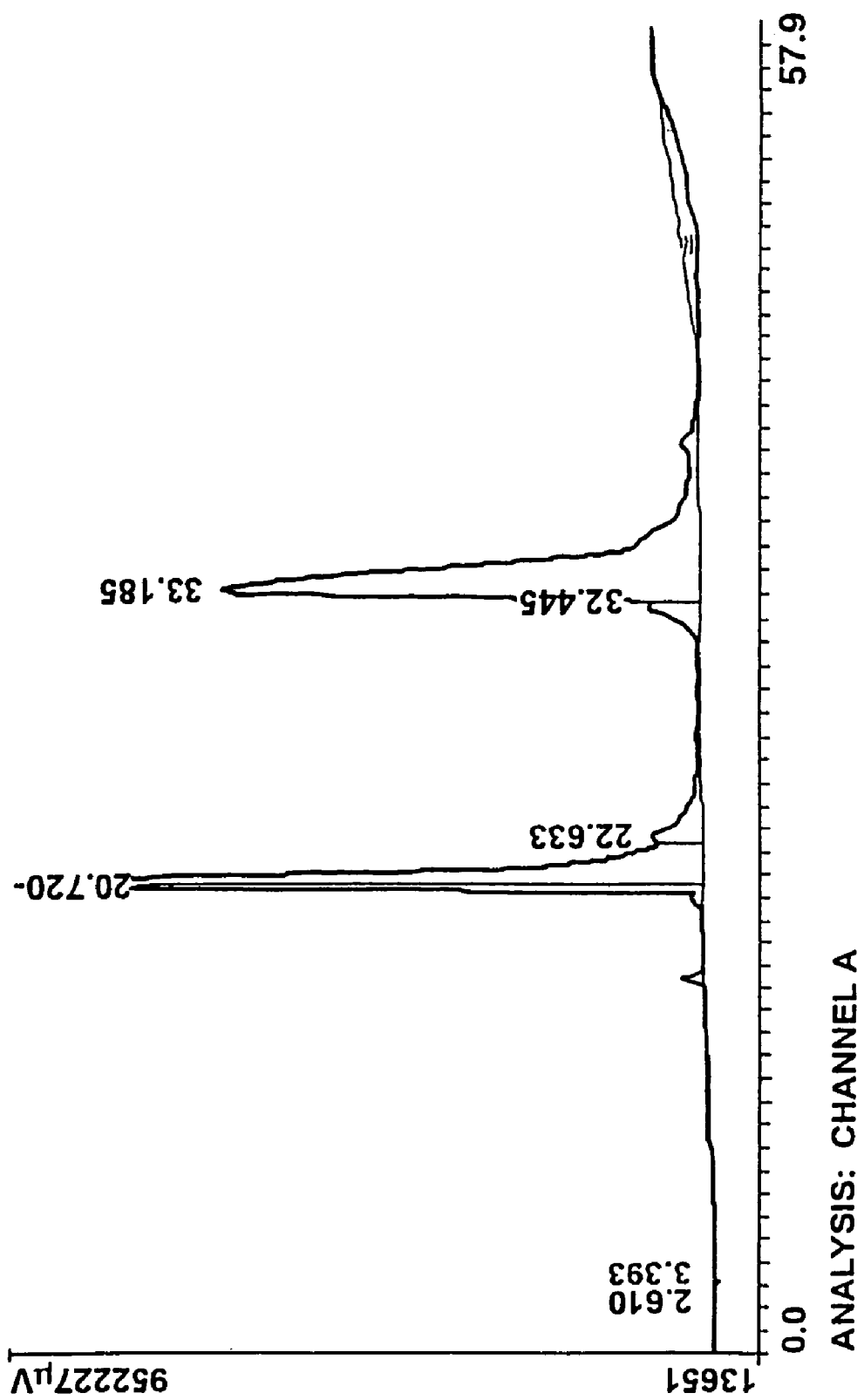
FIG. 21 shows the reverse phase separation of porcine hemoglobin using a shallow elution gradient.

Additional separations of porcine hemoglobin were carried out using a shallow elution gradient (FIG. 21). N-terminal analyses of these peaks demonstrated that the first peak is porcine alpha chain and the second porcine beta chain. Bioassay results confirm that both isolated hemoglobin chains are biologically active (e.g., Examples 14 and 15).

Figure 19A:
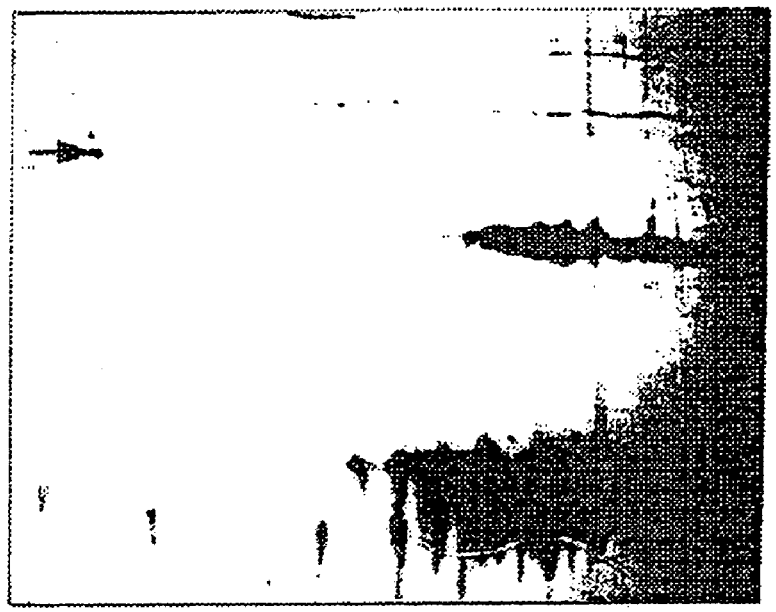
FIG. 19 shows a comparison of the 2-dimensional gel electrophoreses of pINPROL (FIG. 19A) and of purified pig beta hemoglobin (FIG. 19B).
Figure 19B:
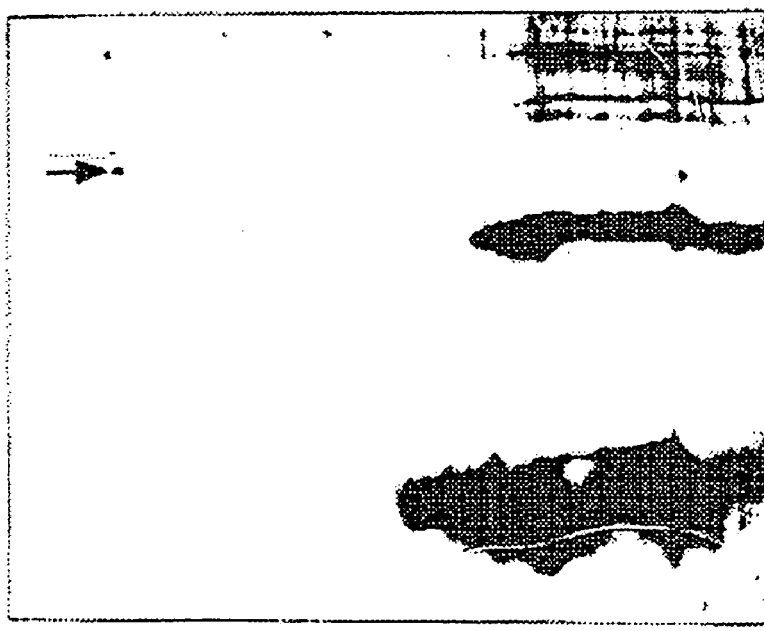

In order to further compare pINPROL Preparation 2 and hemoglobin beta chain, 2-dimensional electrophoreses were conducted (FIG. 19). As a first dimension, isoelectric focusing was carried out in glass tubes using 2% pH 4–8 ampholines for 9600 volt-hours. Tropomyosin (MW 33 kD, pI 5.2) was used as an internal standard; it's position is marked on the final 2D gel with an arrow. The tube gel was equilibrated in buffer and sealed to the top of a stacking gel on top of a 12.5% acrylamide slab gel. SDS slab gel electrophoresis was carried out for 4 hours at 12.5 mA/gel. The gels were silver stained and dried.

A comparison of the 2D electrophoretic patterns revealed only one or two minor spots that are different between HPLC purified hemoglobin beta chain and the pINPROL Preparation 2. Western analyses, using anti-porcine hemoglobin antibodies and either ID or 2D electrophoresis, confirm the presence of beta hemoglobin in the preparation. Thus the active pINPROL Preparation 2, prepared according to Example 12B, is substantially porcine hemoglobin beta chain.

EXAMPLE 14

Hemoglobin Alpha Chain, Hemoglobin Beta Chain or Intact Hemoglobin Exhibit Stem Cell Inhibitory Activity To confirm that hemoglobin beta chain has INPROL activity, a suicide assay using bone marrow from testosterone-treated mice was conducted using the methodology described in Example 1 using material purified as in Example 12B. As shown in Table 8, 15% of normal mouse bone marrow cells were killed as opposed to 36% in the testosterone-treated animals. As expected, this indicated that testosterone treatment increases the percentage of cells in cycle (thus rendering them more susceptible to killing—e.g., Example 1). In sharp contrast, cells from testosterone-treated animals incubated with either pINPROL or purified hemoglobin beta chain at 40 ng/ml showed a dramatic lowering of the percentage of cells in cycle from 36% to 0% and to 7%, respectively. The higher dose of 200 ng was less effective for both proteins. As a positive control, the previously characterized stem cell inhibitor MIP-1α reduced cycling to 13%.

A similar assay can be performed in vitro, using the cycling status of CFU-MIX instead of CFU-S. The assay is performed as described above for the CFU-S assay except that cytosine arabinoside (Ara C, 30 micrograms/ml) is used as the cycle-specific toxic agent instead of high dose tritiated thymidine (see B. I. Lord in *Haemopoiesis—A Practical Approach*, N. G. Testa and G. Molineux (Eds.), IRL Press 1993; Pragnell et al. in *Culture of Hematopoietic Cells*R. I. Freshney, I. B. Pragnell and M. G. Freshney (Eds.), Wiley Liss 1994) and a mouse strain with high endogenous cycling rates (Balb/c) is used instead of testosterone-treated $BDF_1$ mice. As shown in Table 9, highly purified porcine beta chain, or highly purified porcine alpha chain, are both active in this assay. Note that in this assay, cycling levels for cells treated with pINPROL occasionally have negative numbers, indicating that there are even more colonies in the Ara C treated pool than in the non-treated pool.

Figure 20:
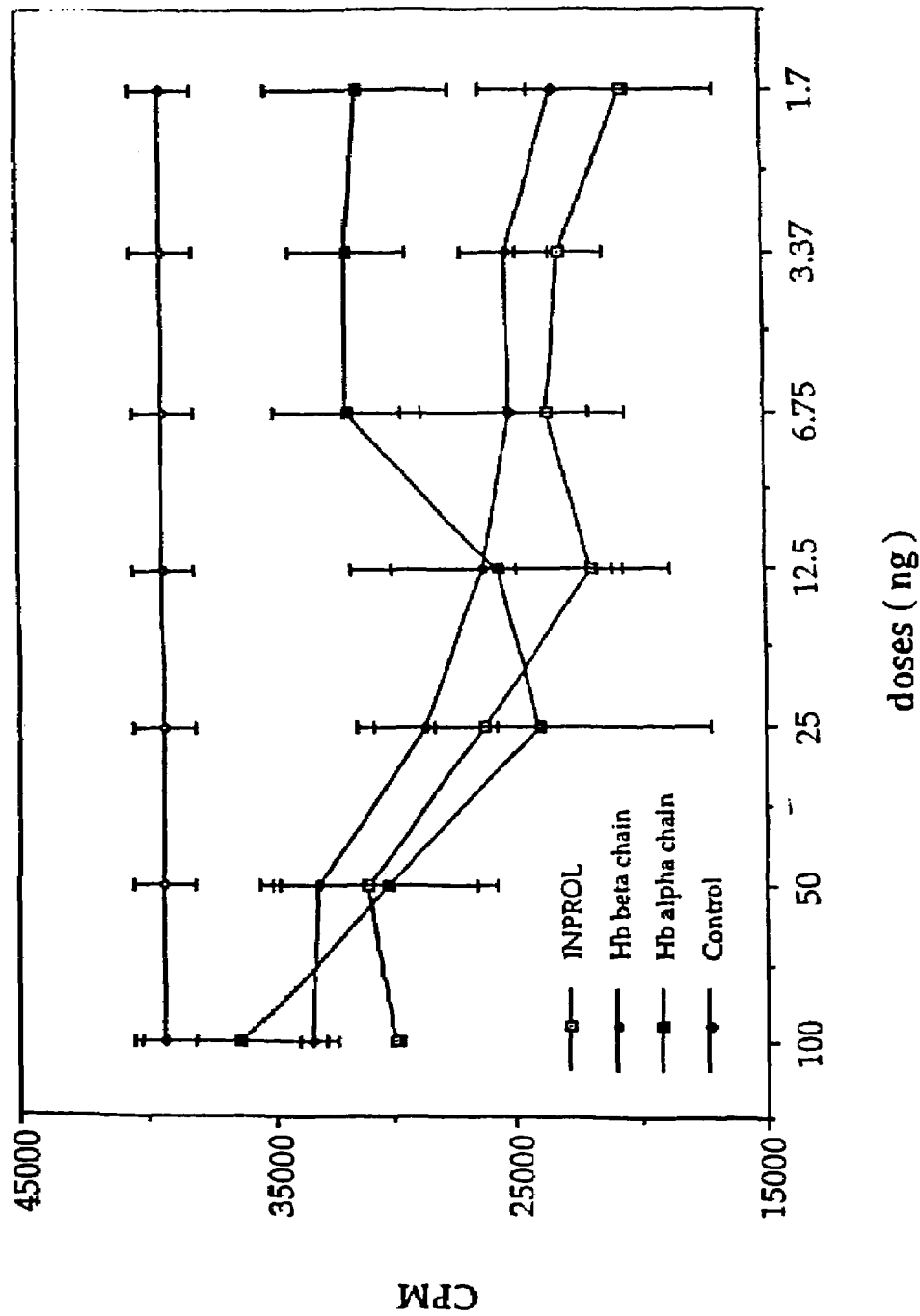
FIG. 20 shows a comparison of the effects of purified pig alpha hemoglobin, beta hemoglobin or pINPROL in the FDCP-MIX assay.

As described in Example 2, pINPROL inhibits the proliferation of the murine stem cell line FDCP-MIX in a tritiated thymidine uptake assay. FIG. 20 demonstrates that purified hemoglobin alpha or beta chains are both active in this assay, with inhibitions seen at <2 ng/ml.

The foregoing provides evidence that the beta chain of porcine hemoglobin exhibits INPROL activity. Other data (e.g., Table 9, FIG. 20) demonstrate that isolated alpha chain, as well as intact hemoglobin, are also active as stem cell inhibitors. Active preparations also include mixtures of alpha and beta chains (e.g., FIG. 5).

The observations that isolated alpha globin chain and/or isolated beta globin chain are active indicate that the activities described here do not require an intact three-dimensional hemoglobin structure. Fragments of alpha and beta chain are also active as stem cell inhibitors and stimulators.

TABLE 8

| Treatment | % Kill |
| --- | --- |
| NBM[1] | 15 |
| TPBM[2] | 36 |
| pINPROL | |
| 200 ng/ml | 23 |
| 40 ng/ml | 0 |
| Hbg[3] | |
| 200 ng/ml | 25 |
| 40 ng/ml | 7 |
| MIP-1α 200 ng/ml | 13 |

[1]NBM = Normal Bone Marrow
[2]TPBM = Bone marrow from testosterone-treated mice
[3]Hbg = $C_4$ Reverse-phase purified porcine hemoglobin beta chain (derived from 2X crystallized pig hemoglobin)

TABLE 9

| Treatment | % Kill |
| --- | --- |
| Control[1] | 43 |
| Porcine alpha chain[2] | −4 |
| Porcine beta chain[2] | −14 |

[1]Control - Bone marrow from Balb/c mice
[2]100 ng/mL (Purified as in FIG. 21)

EXAMPLE 15

Purified INPROL Purified Porcine Alpha Hemoglobin or Purified Porcine Beta Hemoglobin are Active In Vivo In order to test the ability of purified porcine hemoglobin chains to act in vivo, $BDF_1$ mice were injected with testosterone propionate as described in Example 1. Twenty four hours later, mice received 500 ng of either pINPROL, porcine hemoglobin alpha chain (purified from peripheral red blood cells as in FIG. 21), porcine beta chain (purified from peripheral red blood cells as in FIG. 21) or the equivalent volume of carrier intravenously. Forty eight hours later the bone marrow from each mouse was harvested and the CFU-MIX assay conducted as described in Example 14. As shown in Table 10, pINPROL, pig alpha chain and pig beta chain all were active in vivo, reducing the percent of CFU-MIX in cycle to basal levels.

TABLE 10

| Treatment | % Kill |
|---|---|
| Control[1] | 45 |
| pINPROL[2] | 5 |
| Porcine alpha chain[2] | 5 |
| Porcine beta chain[2] | −5 |
| Basal[3] | 4 |

[1]Control - Bone marrow from testosterone-treated $BDF_1$ mice
[2]100 ng/ml
[3]Basal - Bone marrow from untreated $BDF_1$ mice

EXAMPLE 16

Purified Human Hemoglobin Alpha Chain, Biotinylated Human Hemoglobin Alpha Chain, Biotinylated Human Hemoglobin Beta Chain, Human Hemoglobin Gamma Chain and Human Hemoglobin Delta Chain all Exhibit Stem Cell Inhibitory Activity In Vitro Human hemoglobin was obtained either from Sigma Chemical Corporation or was isolated by standard means from adult human peripheral blood or umbilical cord blood. Individual chains were isolated by reversed-phase HPLC in a similar manner as that described above for porcine alpha and beta chains (see B. Masala and L. Manca, Methods in Enzymology vol. 231 pp. 21–44, 1994). Purified alpha, beta, gamma and delta chains were obtained. For biotinylated alpha and beta chains, 1 mg of adult human hemoglobin was treated with 37 μg of NHS LC Biotin (Pierce) and the chains separated by reverse phase chromatography as above.

As shown in Tables 11, 12 and 13, purified human alpha, biotinylated human alpha, biotinylated human beta, human gamma and human delta hemoglobin chains are all active in the CFU-MIX cycling assay.

TABLE 11

| Treatment | % Kill |
|---|---|
| Control[1] | 49 |
| Human alpha chain[2] | −1 |
| Human beta chain[2] | 41 |
| Human gamma chain[2] | −63 |

[1]Control - Bone marrow from Balb/c mice
[2]100 ng/ml

TABLE 12

| Treatment | % Kill |
|---|---|
| Control[1] | 47 |
| Human gamma chain[2] | 12 |
| Human delta chain[2] | −4 |

[1]Control - Bone marrow from Balb/c mice
[2]100 ng/ml

TABLE 13

| Treatment | % Kill |
|---|---|
| Control[1] | 68 |
| Human alpha chain[2] | 19 |
| Biotinylated alpha chain[2] | 7 |
| Human beta chain[2] | 55 |
| Biotinylated beta chain[2] | 25 |

[1]Control - Bone marrow from Balb/c mice
[2]100 ng/ml

EXAMPLE 17

Purified Human Alpha Chain, Alpha-Beta Dimer or Hemoglobin are Active In Vivo Purified human alpha chain, alpha-beta dimer or hemoglobin were tested in an in vivo assay as described in Example 15. As shown in Table 14, each of these were active at a concentration of 500 ng/mouse.

TABLE 14

| Treatment | % Kill |
|---|---|
| Control[1] | 49 |
| Human alpha chain | −22 |
| Human alpha-beta dimer | 14 |
| Human hemoglobin | −31 |

[1]Control - Bone marrow from testosterone-treated $BDF_1$ mice

EXAMPLE 18

Porcine INPROL is Active on Human Mononuclear or CD34+ Cord Blood Cells In Vitro In order to investigate the ability of purified INPROL from porcine bone marrow to affect cycling on human progenitors, umbilical cord blood cells were obtained. Either the total mononuclear cell fraction obtained after separation on Ficoll or the CD34+ fraction obtained after fractionation on anti-CD34 affinity columns (CellPro Inc.) was used. Cells were incubated for 48 hours in vitro in the presence of interleukin 3 (IL-3) and stem cell factor (SCF) (100 ng/ml each) in order to ensure that the early stem cells were in cycle. After this preincubation, cycling assays were conducted as described in Example 14 for the mouse except that CFU-GEMM (instead of CFU-MIX) were counted on Day 18 after plating. As shown in Table 15, porcine INPROL inhibited cycling of CFU-GEMM in either the bulk mononuclear cells or in the CD34+ fraction.

TABLE 15

| Treatment | | % Kill |
|---|---|---|
| Mononuclear Cells | Control | 93 |
| | pINPROL[1] | 16 |
| CD34+ Cells | Control | 41 |
| | pINPROL[1] | 21 |

[1]100 ng/ml

EXAMPLE 19

Purified Human Alpha Hemoglobin is Active on Human CFU-GEMM

Human umbilical cord blood mononuclear cells were obtained and incubated in IL-3 and SCF and used in a cycling assay as described in Example 18. As shown in Table 16, both porcine INPROL purified from bone marrow and human alpha hemoglobin, purified from peripheral blood, were active in this assay.

TABLE 16

| Treatment | % Kill |
|---|---|
| Control | 100 |
| pINPROL[1] | −6 |
| Human alpha chain[1] | −23 |

[1]100 ng/ml

EXAMPLE 20

Peptides Obtained from Human Alpha Hemoglobin and from Human Beta Hemoglobin Sequences are Active To identify active peptide sequences, the three dimensional structure of myoglobin (which is inactive in this assay) was superimposed on the native three dimensional structure of the alpha chain present in adult human hemoglobin using a computer modeling program. Two peptides (representing amino acids 43–55 and 64–82, which are regions which are structurally different from myoglobin in three-dimensional space) were identified as having activity in the CFU-MIX cycling assay. In order to more closely approximate the loop found in the native alpha chain, a cyclic derivative of the 43–55 peptide (c43–55) (utilizing a disulfide bond) was also synthesized and found to be active.

The sequence of these peptides is as follows:

```
43-55    Phe-Pro-His-Phe-Asp-Leu-Ser-His-Gly-Ser-Ala-Gln-Val
         ("Peptide 43-55")

c(43-55) Cys-Phe-Pro-His-Phe-Asp-Leu-Ser-His-Gly-Ser-Ala-Gln-Val-Cys
         (where the two Cys residues are disulfide-bonded) ("Cyclic Peptide 43-55")

64-82    Asp-Ala-Leu-Thr-Asn-Ala-Val-Ala-His-Val-Asp-Asp-Met-Pro-Asn-Ala-Leu-Ser-
         Ala ("Peptide 64-82")
```

Two hemorphin sequences, hemorphin 10 (amino acids 32–41 of the beta chain sequence) and hemorphin 7 (amino acids 33–40) were tested and found to be active.

The sequences are as follows:

```
Hemorphin 10
Leu-Val-Val-Tyr-Pro-Trp-Thr-Gln-Arg-Phe

Hemorphin 7
Val-Val-Tyr-Pro-Trp-Thr-Gln-Arg
```

To test the activity of these sequences, the CFU-MIX cycling assay was conducted as described in Example 14. As shown in Tables 17–19, these peptides all are active in this assay.

TABLE 17

| Treatment | % Kill |
|---|---|
| Control | 47 |
| pINPROL[1] | 0 |
| Peptide (43–55) | |
| 100 ng/ml | 2 |
| 10 ng/ml | 18 |
| 1 ng/ml | 11 |

[1]100 ng/ml

TABLE 18

| Treatment | % Kill |
|---|---|
| Control | 43 |
| Peptide (43–55)[1] | 5 |
| Peptide (64–82)[1] | 9 |
| Hemorphin 10[1] | 1 |
| Hemorphin 7[1] | 0 |

[1]All peptides tested at 100 ng/ml

TABLE 19

| Treatment | % Kill |
|---|---|
| Control | 47 |
| Cyclic Peptide 43–55[1] | 0 |

[1]Tested at 100 ng/ml

EXAMPLE 21

A Peptide Fragment Obtained from Human Alpha Hemoglobin by Formic Acid Cleavage is Active Human alpha hemoglobin chain has a formic acid cleavage site between amino acid positions 94 and 95 (Asp-Pro). Cleavage was obtained by incubating purified human alpha chain (as in Example 16) at a concentration of 1 mg/ml in 70% formic acid for 72 hours at 37° C. The 1–94 fragment was purified from the uncleaved alpha chain and the 95–141 fragment by reverse-phase HPLC as in Example 16; fractions were followed using SDS-PAGE (as in Example 22). Identity of the purified 1–94 protein fragment was confirmed by electrospray ionization mass spectrometry.

To assess the stem cell inhibitory activity of this fragment, the CFU-MIX cycling assay is used as in Example 14:

TABLE 20

| Treatment | % Kill |
| --- | --- |
| Control[1] | 50 |
| Human Alpha[2] | 12 |
| 1-94 fragment[3] | 0 |

[1]Balb/c bone marrow
[2]Purified, non-recombinant human alpha hemoglobin, as in Example 16 (100 ng/ml)
[3]Purified formic-acid cleaved protein, as in the present Example (100 ng/ml)

EXAMPLE 22

Expression of Hemoglobin Alpha Chain, Polypeptide 1–141, Polypeptide 1–97, Peptide 43–55 and Peptide c(43–55) in *E. coli* as Ubiquitin Fusions Genes for peptides 43–55 ("p13") and c43–55 ("p15") (as in Example 20) were synthesized by annealing the corresponding oligonucleotides according to the optimal *E. coli* codon usage (Anderssen and Kurland, Micro. Reviews 54:198–210, 1990). The gene for the intact human alpha hemoglobin chain ("p141") was obtained by designing a set of oligos to PCR amplify from a human bone marrow cDNA pool (Clontech, Palo Alto, Calif.). The gene for the 1–97 fragment ("p1–97") was obtained by PCR amplification of the plasmid containing the p141 gene after appropriate subcloning.

Figure 22A:
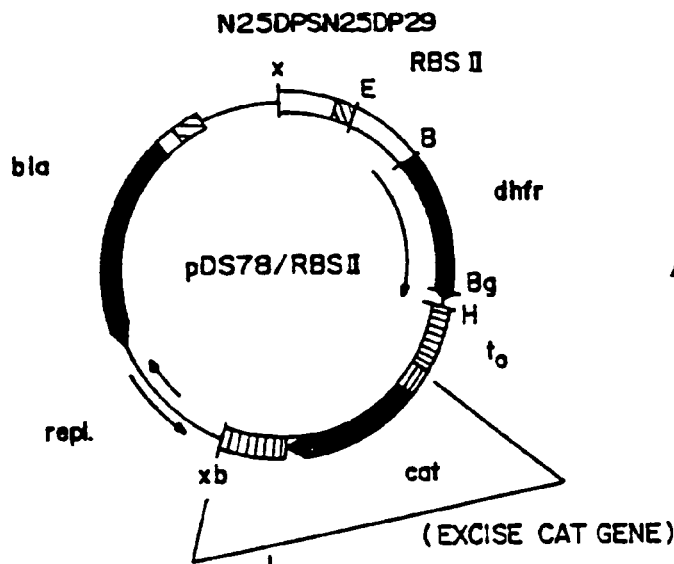
FIG. 22A shows the plasmid from Hochuli et al., (1988)
Figure 22B:
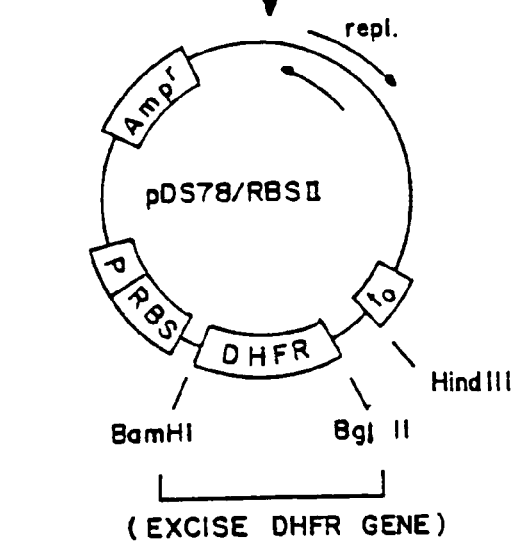
FIG. 22B shows the plasmid of Loetscher et al., (1991)
Figure 22C:
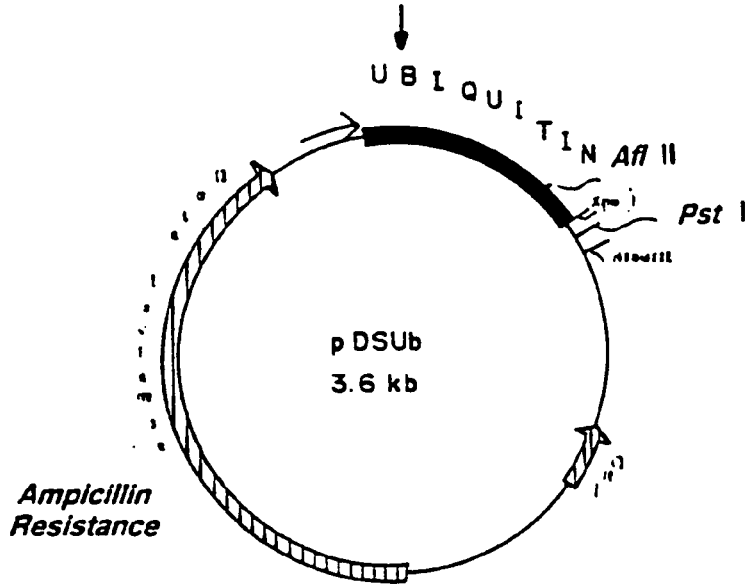
FIG. 22C shows the pDSUb plasmid.

The above genes were expressed as ubiquitin fusion proteins (see U.S. Pat. Nos. 5,132,213; 5,196,321 and 5,391,490 and PCT WO 91/17245). The host strain, *E. coli* DH5αF'IQ (Life Technologies, Inc., Gaithersburg, Md.) was transformed with the ubiquitin expression vector, pDSUb, containing the appropriately, synthesized gene (above). pDSUb is a derivative of pDS78/RBSII that expresses human ubiquitin (FIG. 22A) (Hochuli et al., Biotechnology 6:1321–5, 1988). Loetscher et al. (JBC 266:11213–11220, 1991) modified pDS78/RBSII by excising the chloramphenicol acetyl transferase (CAT) sequences from the Hochuli plasmid and religating the plasmid (FIG. 22B). A synthetic ubiquitin gene was constructed by pairwise annealing of kinased synthetic oligonucleotides encoding human ubiquitin with codon usage optimized for bacterial expression. pDSUb was then constructed by inserting the synthetic ubiquitin gene, comprised of assembled oligonucleotides, into a Klenow blunted Bam HI-Bgl II digest of the derivatized pDS78/RBSII. The resulting plasmid, pDSUb (FIG. 22C), was shown to express ubiquitin at a high level in *E. coli*.

The plasmid containing p97 and the one containing p141 were constructed by inserting Afl II-Pst I digested PCR products encoding the p97 or p141 protein and fusion junction, in a directional cloning, into pDSUb that had been digested with Afl II and Pst I. Similarly, the plasmid containing p13 and the one containing p15 were constructed by inserting kinased and annealed oligonucleotides, bearing the appropriate sticky ends and encoding the peptide and fusion junction, into Afl II-Pst I digested pDSUb.

Transformants were selected with 100 μg/ml ampicillin, 5 μg/ml neomycin, with colonies appearing after two days at 30° C. Transformants were screened by PCR across the insertion site. Colonies containing the correctly sized insert were then screened for expression of a fusion protein of the appropriate size by SDS-PAGE (see below). The ubiquitin fusion was overexpressed by the addition of IPTG which titrates the lac repressor, removing it from the promoter of pDSUb (DH5αF'IQ contains an upregulated lacIq gene on the F' factor which is selected with 10 μg/ml neomycin.)

Plasmid DNA from clones that exhibited an overexpressed, induced ubiquitin fusion protein was prepared and sequenced by the dideoxy method using the Sequenase Version 2.0 kit (United States Biochemical.) Positive clones were then frozen down and stored in glycerol at −80° C. Positive clones were maintained on LB plates containing ampicillin (100 μg/ml), neomycin (10 μg/ml) and 1% glucose, at 30° C. They were streaked weekly for up to 10 passages, after which a fresh streak was taken from a frozen seed vial for serial culture, to insure strain authenticity.

To obtain protein for assay, 100 ml starter cultures in 250 ml shake flasks were grown from single colonies by overnight incubation (16–20 hours) in 2×YT medium with ampicillin (100 μg/ml), neomycin (10 μg/ml) and 1% glucose. Shaker flask cultures were maintained at 30° C. and 250 rpm in a New Brunswick environmental shaker incubator. The next morning the culture was diluted to 1 liter with medium. Cells were induced by IPTG addition to 1 mM (final dilution) at $OD_{600}$=0.5 and harvested at $OD_{600}$=0.8 by centrifugation. The harvested cells were resuspended in hypotonic lysis buffer (100 μl of 50 mM Tris, pH 10.0). The bacterial cells were lysed by subjecting the suspension to three cycles of freeze-thaw (dry ice-ethanol bath for freezing and 60° C. for thawing). The suspension was then sonicated for 10 min and centrifuged at 12,000 g for 10 min. The resulting supernatant was designated as "S1". The cell pellet was resuspended in 50 mM Tris, pH10 and 2×SDS tricine loading buffer (Novex, San Diego, Calif.) (1:1). The mixture was then heated at 95° C. for 15 min and centrifuged at 12,000 g for 10 min. The portion of the precipitate capable of being resolubilized in this manner was called "P1". The portion of the precipitate derived from the remaining pellet was called "P2". P2 was resuspended in loading buffer as for P1. Samples from S1, P1 and P2 were analyzed by SDS-PAGE.

SDS-PAGE gels were run using a two buffer tricine system in a minigel apparatus, with 10–20% tricine gels (Novex). Anode (bottom) buffer was 0.2 M Tris, pH 9.0. Cathode (top) buffer was 0.1 M Tris, 0.1 M Tricine, 0.1% SDS, pH 8.25. A commercial molecular weight marker, "Multi-Mark" (Novex) was used. Bovine ubiquitin, used as a standard, was purchased from Sigma. Gels were run at a constant current of 4 mA until the dye marker reached the bottom of the gel. Gels were stained with 0.25% Coomassie Blue R250 (Sigma) in acetic acid:methanol (10%:40%) and destained in the same solution minus the dye.

The majority (>70%) of the intact p141-ubiquitin fusion protein was found in the precipitate ($P_1$ and $P_2$) after centrifugation of the bacterial lysate. In sharp contrast, the majority (>70%) of the p97-ubiquitin fusion protein was found in the soluble fraction ($S_1$). This confirmed that the removal of the C-terminal hydrophobic region resulted in a product with improved solubility characteristics. Similarly, the p13 and p15 peptides were also contained in the soluble fraction.

The UCH-L3 ubiquinase enzyme (Recksteiner, M. (Ed.) *Ubiquitin*, Plenum Press (NY) 1988; Wilkinson et al., Science 246:670–73, 1989) was expressed in pRSET (Invitrogen, San Diego, Calif.) which was used to transform the host strain BL21/DE3. UCH-L3 is a ubiquitin-specific protease that cleaves at the ubiquitin C-terminal extension. It was partially purified from bacterial lysates by a 35% (w/v) ammonium sulfate precipitation. The exact percentage of ammonium sulfate used was monitored by SDS-PAGE for the presence of a 25.5 kD band. The supernatant was dialyzed against 50 mM Tris, pH 7.4, and assayed against a ubiquitin peptide fusion substrate. The active supernatant was aliquoted and frozen at −20° C. A typical reaction mixture contains 3 µl lysate, 1 µl 1M DTT, 1 µl UCH-L3 (as above) and 5 µl reaction buffer (50 mM Tris, pH 7.4). The reaction was carried out at room temperature for 20 min. For large scale digestion, 300 µl lysate was mixed with 100 µl 1M DTT, 20 µl UCH-L3 and 580 µl reaction buffer.

Peptides or proteins contained in the soluble ($S_1$) fraction were further purified by reverse phase HPLC as in Example 16; fractions were monitored by SDS-PAGE and their identity confirmed by electrospray ionization mass spectrometry (see below). The purified peptides or proteins were enzymatically digested by UCH-L3 as above, resulting in a non-ubiquinated final product. This cleaved material was then re-purified by reverse phase HPLC. Purification was followed by SDS-PAGE and the identity of the final product confirmed by electropray ionization mass spectrometry.

An alternative to the in vitro cleavage with UCH-L3 as described above is to co-express a ubiquitin cleaving enzyme in the same bacteria as the desired ubiquitin fusion. For this purpose, a vector (pJT184) expressing the ubiquinase UBP1 (Tobias and Varshavsky, JBC 266:12021–12028, 1991) was used. Bacteria co-expressing p97 ubiquitin fusion and UBP1 exhibited complete digestion of the fusion protein in vivo; bacteria co-expressing p141 ubiquitin fusion and UBP1 exhibited partial (approximately 70%) digestion of the fusion protein. The in vivo digested p97 protein was purified by ammonium sulfate precipitation followed by reverse-phase HPLC as above.

To confirm the identity of the expressed and purified polypeptides, electrospray ionization mass spectrometry was performed using a VG Biotech BIO-Q instrument with quadrupole analyser. Myoglobin was used to calibrate the instrument. The major component obtained with purified p97 was a single peak of molecular weight of 10,339 daltons; this compares favorably with the calculated molecular weight of 10,347, confirming the identity of the recombinant p97 fragment.

EXAMPLE 23

Recombinant p 1–97 Retains Stem Cell Inhibitory Activity

To assess the bioactivity of recombinant p1–97, the CFU-GEMM cycling assay was used as in Example 18:

TABLE 21

| Treatment | % Kill |
| --- | --- |
| Control[1] | 62 |
| Human Alpha[2] | 11 |
| p97[3] | 0 |

[1]Human bone marrow mononuclear cells
[2]Purified, non-recombinant human alpha hemoglobin, as in Example 16 (100 ng/ml)
[3]Purified recombinant p97, as in Example 22 (100 ng/ml)

EXAMPLE 24

Human Alpha Hemoglobin and Peptide 43–55 Inhibit CFU-MIX Cycling In Vivo in Testosterone or 5-Fluorouracil (5FU) Treated Mice To assess the stem cell inhibitory activity of peptide 43–55 in vivo, B6D2 $F_1$ mice were pre-treated with testosterone propionate as described in Example 1 or with 5FU. Specifically, testosterone propionate (100 mg/kg body weight) was injected i.p. on Day 0 into mice. Alternatively, mice were injected on Day 0 with 5FU (200 µg/kg body weight).

24 hours later (Day 1), varying doses of peptide 43–55 or vehicle were injected i.v. Bone marrow was harvested on Day 2 and the CFU-MIX cycling assay conducted as in Example 14. Specifically, mice were sacrificed and single cell bone marrow suspensions prepared from the femurs. The cells were washed once and the concentration adjusted to $5 \times 10^6$ cells/ml in Fischer medium. For each test condition, one milliliter of cells was added to each of two polypropylene tubes. The tubes were incubated at 37° C. for 3 hours without ("Control") or with ("Experimental") the appropriate concentration of test substance. At the end of the incubation, 30 µg/ml of cytosine arabinoside ("Ara C" (Sigma)) was added to half of the tubes and the same volume of Fischer's medium was added to the others. The tubes were incubated for a further 1 hour at 37° C., after which they were placed on ice and washed twice with cold Fischer medium.

The cells were readjusted to $5 \times 10^4 - 10^6$/ml in Fischer's medium and 0.5 ml of cell suspension added to 5 ml of Methocult M3430 methylcellulose medium (Stem Cell Technologies, Vancouver, British Columbia). The mixture was vigorously mixed with a vortex and 1 ml was dispensed into each of five 35 mm dishes. The 35 mm dishes were in turn placed in a covered 150 mm dish with one open 35 mm dish containing sterile water. CFU-MIX colonies were counted with the use of an inverted microscope after 7 days of incubation at 37° C.

Differences in colony number between the tubes treated with medium versus the tubes treated with Ara C represent the percentage of cells in cycle under that condition according to the formula:

$$\% S = \frac{a-b}{a} \times 100\%$$

where
  a=Number of CFU-MIX from tube incubated with medium alone
  b=Number of CFU-MD (from tube incubated with Ara C

TABLE 22[1]

| Treatment | % Kill |
| --- | --- |
| Control | 35 |
| Human Alpha Chain (500 ng)[2] | 13 |
| Peptide 43–55 (0.5 ng)[2] | 0 |

[1]Testosterone-pretreated animals
[2]Amount injected i.v. per 20 gram mouse

TABLE 23[1]

| Treatment | % Kill |
| --- | --- |
| Control | 62 |
| Human Alpha Chain (500 ng)[2] | 0 |
| Peptide 43–55 (0.5 ng)[2] | 3 |
| Cyclic Peptide 43–55 (0.5 ng)[2] | 14 |

[1]5FU-pretreated animals
[2]Amount injected i.v. per 20 gram mouse

EXAMPLE 25

Peptide 43–55 is Active as a Stem Cell Inhibitor when Biotinylated at the N-terminal Phe (Phe$_{43}$) or Iodinated at Phe$_{43}$ or Phe$_{46}$ Peptide 43–55 was synthesized by solid phase peptide synthetic techniques (American Peptide Co., Sunnyvale, Calif.). Peptide analogs were synthesized with iodine at the para position of Phe$_{43}$ or of Phe$_{46}$. Biotinylated Peptide 43–55 was synthesized by linking the COOH of biotin with a C$_4$ carbon linker to the N-terminal NH$_2$ of Phe$_{43}$.

TABLE 24

| Treatment | % Kill |
| --- | --- |
| Control | 31 |
| Peptide 43–55 (1 ng/ml) | 8 |
| Biotinylated peptide 43–55 (1 ng/ml) | 15 |

EXAMPLE 26

Morphine Inhibits Cycling of Murine CFU-MIX In Vitro

Morphine was tested in the CFU-MIX cycling assay using bone marrow from Balb/c mice as in Example 24:

TABLE 25

| Treatment | % Kill |
| --- | --- |
| Control | 44 |
| Human Alpha Chain (100 ng/ml) | 0 |
| Morphine | |
| ($10^{-7}$ M) | 10 |
| ($10^{-9}$ M) | 15 |
| ($10^{-11}$ M) | 32 |

EXAMPLE 27

The Opiate Peptides DAMGO and DALDA Inhibit Cycling of Murine CFU-MIX In Vitro

DAMGO and DALDA were tested in the CFU-MIX cycling assay using bone marrow from Balb/c mice as in Example 24:

TABLE 26

| Treatment | % Kill |
| --- | --- |
| Control | 33 |
| DAMGO | |
| ($10^{-5}$ M) | 15 |
| ($10^{-7}$ M) | 0 |
| ($10^{-9}$ M) | 38 |
| DALDA | |
| ($10^{-5}$ M) | 47 |
| ($10^{-7}$ M) | 0 |
| ($10^{-9}$ M) | 34 |

EXAMPLE 28

Nociceptin Inhibits Cycling of Murine CFU-MIX In Vitro

Nociceptin was tested in the CFU-MIX cycling assay using bone marrow from Balb/c mice as in Example 24:

TABLE 27

| Treatment | % Kill |
| --- | --- |
| Control | 31 |
| Peptide 43–55 (1 ng/ml) | 8 |
| Nociceptin | |
| ($10^{-7}$ M) | 6 |
| ($10^{-9}$ M) | 0 |

EXAMPLE 29

Naloxone Antagonizes the Inhibitory Activity of Human Alpha and Delta Hemoglobin Chains, Hemorphin 10 and Peptide 43–55

The CFU-MIX cycling assay was conducted as in Example 24. Test substances were assayed by themselves or in the presence of naloxone ($10^{-5}$–$10^{-7}$M). Naloxone itself had no effect on the assay at these concentrations.

TABLE 28

| Treatment | % Kill |
| --- | --- |
| Control | 38 |
| Naloxone[1] | 36 |
| Human Alpha (100 ng/ml) | 0 |
| Human Alpha (100 ng/ml) + Naloxone[1] | 52 |
| Peptide 43–55 (10 ng/ml) | 6 |
| Peptide 43–55 (10 ng/ml) + Naloxone[1] | 50 |
| Hemorphin 10 (100 ng/ml) | 0 |
| Hemorphin 10 (100 ng/ml) + Naloxone[1] | 36 |

[1]Used at $10^{-5}$ M final concentration

TABLE 29

| Treatment | % Kill |
| --- | --- |
| Control | 32 |
| Human Delta (100 ng/ml) | 10 |
| Human Delta (100 ng/ml) + Naloxone[1] | 31 |

[1] Used at $10^{-7}$ M final concentration

EXAMPLE 30

Low Concentrations of Naloxone Inhibit Cycling of Murine CFU-MIX

The CFU-MIX assay was conducted as in Example 24.

TABLE 30

| Treatment | % Kill |
| --- | --- |
| Control | 38 |
| Human Alpha (100 ng/ml) | 0 |
| Naloxone ($10^{-10}$ M) | 0 |

EXAMPLE 31

The mu Opiate Receptor Antagonist CTOP Antagonizes the Inhibitory Activity of Human Hemoglobin Alpha Chain, Peptide 43–55 and Peptide 64–82

CTOP (H-D-Phe-Cys-Tyr-D-Trp-Orn-Thr-Pen-Thr-NH$_2$, with a disulfide between Cys$_2$ and Pen$_7$) is an analog of somatostatin which is a mu opiate receptor specific antagonist Test substances were assayed by themselves or in the presence of CTOP ($10^{-7}$ M). CTOP itself had no effect on the assay at this concentration but antagonized the cell cycle inhibition caused by alpha hemoglobin or peptide 43–55.

TABLE 31

| Treatment | % Kill |
| --- | --- |
| Control | 42 |
| CTOP[1] | 36 |
| Human Alpha (100 ng/ml) | 0 |
| Human Alpha (100 ng/ml) + CTOP[1] | 20 |
| Peptide 43–55 (10 ng/ml) | 8 |
| Peptide 43–55 (10 ng/ml) + CTOP[1] | 21 |

[1] Used at $10^{-7}$ M, final concentration

EXAMPLE 32

Pretreatment with Human Alpha Chain Increases the Number of Late-Forming Cobblestone-Forming Cells The cobblestone assay was conducted as described by Ploemacher and colleagues (Ploemacher et al., Blood 74:2755–63, 1989; van der Sluijs et al., Exp. Hematol. 18:893–6, 1990; Ploemacher et al., Blood 78:2527–33, 1991; Ploemacher et al., J. Tiss. Cult. Meth. 13:63–68, 1991; Down and Ploemacher, Exp. Hematol. 21:213–21, 1993). The cobblestone assay measures the appearance of groups of cells (or "cobblestones") within a monolayer of stromal cells. Very primitive stem cells will not form colonies in soft agar but do form cobblestones in the presence of a stromal monolayer. The cells which form cobblestones are referred to as "cobblestone area forming cells" (CAFC). The more differentiated (e.g., GM-CFC) progenitors form transient cobblestones which appear and then disappear within the first few weeks of culture whereas more primitive stem cells (e.g., long-term repopulating cells) form cobblestones which appear only after 4–5 weeks of culture. Thus, CAFC forming on days 7–14 of culture are enriched in CFU-GM, CAFC forming on days 28–35 are enriched in CFU-MIX, and CAFC forming on days 28–35 are enriched in long-term repopulating cells.

B6D2F1 mice were treated with testosterone propionate as in Example 24. The next day bone marrow was removed and incubated for 4 hours with or without human alpha hemoglobin chain (100 ng/$10^6$ cells) after which they were plated in a cobblestone assay. The assay used consists of limiting dilution long term bone marrow cultures (LTBMC) in 96-well plates. The cultures were prepared by growing the FBMD-1 murine stromal cell line (Breems et al., Leukemia 11:142–50, 1997) until confluent; 96-well plates plates with confluent monolayers were stored at 33° C. until assay. Murine bone marrow cells were prepared as a single cell suspension and the following dilutions of cells were plated per well in 0.2 ml of LTBMC medium (Stem Cell Technologies, Vancouver): 27,000; 9000; 3000; 1000; 333. Twenty wells were plated for each dilution per condition and distributed over two plates.

Figure 23:
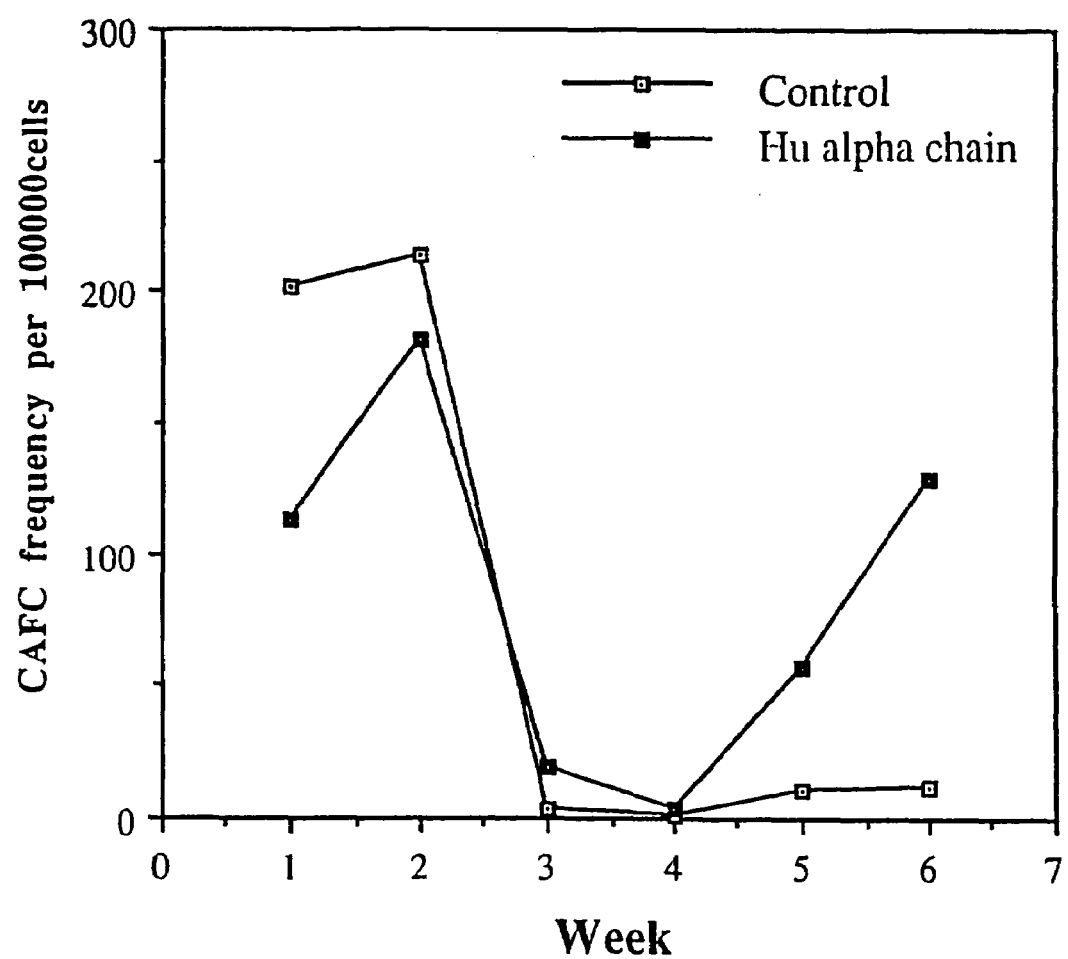
FIG. 23 shows the results of treatment with INPROL on the cobblestone assay.

The frequency of cobblestone area forming cells (CAFC) was calculated as previously described (Ploemacher et al., Blood 78:2527–33, 1991; Ploemacher et al., J. Tiss. Cult. Meth. 13:63–68, 1991; Breems et al., Leukemia 8:1095–104, 1994). The results are shown in FIG. 23. Preincubation of cycling stem cells with human alpha hemoglobin chain increased the proportion of late-forming CAFC by approximately 5-fold. Treatment of non-cycling stem cells with alpha chain had no effect.

EXAMPLE 33

Human Alpha Hemoglobin and Peptides 43–55, Cyclic 43–55 and 64–82 Inhibit Cycling of Human Cord Blood CFU-GEMM The human cord blood CFU-GEMM cycling assay was conducted as in Example 19. Specifically, mononuclear cells were isolated from human umbilical cord blood cells and adjusted to 2–4×10$^4$ cells/ml in IMDM tissue culture medium supplemented with 10% FBS, 100 ng/ml kit ligand and 100 ng/ml human IL-3. The cells were incubated for 48 hours at 37° C.

After incubation, cells were washed and resuspended in serum-free IMDM at a concentration of $10^6$ cells/ml. One ml of cells was added to each of two polypropylene tubes per condition and the cycling assay conducted as in Example 24 for mouse bone marrow. After the Ara C incubation cells were washed with cold IMDM and adjusted to 10,000 to 20,000 cells per 0.5 ml IMDM and mixed with 5 ml Methocult H4433 (Stem Cell Technologies). Alternatively, Methocult H4435 methylcellulose medium (Stem Cell Technologies) was used in which case the cell concentration was adjusted to 2500–5000 cells per 0.5 ml IMDM. The cells were plated as in Example 24 and CFU-GEMM colonies scored on days 14–18.

TABLE 32

| Treatment | % Kill |
|---|---|
| Control | 52 |
| Human Alpha Chain (100 ng/ml) | 0 |
| Peptide 43–55 | |
| (1 ng/ml) | 20 |
| (10 ng) | 12 |
| (100 ng) | 5 |
| Cyclic Peptide 43–55 | |
| (1 ng/ml) | 32 |
| (10 ng) | 0 |
| (100 ng) | 11 |
| Peptide 64–82 | |
| (1 ng/ml) | 21 |
| (10 ng) | 20 |
| (100 ng) | 39 |

EXAMPLE 34

Human Alpha Hemoglobin and Peptide 43–55 Inhibits Cycling of Adult Human Bone Marrow CFU-GEMM CD34+ stem cells were obtained from Poietic Technologies (Gaithersburg, Md.) after purification from human bone marrow by means of a CellPro column. Cells were incubated for 48 hours with kit ligand and IL-3 and used in a CFU-GEMM cycling assay in Example 26.

TABLE 33

| Treatment | % Kill |
|---|---|
| Control | 47 |
| Human Alpha Chain ( ng/ml) | 0 |
| Peptide 43–55 ( ng/ml) | 0 |

EXAMPLE 35

CFU-GEMM in Mobilized Human Peripheral Blood Actively Cycle and are Inhibitable by Human Alpha Hemoglobin, Peptide 43–55, DAMGO or Morphine Peripheral blood was obtained from breast cancer patients undergoing peripheral stem cell mobilization with cyclophosphamide and G-CSF according to standard protocols. Red blood cells were removed with Ficoll Hypaque (cells were diluted 1:1 with IMDM and 20 ml layered on top of 16 ml Ficoll and centrifuged at 800 g for 30 minutes; mononuclear cells were removed from the interphase and washed twice in IMDM). In one case mononuclear cells were stored frozen in liquid nitrogen before assay. The mononuclear cells were plated for the CFU-GEMM cycling assay as in Example 26 except that $2.5–5\times10^5$ cells were plated per dish.

TABLE 34

| Treatment | % Kill |
|---|---|
| Control (Patient #1) | 48 |
| Human Alpha Chain (100 ng/ml) | 0 |

TABLE 35

| Treatment | % Kill |
|---|---|
| Control (Patient #2)[1] | 67 |
| Human Alpha Chain ( ng/ml) | 2 |
| Peptide 43–55 (10 ng/ml) | 0 |
| Morphine ($10^{-7}$ M) | 24 |
| Morphine ($10^{-9}$ M) | 0 |
| DAMGO ($10^{-7}$ M) | 15 |
| DAMGO ($10^{-9}$ M) | 0 |

TABLE 36

| Treatment | % Kill |
|---|---|
| Control (Patient #3)[1] | 29 |
| Peptide 43–55 (0.1 ng/ml) | 23 |
| Peptide 43–55 (1.0 ng/ml) | 0 |
| Peptide 43–55 (10 ng/ml) | 15 |

[1]From cells stored frozen before assay

EXAMPLE 36

High Doses of Human Alpha or Beta Hemoglobin, Myoglobin, Peptide 1–97, Peptide 43–55, Peptide 64–82 Nociceptin or DALDA Stimulate Cycling of Quiescent Murine Stem Cells Microgram per milliliter doses of hemoglobin chains, myoglobin and peptides were assayed for stimulation of quiescent stem cells. Bone marrow was obtained from untreated $B6D2F_1$ tested in the CFU-MIX cycling assay as in Example 24. Stem cells isolated from untreated $B6D2F_1$ mice are normally slowly cycling unless stimulated (e.g. by testosterone propionate (cf. Example 1) or chemotherapy such as 5FU (cf. Example 4)) to enter into cycle.

TABLE 37

| Treatment | % Kill |
|---|---|
| Control | 3 |
| Human α Chain | |
| (1 µg/ml) | 0 |
| (10 µg/ml) | 24 |
| (100 µg/ml) | 40 |

TABLE 38

| Treatment | % Kill |
|---|---|
| Control | 9 |
| Human β Chain ( µg/ml) | 55 |
| Human Myoglobin ( µg/ml) | 30 |

TABLE 39

| Treatment | % Kill |
|---|---|
| Control | 3 |
| Human α Chain (100 μg/ml) | 41 |
| DALDA | |
| ($10^{-5}$ M) | 24 |
| ($10^{-3}$ M) | 41 |
| DADLE | |
| ($10^{-5}$ M) | 0 |
| ($10^{-3}$ M) | 0 |

TABLE 40

| Treatment | % Kill |
|---|---|
| Control | 0 |
| Human α Chain (100 μg/ml) | 30 |
| Peptide 43–55 (10 μg/ml) | 26 |

TABLE 41

| Treatment | % Kill |
|---|---|
| Control | 16 |
| Peptide 1–97 (10 μg/ml) | 62 |
| Peptide 1–97 (10 μg/ml) | 41 |

TABLE 42

| Treatment | % Kill |
|---|---|
| Control | 4 |
| Peptide 64–82 (1 μg/ml) | 25 |
| Nociceptin ($10^{-5}$ M) | 36 |

EXAMPLE 37

Intravenous Administration of High Dose Human Alpha Hemoglobin Stimulates Cycling of Quiescent Murine Stem Cells Human alpha hemoglobin was injected i.v. into untreated B6D2F$_1$ mice. 24 hours later, the mice were sacrificed, bone marrow collected from femurs and the CFU-MIX assay conducted as in Example 24.

TABLE 43

| Treatment | % Kill |
|---|---|
| Control (Untreated) | 0 |
| Medium (Injection Control) | 0 |
| Human α Chain (150 μg/mouse) | 48 |

EXAMPLE 38

Naloxone Antagonizes the Stem Cell Stimulatory Activity of High Dose Human Alpha Hemoglobin, Peptide 43–55

TABLE 44

| Treatment | % Kill |
|---|---|
| Contol | 6 |
| Human Alpha Chain (100 ng/ml) | 48 |
| Human Alpha Chain (100 ng/ml) + Naloxone[1] | 0 |

[1]Used at $10^{-7}$ M final concentration

While the present invention has been described in terms of preferred embodiments, it is understood that variations and modifications will occur to those skilled in the art Therefore, it is intended that the appended claims cover all such equivalent variations which come within the scope of the invention as claimed.

---

What is claimed is:

1. A method of stimulating stem cell division in a mammal exposed to an agent which damages or destroys stem cells comprising administering a stem cell proliferation stimulating amount of INPROL; wherein said INPROL is selected from the group consisting of the alpha chain of hemoglobin, the beta chain of hemoglobin, the gamma chain of hemoglobin, the delta chain of hemoglobin, the epsilon chain of hemoglobin, the zeta chain of hemoglobin, a polypeptide comprising the sequence of amino acids 1–97 of the human alpha hemoglobin chain a polypeptide comprising the sequence of amino acids 1–94 of the human alpha hemoglobin chain Phe-Pro-His-Phe-Asp-Leu-Ser-His-Gly-Ser-Ala-Gln-Val (SEQ ID NO:1), biotin-Phe-Pro-His-Phe-Asp-Leu-Ser-His-Gly-Ser-Ala-Gln-Val (SEQ ID NO:36), (iodo)Phe-Pro-His-Phe-Asp-Leu-Ser-His-Gly-Ser-Ala-Gln-Val (SEQ ID NO:37), Phe-Pro-His-(iodo)Phe-Asp-Leu-Ser-His-Gly-Ser-Ala-Gln-Val (SEQ ID NO:38), (iodo)Phe-Pro-His-(iodo)Phe-Asp-Leu-Ser-His-Gly-Ser-Ala-Gln-Val (SEQ ID NO:39), Cys-Phe-Pro-His-Phe-Asp-Leu-Ser-His-Gly-Ser-Ala-Gln-Val-Cys (SEQ ID NO:2), and Asp-Ala-Leu-Thr-Asn-Ala-Val-Ala-His-Val-Asp-Met-Pro-Asn-Ala-Leu-Ser-Ala (SEQ ID NO:3).

2. The method as in claim 1 wherein said agent is an antiviral agent or an anti-neoplastic agent.

3. The method as in claim 1 further comprising administering a stem cell proliferation stimulating amount of an opiate compound.

4. The method as in claim 3 wherein said opiate compound is selected from the group consisting of morphine, etorphine, codeine, heroin, hydromorphone, oxymorphone, levorphanol, levallorphan, codeine, hydrocodone, oxycodone, nalorphine, naloxone, naltrexone, buprenorphine, butanorphanol, nalbuphine, meperidine, alphaprodine, diphenoxylate, fentanyl, (D-Ala2,N-Me-Phe4,glycinol5)-Enkephalin, (D-Arg2,Lys4)-Dermorphin-(1-4)-amide, and nociceptin.

5. The method as in claim 1 wherein said INPROL is selected from the group consisting of
 Phe-Pro-His-Phe-Asp-Leu-Ser-His-Gly-Ser-Ala-Gln-Val (SEQ ID NO:1),
 Cys-Phe-Pro-His-Phe-Asp-Leu-Ser-His-Gly-Ser-Ala-Gln-Val-Cys (SEQ ID NO:2), and
 Asp-Ala-Leu-Thr-Asn-Ala-Val-Ala-His-Val-Asp-Met-Pro-Asn-Ala-Leu-Ser-Ala (SEQ ID NO:3).

6. The method as in claim 5 wherein said INPROL is Phe-Pro-His-Phe-Asp-Leu-Ser-His-Gly-Ser-Ala-Gln-Val (SEQ ID NO:1).

7. The method as in claim 3 wherein said INPROL is selected from the group consisting of
 Phe-Pro-His-Phe-Asp-Leu-Ser-His-Gly-Ser-Ala-Gln-Val (SEQ ID NO:1),
 Cys-Phe-Pro-His-Phe-Asp-Leu-Ser-His-Gly-Ser-Ala-Gln-Val-Cys (SEQ ID NO:2), and
 Asp-Ala-Leu-Thr-Asn-Ala-Val-Ala-His-Val-Asp-Met-Pro-Asn-Ala-Leu-Ser-Ala (SEQ ID NQ:3).

8. The method as in claim 7 wherein said INPROL is Phe-Pro-His-Phe-Asp-Leu-Ser-His-Gly-Ser-Ala-Gln-Val (SEQ ID NO:1).

* * * * *

SEQUENCE LISTING (1) GENERAL INFORMATION:

(iii) NUMBER OF SEQUENCES: 36

(2) INFORMATION FOR SEQ ID NO: 1:

(i) SEQUENCE CHARACTERISTICS:
      (A) LENGTH: 13 amino acids
      (B) TYPE: amino acid
      (C) STRANDEDNESS: <Unknown>
      (D) TOPOLOGY: linear (ii) MOLECULE TYPE: peptide (xi) SEQUENCE DESCRIPTION: SEQ ID NO: 1:

Phe Pro His Phe Asp Leu Ser His Gly Ser Ala Gln Val
1               5                   10

(2) INFORMATION FOR SEQ ID NO: 2:

```
    (i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 2:

Cys Phe Pro His Phe Asp Leu Ser His Gly Ser Ala Gln Val Cys
1               5                   10                  15

(2) INFORMATION FOR SEQ ID NO: 3:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

Asp Ala Leu Thr Asn Ala Val Ala His Val Asp Asp Met Pro Asn Al
1               5                   10                  15

Leu Ser Ala (2) INFORMATION FOR SEQ ID NO: 4:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

Leu Val Val Tyr Pro Trp Thr Gln Arg Phe
1               5                   10

(2) INFORMATION FOR SEQ ID NO: 5:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 5:

Leu Val Val Tyr Pro Trp Thr Gln Arg
1               5

(2) INFORMATION FOR SEQ ID NO: 6:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 6:

Leu Val Val Tyr Pro Trp Thr Gln
1               5
```

```
(2) INFORMATION FOR SEQ ID NO: 7:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 7:

Leu Val Val Tyr Pro Trp Thr
1               5

(2) INFORMATION FOR SEQ ID NO: 8:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 8:

Leu Val Val Tyr Pro Trp
1               5

(2) INFORMATION FOR SEQ ID NO: 9:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 9:

Leu Val Val Tyr Pro
1               5

(2) INFORMATION FOR SEQ ID NO: 10:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 10:

Val Val Tyr Pro Trp Thr Gln
1               5

(2) INFORMATION FOR SEQ ID NO: 11:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 11:

Tyr Pro Trp Thr Gln Arg Phe
```

(2) INFORMATION FOR SEQ ID NO: 12:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 12:

```
Tyr Pro Trp Thr Gln Arg
 1               5
```

(2) INFORMATION FOR SEQ ID NO: 13:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 13:

```
Tyr Pro Trp Thr Gln
 1               5
```

(2) INFORMATION FOR SEQ ID NO: 14:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 14:

```
Arg Met Trp Met Phe Arg
 1               5
```

(2) INFORMATION FOR SEQ ID NO: 15:

(i) SEQUENCE CHARACTERISTICS:
        (A) LENGTH: 423 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

```
GTGCTGTCTC CTGCCGACAA GACCAACGTC AAGGCCGCCT GGGGTAAGGT CGGCGCGCAC      60
GCTGGCGAGT ATGGTGCGGA GGCCCTGGAG AGGATGTTCC TGTCCTTCCC CACCACCAAG     120
ACCTACTTCC CGCACTTCGA CCTGAGCCAC GGCTCTGCCC AGGTTAAGGG CCACGGCAAG     180
AAGGTGGCCG ACGCGCTGAC CAACGCCGTG GCGCACGTGG ACGACATGCC CAACGCGCTG     240
TCCGCCCTGA GCGACCTGCA CGCGCACAAG CTTCGGGTGG ACCCGGTCAA CTTCAAGCTC     300
CTAAGCCACT GCCTGCTGGT GACCCTGGCC GCCCACCTCC CCGCCGAGTT CACCCCTGCG     360
GTGCACGCCT CCCTGGACAA GTTCCTGGCT TCTGTGAGCA CCGTGCTGAC CTCCAAATAC     420
CGT                                                                   423
```

(2) INFORMATION FOR SEQ ID NO: 16:

(i) SEQUENCE CHARACTERISTICS:
        (A) LENGTH: 141 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 16:

```
Val Leu Ser Pro Ala Asp Lys Thr Asn Val Lys Ala Ala Trp Gly Ly
1               5                   10                  15

Val Gly Ala His Ala Gly Glu Tyr Gly Ala Glu Ala Leu Glu Arg Me
            20                  25                  30

Phe Leu Ser Phe Pro Thr Thr Lys Thr Tyr Phe Pro His Phe Asp Le
        35                  40                  45

Ser His Gly Ser Ala Gln Val Lys Gly His Gly Lys Lys Val Ala As
    50                  55                  60

Ala Leu Thr Asn Ala Val Ala His Val Asp Asp Met Pro Asn Ala Le
65                  70                  75                  80

Ser Ala Leu Ser Asp Leu His Ala His Lys Leu Arg Val Asp Pro Va
                85                  90                  95

Asn Phe Lys Leu Leu Ser His Cys Leu Leu Val Thr Leu Ala Ala Hi
                100                 105                 110

Leu Pro Ala Glu Phe Thr Pro Ala Val His Ala Ser Leu Asp Lys Ph
            115                 120                 125

Leu Ala Ser Val Ser Thr Val Leu Thr Ser Lys Tyr Arg
        130                 135                 140
```

(2) INFORMATION FOR SEQ ID NO: 17:

(i) SEQUENCE CHARACTERISTICS:
        (A) LENGTH: 438 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
GTGCACCTGA CTCCTGAGGA GAAGTCTGCC GTTACTGCCC TGTGGGGCAA GGTGAACGTG     60

GATGAAGTTG GTGGTGAGGC CCTGGGCAGG CTGCTGGTGG TCTACCTTTG GACCCAGAGG    120

TTCTTTGAGT CCTTTGGGGA TCTGTCCACT CCTGATGCTG TTATGGGCAA CCCTAAGGTG    180

AAGGCTCATG GCAAGAAAGT GCTCGGTGCC TTTAGTGATG GCCTGGCTCA CCTGGACAAC    240

CTCAAGGGCA CCTTTGCCAC ACTGAGTGAG CTGCACTGTG ACAAGCTGCA CGTGGATCCT    300

GAGAACTTCA GGCTGCTGGG CAACGTGCTG GTCTGTGTGC TGGCCCATCA CTTTGGCAAA    360

GAATTCACCC CACCAGTGCA GGCTGCCTAT CAGAAAGTGG TGGCTGGTGT GGCTAATGCC    420

CTGGCCCACA AGTATCAC                                                 438
```

(2) INFORMATION FOR SEQ ID NO: 18:

(i) SEQUENCE CHARACTERISTICS:
        (A) LENGTH: 146 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 18:

Val His Leu Thr Pro Glu Glu Lys Ser Ala Val Thr Ala Leu Trp Gl
1               5                   10                  15

Lys Val Asn Val Asp Glu Val Gly Gly Glu Ala Leu Gly Arg Leu Le
                20                  25                  30

Val Val Tyr Pro Trp Thr Gln Arg Phe Phe Glu Ser Phe Gly Asp Le
            35                  40                  45

Ser Thr Pro Asp Ala Val Met Gly Asn Pro Lys Val Lys Ala His Gl
        50                  55                  60

Lys Lys Val Leu Gly Ala Phe Ser Asp Gly Leu Ala His Leu Asp As
65                  70                  75                  80

Leu Lys Gly Thr Phe Ala Thr Leu Ser Glu Leu His Cys Asp Lys Le
                85                  90                  95

His Val Asp Pro Glu Asn Phe Arg Leu Leu Gly Asn Val Leu Val Cy
            100                 105                 110

Val Leu Ala His His Phe Gly Lys Glu Phe Thr Pro Pro Val Gln Al
            115                 120                 125

Ala Tyr Gln Lys Val Val Ala Gly Val Ala Asn Ala Leu Ala His Ly
        130                 135                 140

Tyr His
145

(2) INFORMATION FOR SEQ ID NO: 19:

(i) SEQUENCE CHARACTERISTICS:
        (A) LENGTH: 141 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 19:

Val Leu Ser Gly Glu Asp Lys Ser Asn Ile Lys Ala Ala Trp Gly Ly
1               5                   10                  15

Ile Gly Gly His Gly Ala Glu Tyr Gly Ala Glu Ala Leu Glu Arg Me
                20                  25                  30

Phe Ala Ser Phe Pro Thr Thr Lys Thr Tyr Phe Pro His Phe Asp Va
            35                  40                  45

Ser His Gly Ser Ala Gln Val Lys Gly His Gly Lys Lys Val Ala As
        50                  55                  60

Ala Leu Ala Ser Ala Ala Gly His Leu Asp Asp Leu Pro Gly Ala Le
65                  70                  75                  80

Ser Ala Leu Ser Asp Leu His Ala His Lys Leu Arg Val Asp Pro Va
                85                  90                  95

Asn Phe Lys Leu Leu Ser His Cys Leu Leu Val Thr Leu Ala Ser Hi
            100                 105                 110

His Pro Ala Asp Phe Thr Pro Ala Val His Ala Ser Leu Asp Lys Ph
            115                 120                 125

Leu Ala Ser Val Ser Thr Val Leu Thr Ser Lys Tyr Arg
        130                 135                 140

(2) INFORMATION FOR SEQ ID NO: 20:

(i) SEQUENCE CHARACTERISTICS:
        (A) LENGTH: 146 amino acids
        (B) TYPE: amino acid

```
            (C) STRANDEDNESS: <Unknown>
            (D) TOPOLOGY: linear (ii) MOLECULE TYPE: peptide (xi) SEQUENCE DESCRIPTION: SEQ ID NO: 20:

Val His Leu Thr Asp Ala Glu Lys Ala Ala Val Ser Cys Leu Trp Gl
1               5                   10                  15

Lys Val Asn Ser Asp Glu Val Gly Gly Glu Ala Leu Gly Arg Leu Le
            20                  25                  30

Val Val Tyr Pro Trp Thr Gln Arg Tyr Phe Asp Ser Phe Gly Asp Le
            35                  40                  45

Ser Ser Ala Ser Ala Ile Met Gly Asn Ala Lys Val Lys Ala His Gl
        50                  55                  60

Lys Lys Val Ile Thr Ala Phe Asn Asp Gly Leu Asn His Leu Asp Se
65                  70                  75                  80

Leu Lys Gly Thr Phe Ala Ser Leu Ser Glu Leu His Cys Asp Lys Le
                85                  90                  95

His Val Asp Pro Glu Asn Phe Arg Leu Leu Gly Asn Met Ile Val Il
            100                 105                 110

Val Leu Gly His His Leu Gly Lys Asp Phe Thr Pro Ala Ala Gln Al
            115                 120                 125

Ala Phe Gln Lys Val Val Ala Gly Val Ala Thr Ala Leu Ala His Ly
        130                 135                 140

Tyr His
145

(2) INFORMATION FOR SEQ ID NO: 21:

(i) SEQUENCE CHARACTERISTICS:
        (A) LENGTH: 141 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 21:

Val Leu Ser Ala Ala Asp Lys Ala Asn Val Lys Ala Ala Trp Gly Ly
1               5                   10                  15

Val Gly Gly Gln Ala Gly Ala His Gly Ala Glu Ala Leu Glu Arg Me
            20                  25                  30

Phe Leu Gly Phe Pro Thr Thr Lys Thr Tyr Phe Pro His Phe Asn Le
            35                  40                  45

Ser His Gly Ser Asp Gln Val Lys Ala His Gly Gln Lys Val Ala As
        50                  55                  60

Ala Leu Thr Lys Ala Val Gly His Leu Asp Asp Leu Pro Gly Ala Le
65                  70                  75                  80

Ser Ala Leu Ser Asp Leu His Ala His Lys Leu Arg Val Asp Pro Va
                85                  90                  95

Asn Phe Lys Leu Leu Ser His Cys Leu Leu Val Thr Leu Ala Ala Hi
            100                 105                 110

His Pro Asp Asp Phe Asn Pro Ser Val His Ala Ser Leu Asp Lys Ph
            115                 120                 125

Leu Ala Asn Val Ser Thr Val Leu Thr Ser Lys Tyr Arg
        130                 135                 140

(2) INFORMATION FOR SEQ ID NO: 22:
```

```
        (i) SEQUENCE CHARACTERISTICS:
            (A) LENGTH: 146 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 22:

Val His Leu Ser Ala Glu Glu Lys Glu Ala Val Leu Gly Leu Trp Gl
1               5                   10                  15
Lys Val Asn Val Asp Glu Val Gly Gly Glu Ala Leu Gly Arg Leu Le
            20                  25                  30
Val Val Tyr Pro Trp Thr Gln Arg Phe Phe Glu Ser Phe Gly Asp Le
        35                  40                  45
Ser Asn Ala Asp Ala Val Met Gly Asn Pro Lys Val Lys Ala His Gl
    50                  55                  60
Lys Lys Val Leu Gln Ser Phe Ser Asp Gly Leu Lys His Leu Asp As
65                  70                  75                  80
Leu Lys Gly Thr Phe Ala Lys Leu Ser Glu Leu His Cys Asp Gln Le
                85                  90                  95
His Val Asp Pro Glu Asn Phe Arg Leu Leu Gly Asn Val Ile Val Va
            100                 105                 110
Val Leu Ala Arg Arg Leu Gly His Asp Phe Asn Pro Asp Val Gln Al
        115                 120                 125
Ala Phe Gln Lys Val Val Ala Gly Val Ala Asn Ala Leu Ala His Ly
    130                 135                 140
Tyr His
145

(2) INFORMATION FOR SEQ ID NO: 23:

(i) SEQUENCE CHARACTERISTICS:
            (A) LENGTH: 23 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 23:

Val His Leu Ser Ala Glu Glu Lys Glu Ala Val Leu Gly Leu Trp Gl
1               5                   10                  15
Lys Val Asn Val Asp Glu Val
            20

(2) INFORMATION FOR SEQ ID NO: 24:

(i) SEQUENCE CHARACTERISTICS:
            (A) LENGTH: 20 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 24:

Val Leu Ser Ala Ala Asp Lys Ala Asn Val Lys Ala Ala Trp Gly Ly
1               5                   10                  15
Val Gly Gly Gln
            20
```

(2) INFORMATION FOR SEQ ID NO: 25:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 25:

```
Phe Pro His Phe Asn Leu Ser His Gly Ser Asp Gln Val Lys
1               5                   10
```

(2) INFORMATION FOR SEQ ID NO: 26:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 26:

```
Val Val Tyr Pro Trp Thr Gln Arg
1               5
```

(2) INFORMATION FOR SEQ ID NO: 27:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 27:

```
Tyr Pro Trp Thr
1
```

(2) INFORMATION FOR SEQ ID NO: 28:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 28:

```
Gly Tyr Pro Tyr
1
```

(2) INFORMATION FOR SEQ ID NO: 29:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 29:

```
Gly Lys Pro Tyr
1
```

(2) INFORMATION FOR SEQ ID NO: 30:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 30:

Gly Leu Pro Tyr
1

(2) INFORMATION FOR SEQ ID NO: 31:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 31:

Lys Met Trp Met Phe Arg
1               5

(2) INFORMATION FOR SEQ ID NO: 32:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 32:

Val Arg Arg Met Phe Gly Gly Tyr
1               5

(2) INFORMATION FOR SEQ ID NO: 33:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

Phe Leu Gly Phe Pro Thr
1               5

(2) INFORMATION FOR SEQ ID NO: 34:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1

```
            (D) OTHER INFORMATION: /product= "position 1"
                /label= Xaa
                /note= "pyroGln"

(xi) SEQUENCE DESCRIPTION: SEQ ID NO: 34:

Xaa Gln Gln Asp Cys Lys
1               5

(2) INFORMATION FOR SEQ ID NO: 35:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "position 1"
            /label= Xaa
            /note= "N-AcetylSer"

(xi) SEQUENCE DESCRIPTION: SEQ ID NO: 35:

Xaa Asp Lys Pro
1

(2) INFORMATION FOR SEQ ID NO: 36:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "position 1"
            /label= Xaa
            /note= "biotin-Phe, Phe or iodo-Phe"

(ix) FEATURE:
        (A) NAME/KEY: Modified-site
        (B) LOCATION: 4
        (D) OTHER INFORMATION: /product= "position 4"
            /label= Xaa
            /note= "Phe, iodo-Phe"

(xi) SEQUENCE DESCRIPTION: SEQ ID NO: 36:

Xaa Pro His Xaa Asp Leu Ser His Gly Ser Ala Gln Val
1               5                   10
```